United States Patent
Kaspar et al.

(10) Patent No.: US 10,793,861 B2
(45) Date of Patent: Oct. 6, 2020

(54) PRODUCTS AND METHODS FOR TREATMENT OF FAMILIAL AMYOTROPHIC LATERAL SCLEROSIS

(71) Applicants: RESEARCH INSTITUTE AT NATIONWIDE CHILDREN'S HOSPITAL, Columbus, OH (US); LUDWIG INSTITUTE FOR CANCER RESEARCH, Zurich (CH)

(72) Inventors: Brian K. Kaspar, Columbus, OH (US); Kevin Foust, Columbus, OH (US); Don W. Cleveland, La Jolla, CA (US)

(73) Assignees: RESEARCH INSTITUTE AT NATIONWIDE CHILDREN'S HOSPITAL, Columbus, OH (US); LUDWIG INSTITUTE FOR CANCER RESEARCH, Zurich (CH)

( * ) Notice: Subject to any disclaimer, the term of this patent is extended or adjusted under 35 U.S.C. 154(b) by 82 days.

(21) Appl. No.: 16/041,381

(22) Filed: Jul. 20, 2018

(65) Prior Publication Data
US 2019/0144868 A1    May 16, 2019

Related U.S. Application Data

(63) Continuation of application No. 14/914,861, filed as application No. PCT/US2014/052753 on Aug. 26, 2014, now abandoned.

(60) Provisional application No. 61/870,585, filed on Aug. 27, 2013.

(51) Int. Cl.
| | |
|---|---|
| *C12N 15/113* | (2010.01) |
| *A61K 31/7105* | (2006.01) |
| *A61K 9/00* | (2006.01) |
| *C12N 15/86* | (2006.01) |
| *C12N 7/00* | (2006.01) |
| *C12N 9/02* | (2006.01) |

(52) U.S. Cl.
CPC ........ *C12N 15/1137* (2013.01); *A61K 9/0019* (2013.01); *A61K 31/7105* (2013.01); *C12N 7/00* (2013.01); *C12N 9/0089* (2013.01); *C12N 15/86* (2013.01); *C12Y 115/01001* (2013.01); *C12N 2310/14* (2013.01); *C12N 2310/531* (2013.01); *C12N 2320/32* (2013.01); *C12N 2750/14043* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 7,498,316 B2 * | 3/2009 | Xu | 436/6 |

FOREIGN PATENT DOCUMENTS

| | | |
|---|---|---|
| WO | WO-1995/13365 A1 | 5/1995 |
| WO | WO-1995/13392 A1 | 5/1995 |
| WO | WO-1996/17947 A1 | 6/1996 |
| WO | WO-1997/06243 A1 | 2/1997 |
| WO | WO-1997/08298 A1 | 3/1997 |
| WO | WO-1997/09441 A2 | 3/1997 |
| WO | WO-1997/21825 A1 | 6/1997 |
| WO | WO-1998/09657 A3 | 4/1998 |
| WO | WO-1999/11764 A3 | 6/1999 |
| WO | WO-2005/096781 A2 | 10/2005 |
| WO | WO-2006/066203 A2 | 6/2006 |
| WO | WO-2009/013290 A1 | 1/2009 |
| WO | WO-2009/043936 A1 | 4/2009 |
| WO | WO-2009/102427 A2 | 8/2009 |
| WO | WO-2010/071832 A1 | 6/2010 |
| WO | WO-2011/133890 A1 | 10/2011 |
| WO | WO-2012/058220 A2 | 5/2012 |
| WO | WO-2014/071219 A1 | 5/2014 |

OTHER PUBLICATIONS

Phillips (1997) "Antisense Inhibition and Adeno-Associated Viral Vector Delivery for Reducing Hypertension", Hypertension, 29: 177-87. (Year: 1997).*
Glatzel, et al. (2000) "Adenoviral and adeno-associated viral transfer of genes to the peripheral nervous system", Proceedings of the National Academy of Science, USA, 97(1): 442-47. (Year: 2000).*
Henricksen, et al. (2007) "Comparison of RNAi efficiency mediated by tetracycline-responsive H1 and U6 promoter variants in mammalian cell lines", Nucleic Acids Research, 35(9): article e67, 8 pages long. (Year: 2007).*
Sandig, et al. (2000) "Optimization of the helper-dependent adenovirus system for production and potency in vivo", Proceedings of the National Academy of Sciences, USA., 97(3): 1002-07. (Year: 2000).*
Federici, et al. (2012) "Robust spinal motor neuron transduction following intrathecal delivery of AAV9 in pigs", Gene Therapy, 19: 852-59. (Year: 2012).*
Debnam, et al. (2009) "Multidetector CT-Guided Lumbar Puncture in Patients with Cancer", Interventional Neuroradiology, 15: 6166. (Year: 2009).*

(Continued)

*Primary Examiner* — Robert M Kelly
(74) *Attorney, Agent, or Firm* — Marshall, Gerstein & Borun LLP

(57) ABSTRACT

The present invention relates to RNA-based methods for inhibiting the expression of the superoxide dismutase 1 (SOD-1) gene. Recombinant adeno-associated viruses of the invention deliver DNAs encoding RNAs that knock down the expression of SOD-1. The methods have application in the treatment of amyotrophic lateral sclerosis.

15 Claims, 22 Drawing Sheets
Specification includes a Sequence Listing.

(56) References Cited

OTHER PUBLICATIONS

Philips, et al. (2015) "Rodent Models of Amyotrophic Lateral Sclerosis", Current Protocols in Pharmacology, 69: pp. 5.67.1-5.67.21 (Year: 2015).*

Aggarwal et al., M. ALS drug development: reflections from the past and a way forward, *Neurotherapeutics: The Journal of the American Society for Experimental Neuro Therapeutics*. 5:516-27 (2008).

Bevan et al., Systemic gene delivery in large species for targeting spinal cord, brain, and peripheral tissues for pediatric disorders, *Mol. Ther*. 19:1971-80 (2011).

Boillee et al., Onset and progression in inherited ALS determined by motor neurons and microglia, *Science*. 312:1389-92 (2006).

Bosco et al., Wild-type and mutant SOD1 share an aberrant conformation and a common pathogenic pathway in ALS, *Nature Neuroscience*. 13:1396-1403 (2010).

Carter, Adeno-associated virus vectors, *Current Opinions in Biotechnology*. 3:533-539 (1992).

Chattopadhyay et al., Aggregation of copper-zinc superoxide dismutase in familial and sporadic ALS, *Antioxidants & Redox Signaling*. 11:1603-14 (2009).

Clark et al., A stable cell line carrying adenovirus-inducible rep and cap genes allows for infectivity titration of adeno-associated virus vectors, *Gene Therapy*. 3:1124-32 (1996).

Clark et al., Highly purified recombinant adeno-associated virus vectors are biologically active and free of detectable helper and wild-type viruses, *Hum. Gene Ther*. 10:1031-9 (1999).

Da Cruz et al., Understanding the role of TDP-43 and FUS/TLS in ALS and beyond, *Curr. Opin. Neurobiol*. 21:904-19 (2011).

De et al., High levels of persistent expression of alpha1-antitrypsin mediated by the nonhuman primate serotype rh.10 adeno-associated virus despite preexisting immunity to common human adeno-associated viruses, *Mol. Ther*. 13:67-76 (2006).

Di Giorgio et al., Human embryonic stem cell-derived motor neurons are sensitive to the toxic effect of glial cells carrying an ALS-causing mutation, *Cell Stem Cell*. 3:637-48 (2008).

Di Giorgio et al., Non-cell autonomous effect of glia on motor neurons in an embryonic stem cell-based ALS model, *Nature neuroscience*. 10:608-14 (2007).

Ding et al., Selective silencing by RNAi of a dominant allele that causes amyotrophic lateral sclerosis, *Aging Cell*. 2: 209-17 (2003).

Duque et al., Intravenous administration of self-complementary AAV9 enables transgene delivery to adult motor neurons, *Mol Ther*. 17:1187-96 (2009).

Forsberg et al., Novel antibodies reveal inclusions containing non-native SOD1 in sporadic ALS patients, *PLoS One*. 5:e11552 (2010).

Foust et al., Intravascular AAV9 preferentially targets neonatal neurons and adult astrocytes, *Nature Biotechnology*. 27:59-65 (2009).

Gao et al., Clades of Adeno-associated viruses are widely disseminated in human tissues, *J. Virol*. 78:6381-8 (2004).

GenBank Accession No. NC_001829, Adeno-associated virus-4, complete genome, dated Jan. 28, 2010.

GenBank Accession No. AF085716, Adeno-associated virus 5 DNA binding trs helicase (Rep22) and capsid protein (VP1) genes, complete cds, dated Feb. 9, 1999.

Genbank Accession No. AX753246, Sequence 1 from Patent EP1310571, dated Jun. 23, 2003.

Genbank Accession No. AX753249, Sequence 4 from Patent EP1310571, dated Jun. 23, 2003.

GenBank Accession No. NC 001401, Adeno-associated virus-2, complete genome, Dec. 2, 2014.

GenBank Accession No. NC_001862, Adeno-associated virus 6, complete genome, dated Jan. 12, 2004.

GenBank Accession No. NC_002077, Adeno-associated virus-1, complete genome, dated Mar. 11, 2010.

Gray et al., Preclinical differences of intravascular AAV9 delivery to neurons and glia: a comparative study of adult mice and nonhuman primates, *Mol Ther*. 19:1058-69 (2011).

Grimm et al., Adeno-Associated Virus Vectors for Short Hairpin RNA Expression, *Methods in Enzymology*. 392:381-405 (2005).

Guareschi et al., An over-oxidized form of superoxide dismutase found in sporadic amyotrophic lateral sclerosis with bulbar onset shares a toxic mechanism with mutant SOD1, *Proc. Natl. Acad. Sci. USA*. 109:5074-9 (2012).

Gurney et al., Benefit of vitamin E, riluzole, and gabapentin in a transgenic model of familial amyotrophic lateral sclerosis, *Ann Neurol*. 39:147-57 (1996).

Haidet-Phillips et al., Astrocytes from familial and sporadic ALS patients are toxic to motor neurons, *Nat. Biotechnol*. 29:824-8 (2011).

Hermonat et al., Use of adeno-associated virus as a mammalian DNA cloning vector: transduction of neomycin resistance into mammalian tissue culture cells, *Proc. Natl. Acad. Sci. USA*. 81:6466 (1984).

Ilieva et al., Non-cell autonomous toxicity in neurodegenerative disorders: ALS and beyond, *The Journal of Cell Biology*. 187:761-72 (2009).

International Preliminary Report on Patentability, European Patent Office, PCT/US2014/052753, dated Mar. 3, 2016.

International Search Report and Written Opinion of the International Search Authority, European Patent Office, PCT/US2014/052753 dated Nov. 24, 2014.

Kang et al., Degeneration and impaired regeneration of gray matter oligodendrocytes in amyotrophic lateral sclerosis, *Nature Neuroscience*. 16:571-9 (2013).

Kaplitt et al., Safety and tolerability of gene therapy with an adeno-associated virus (AAV) borne GAD gene for Parkinson's disease: an open label, phase I trial, *Lancet*. 369:2097-105 (2007).

Laughlin et al., Cloning of infectious adeno-associated virus genomes in bacterial plasmid, *Gene*. 23:65-73 (1983).

Lebkowski et al., Adeno-associated virus: a vector system for efficient introduction and integration of DNA into a variety of mammlian cell types, *Mol. Cell. Biol*. 8:3988-96 (1988).

Lioy et al., A role for glia in the progression of Rett's syndrome, *Nature*. 475:497-500 (2011).

Machida et al., Intraperitoneal administration of AAV9-shRNA inhibits target gene expression in the dorsal root ganglia of neonatal mice, *Molec. Pain. BioMed Cent*. 9(1):36 (2013).

Mandel et al., AAV6-mediated gene silencing fALS short, *Mol. Ther*. 19:231-3 (2011).

Marchetto et al., Non-cell-autonomous effect of human SOD1 G37R astrocytes on motor neurons derived from human embryonic stem cells, *Cell Stem Cell*. 3:649-57 (2008).

Marks et al., Safety and tolerability of intraputaminal delivery of CERE-120 (adeno-associated virus serotype 2-neurturin) to patients with idiopathic Parkinson's disease: an open-label, phase I trial, *Lancet Neurol*. 7: 400-8 (2008).

McLaughlin et al., Adeno-associated virus general transduction vectors: analysis of proviral structures, *J. Virol*. 62:1963 (1988).

Miller et al., An antisense oligonucleotide against SOD1 delivered intrathecally for patients with SOD1 familial amyotrophic lateral sclerosis: a phase 1, randomised, first-in-man study, *Lancet Neurology*. 12:435-42 (2013).

Miller et al., Riluzole for amyotrophic lateral sclerosis (ALS)/motor neuron disease (MND). *Cochrane Database Syst Rev*. 3:1-36 (2012).

Miller et al., Virus-delivered small RNA silencing sustains strength in amyotrophic lateral sclerosis, *Annals of Neurology*. 57:773-6 (2005).

Miranda et al., Aging brain microenvironment decreases hippocampal neurogenesis through Wnt-mediated survivin signaling, *Aging Cell*. 11:542-52 (2012).

Mori et al., Two novel adeno-associated viruses from cynomolgus monkey: pseudotyping characterization of capsid protein, *Virology*. 330:375-83 (2004).

Musatov et al., RNAi-mediated silencing of estrogen receptor in the ventromedial nucleus of hypothalamus abolishes female sexual behaviors, *Proceedings of the National Academy of Sciences*. 27:10456-60 (2006).

Muzyczka, Use of adeno-associated virus as a general transduction vector for mammalian cells, *Curr. Topics in Microbial. and Immunol*. 158:97-129 (1992).

(56) References Cited

OTHER PUBLICATIONS

Pacak et al., Recombinant Adeno-associated virus serotype 9 leads to preferential cardiac transduction in vivo, *Circ. Res.* 99: 3-9 (2006).

Paul et al., Increased viral titer through concentration of viral harvests from retroviral packaging lines, *Human Gene Therapy*. 4:609-15 (1993).

Perrin et al., An experimental rabies vaccine produced with a new BHK-21 suspension cell culture process: use of serum-free medium and perfusion-reactor system, *Vaccine*. 13:1244-50 (1995).

Pokrishevsky et al., Aberrant localization of FUS and TDP43 is associated with misfolding of SOD1 in amyotrophic lateral sclerosis, *PloS one*. 7: e35050 (2012).

Prudencio et al., Variation in aggregation propensities among ALS-associated variants of SOD1: correlation to human disease, *Human Molecular Genetics*. 18:3217-26 (2009).

Ralph et al., Silencing mutant SOD1 using RNAi protects against neurodegeneration and extends survival in an ALS model, *Nat Med*. 11:429-33 (2005).

Raoul et al., Lentiviral-mediated silencing of SOD1 through RNA interference retards disease onset and progression in a mouse model of ALS, *Nat Med*. 11:423-8 (2005).

Rosen et al., Mutations in Cu/Zn superoxide dismutase gene are associated with familial amyotrophic lateral sclerosis, *Nature*. 362:59-62 (1993).

Ruffing et al., Mutations in Cu/Zn superoxide dismutase gene are associated with familial amyotrophic lateral sclerosis, *J Gen Viro*. 75: 3385-92 (1994).

Samulski et al., Cloning of adeno-associated virus into pBR322: rescue of intact virus from the recombinant plasmid in human cells, *Proc. Natl. Acad. Sci. USA*. 79:2077-81 (1982).

Samulski et al., Mutations in the carboxy terminus of adeno-associated virus 2 capsid proteins affect viral infectivity: lack of an RGD integrin-binding motif, *J. Virol*. 63:3822-8 (1989).

Schenpp et al., Highly purified recombinant adeno-associated virus vectors. Preparation and quantitation, *Methods Mol. Med*. 69:427-43 (2002).

Senapathy et al., Molecular cloning of adeno-associated virus variant genomes and generation of infectious virus by recombination in mammalian cells, *J. Biol. Chem*. 259:4661-4666 (1984).

Smith et al., Antisense oligonucleotide therapy for neurodegenerative disease, *The Journal of Clinical Investigation*. 116: 2290-6 (2006).

Snyder et al., Comparison of adeno-associated viral vector serotypes for spinal cord and motor neuron gene delivery, *Hum. Gene Ther*. 22:1129-35 (2011).

Srivastava et al., Nucleotide sequence and organization of the adeno-associated virus 2 genome, *J Virol*, 45: 555-64 (1983).

Synofzik et al., Mutant superoxide dismutase-1 indistinguishable from wild-type causes ALS, *Human Molecular Genetics*. 21:3568-74 (2012).

Towne et al., Neuroprotection by gene therapy targeting mutant SOD1 in individual pools of motor neurons does not translate into therapeutic benefit in fALS mice, *Mol. Ther*. 19:274-83 (2011).

Towne et al., Systemic AAV6 delivery mediating RNA interference against SOD1: neuromuscular transduction does not alter disease progression in fALS mice, *Mol. Ther*. 16:1018-25 (2008).

Tratschin et al., A Human Parvovirus, Adeno-Associated Virus, as a Eucaryotic Vector, Transient Expression and Encapsidation of the Procaryotic Gene for Chloramphenicol Acetyltranserase, *Mol. Cell. Biol*. 4:2072 (1984).

Tratschin et al., Adeno-associated virus vector for high-frequency integration, expression, and rescue of genes in mammalian cells, *Mol. Cell. Biol*. 5:3251 (1985).

Wang et al., Adeno-associated virus serotype 8 efficiently delivers genes to muscle and heart, *Nature Biotech*. 23: 321-8 (2005).

Worgall et al., Treatment of late infantile neuronal ceroid lipofuscinosis by CNS administration of a serotype 2 adeno-associated virus expressing CLN2 cDNA, *Hum. Gene. Ther*. 19:463-74 (2008).

Yamanaka et al., Astrocytes as determinants of disease progression in inherited amyotrophic lateral sclerosis, *Nature Neuroscience*. 11:251-3 (2008).

Yamanaka et al., Mutant SOD1 in cell types other than motor neurons and oligodendrocytes accelerates onset of disease in ALS mice, *Proc. Natl. Acad. Sci. USA*. 105:7594-9 (2008).

Zhong et al., ALS-causing SOD1 mutants generate vascular changes prior to motor neuron degeneration, *Nature Neuroscience*. 11:420-2 (2008).

\* cited by examiner

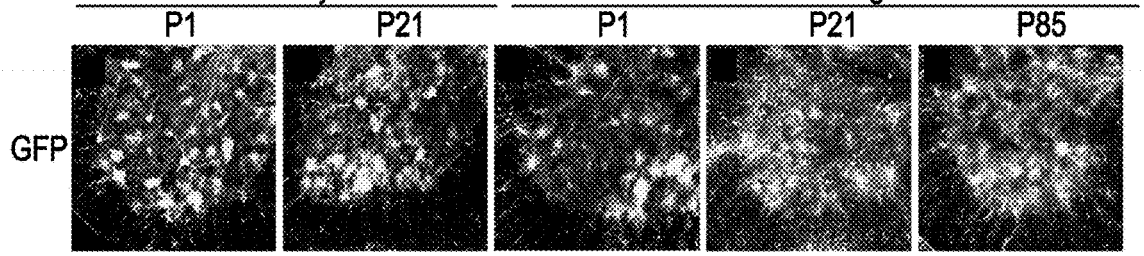
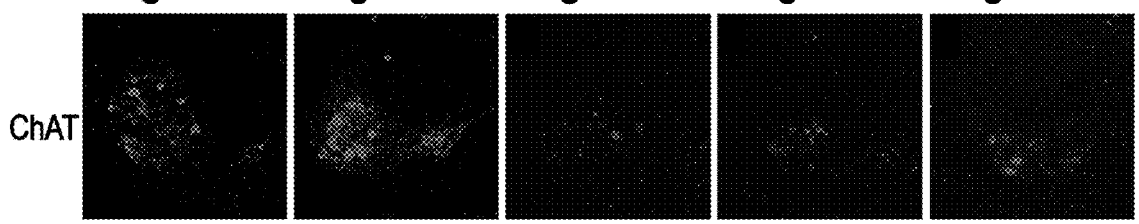
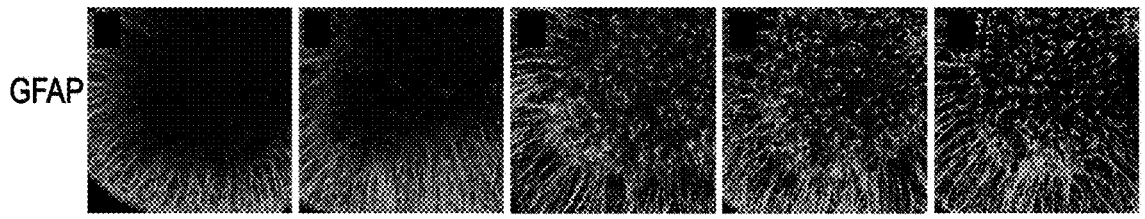
Figure 1U
21d Post Injection
|  | GFP | ChAT | %(Mean ± sem) | GFP | ChAT | %(Mean ± sem) |
|---|---|---|---|---|---|---|
| P1 Injected | 186 | 300 | 62 ± 1 | 170 | 500 | 34 ± 2 |
| P21 Injected | 23 | 300 | 8 ± 1 | 272 | 500 | 54 ± 3 |
21d Post Injection
|  | GFP | ChAT | %(Mean ± sem) | GFP | ChAT | %(Mean ± sem) |
|---|---|---|---|---|---|---|
| P1 Injected | 227 | 300 | 75 ± 4 | 211 | 500 | 42 ± 2 |
| P21 Injected | 29 | 300 | 10 ± 4 | 305 | 500 | 61 ± 2 |
| P85 Injected | 25 | 300 | 8 ± 2 | 257 | 500 | 51 ± 6 |

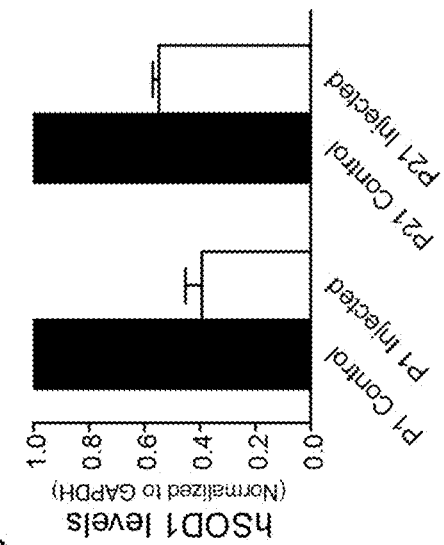
Figure 2B
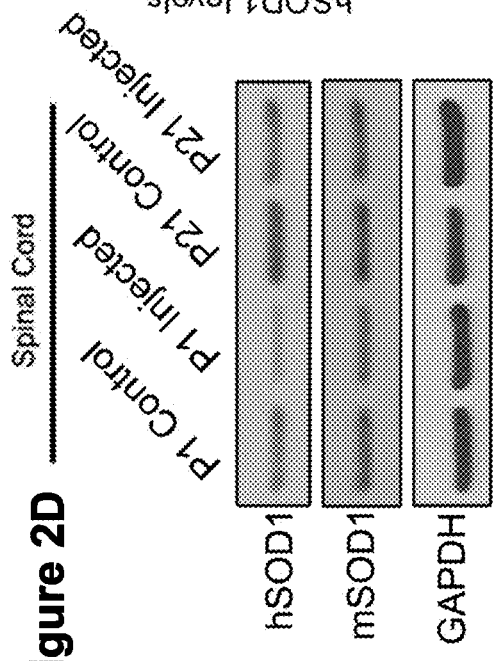
Figure 2D
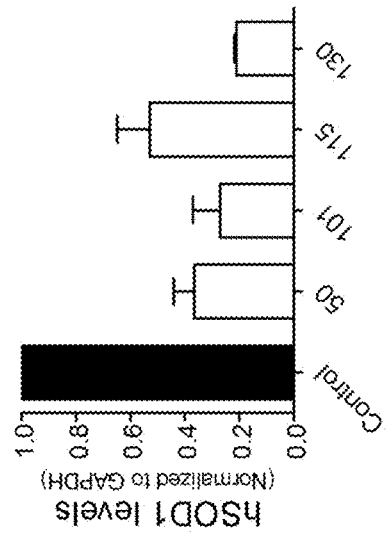
Figure 2E
Figure 2A
```
human  50-GCATCATCAATTTCGAGCAGAAGGAA-75
mouse     .....A.C......C.C.........
human  101-GAAGCATTAAAGGACTGACTGAA-123
mouse      ..CAA......C...T.A......
human  115-CTGACTGAAGGCCTGCATGGATT-137
mouse      .....T.A......A.....G..
human  130-CATGGATTCCATGTTCATGA-149
mouse      ........G....C..C..C
```
Figure 2C

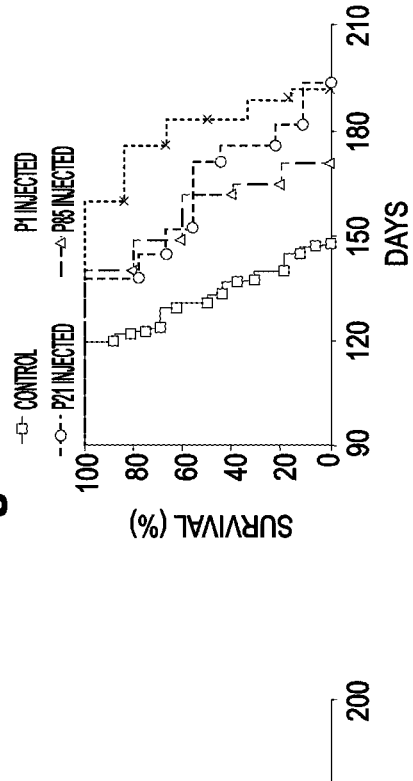
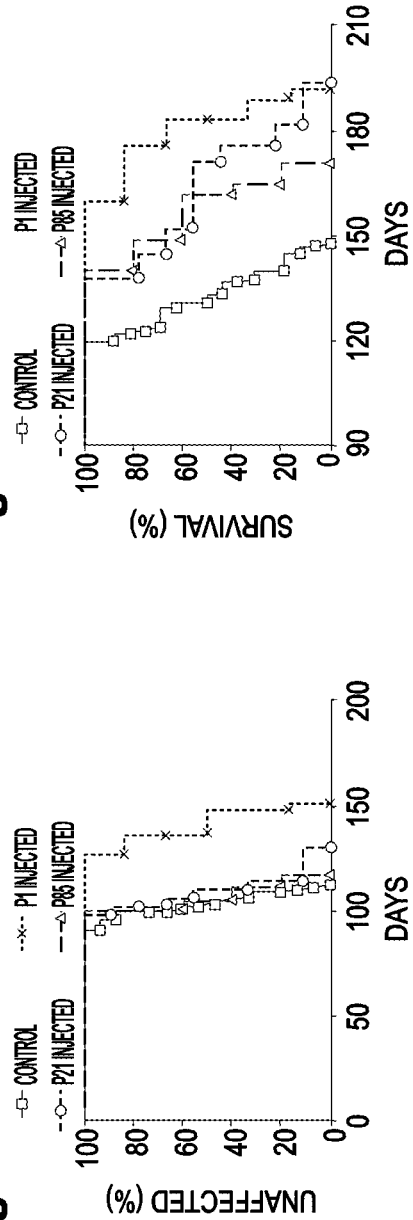
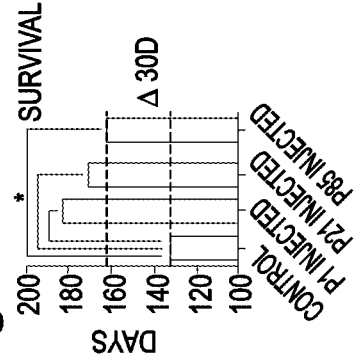
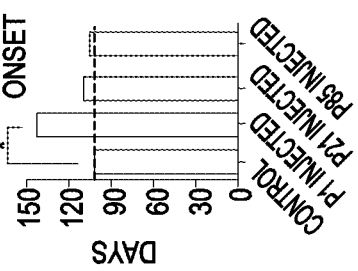

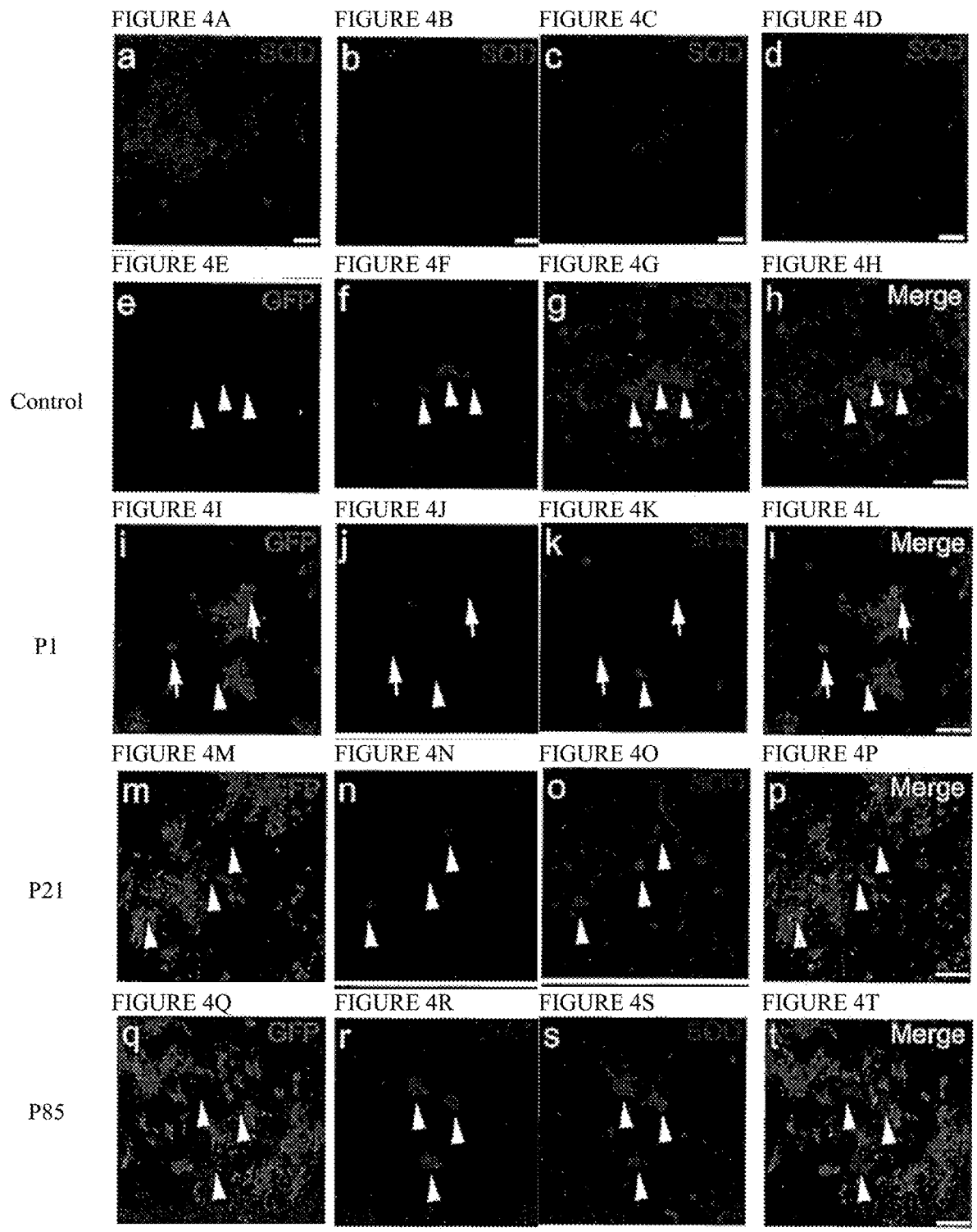

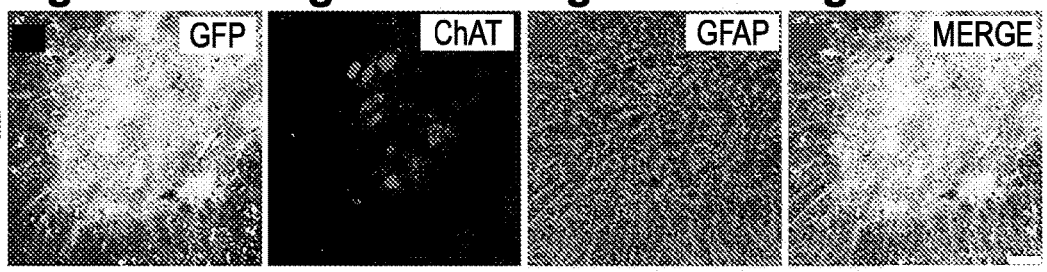
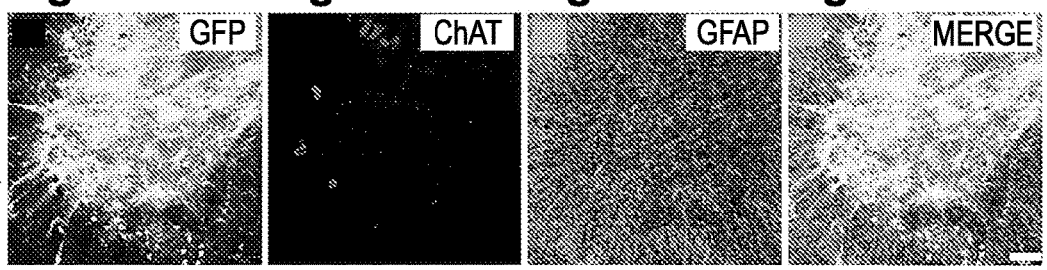
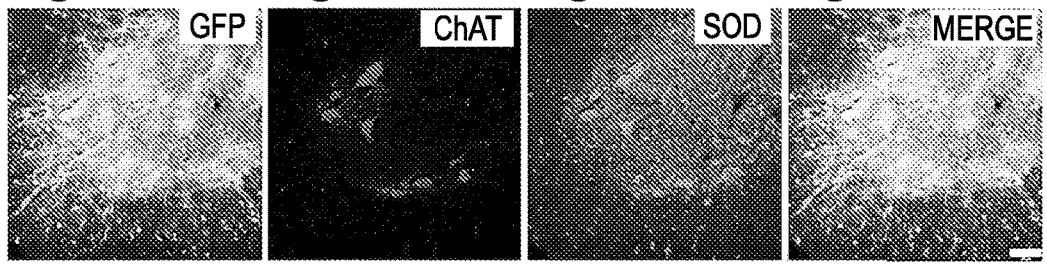
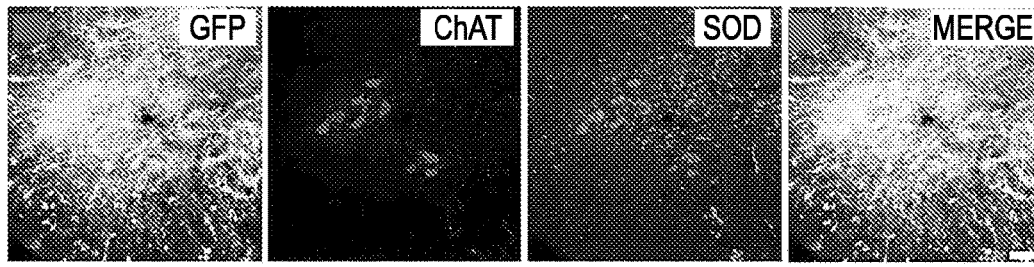

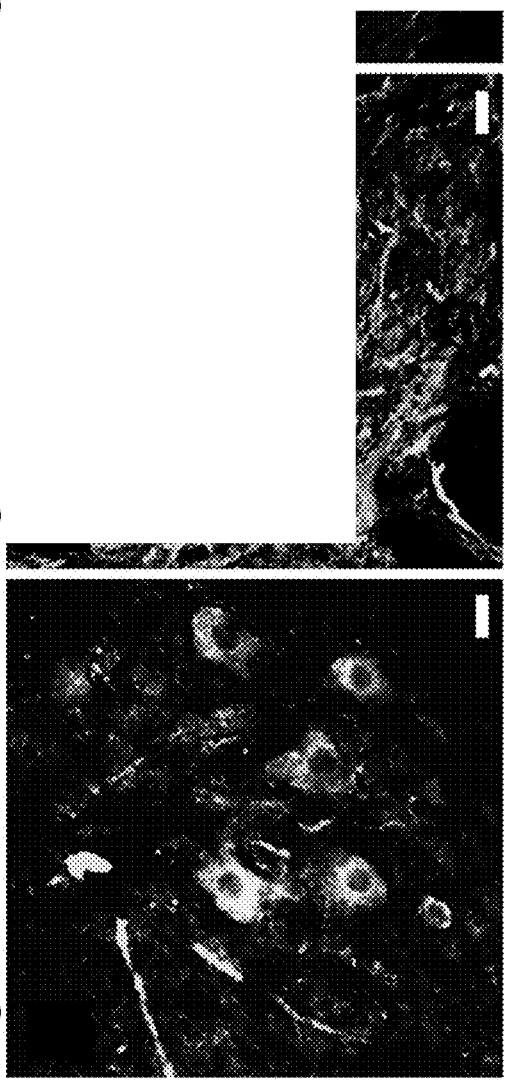
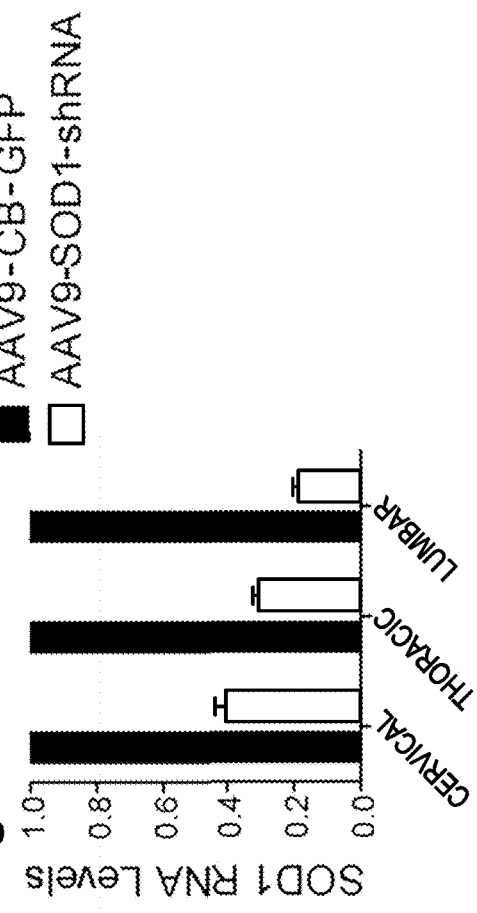
Figure 8A
Figure 8B
Figure 8C
Figure 8D
Figure 8E

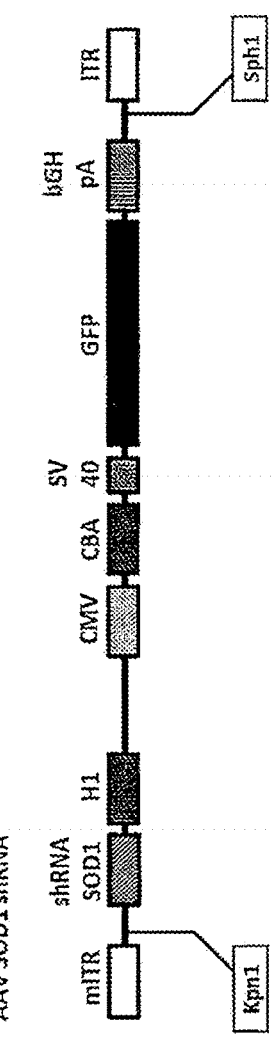
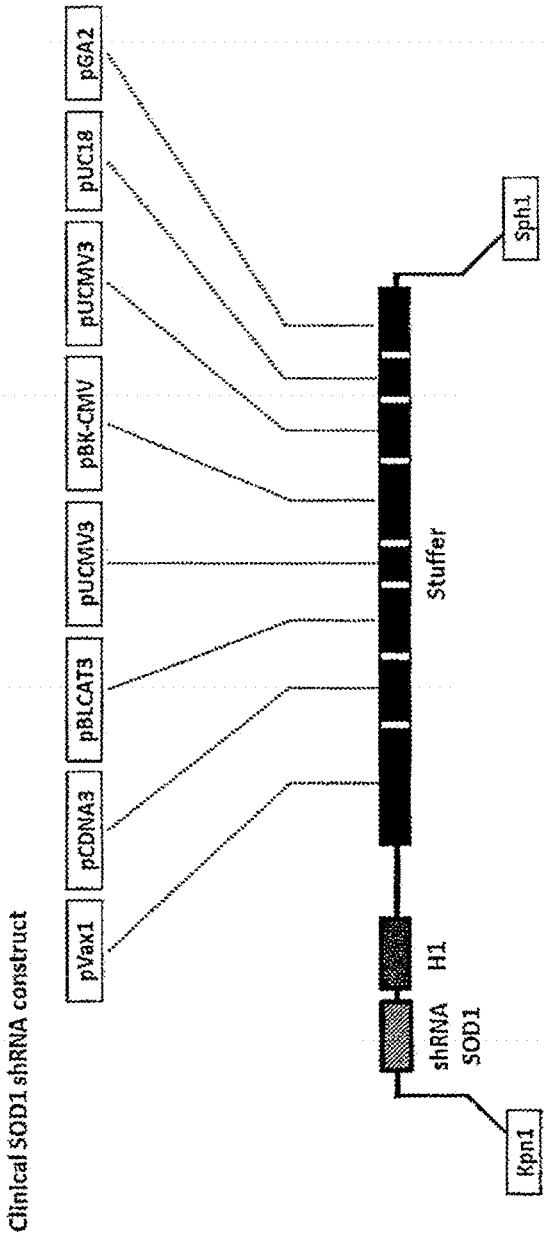
Figure 9A
AAV SOD1 shRNA
Figure 9B
Clinical SOD1 shRNA construct

CONTROL

AAV SOD1 shRNA

CLINICAL AAV SOD1 shRNA

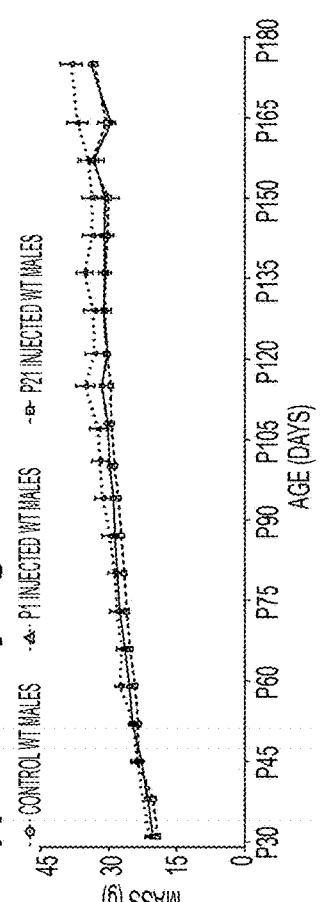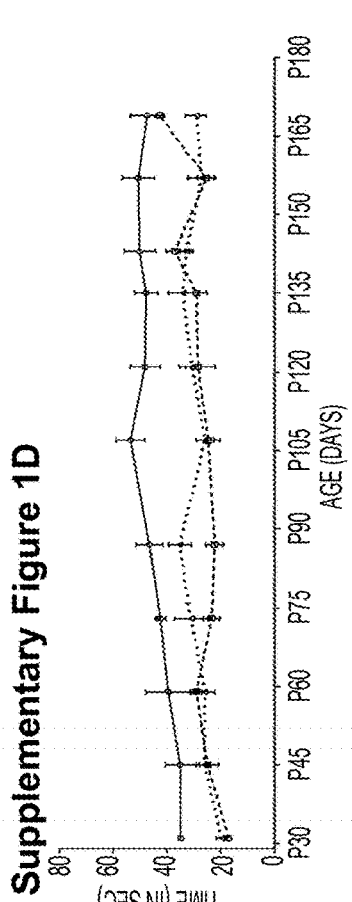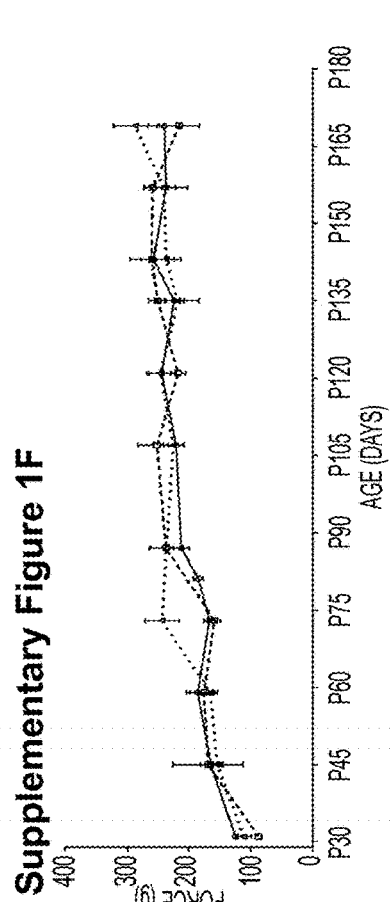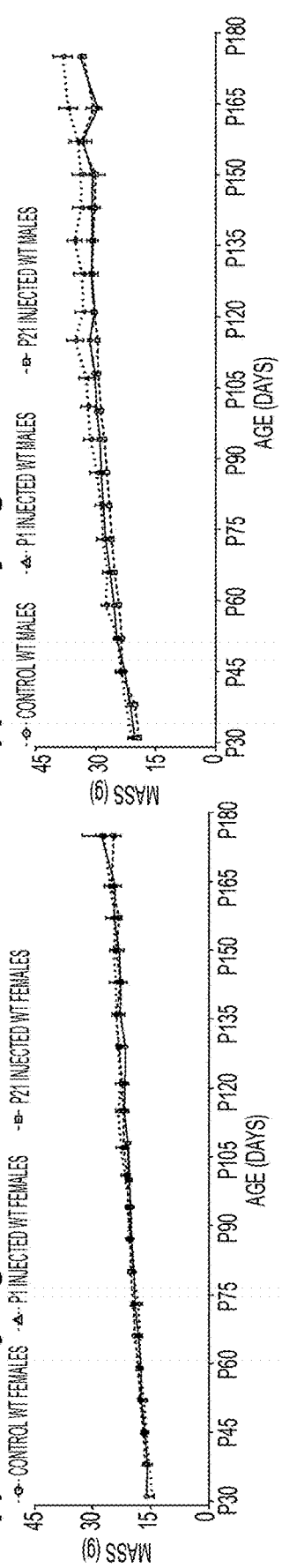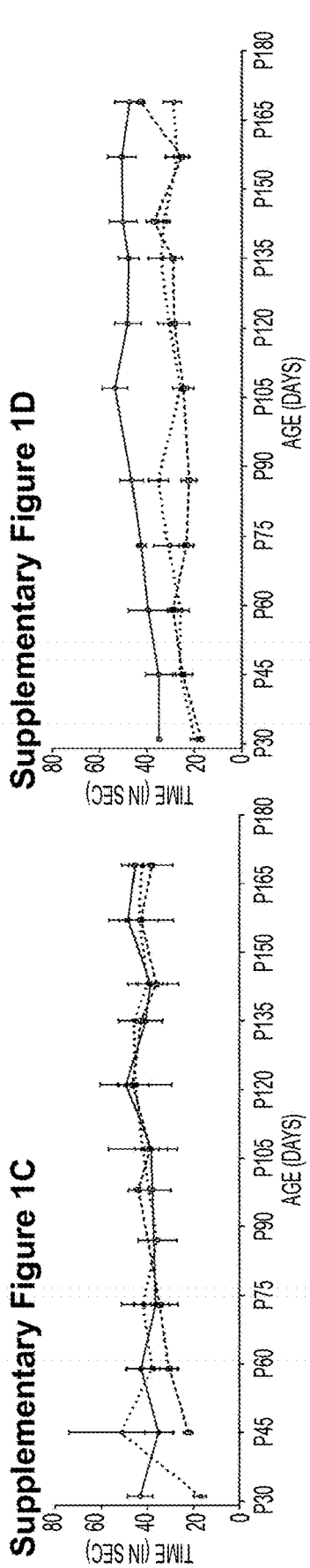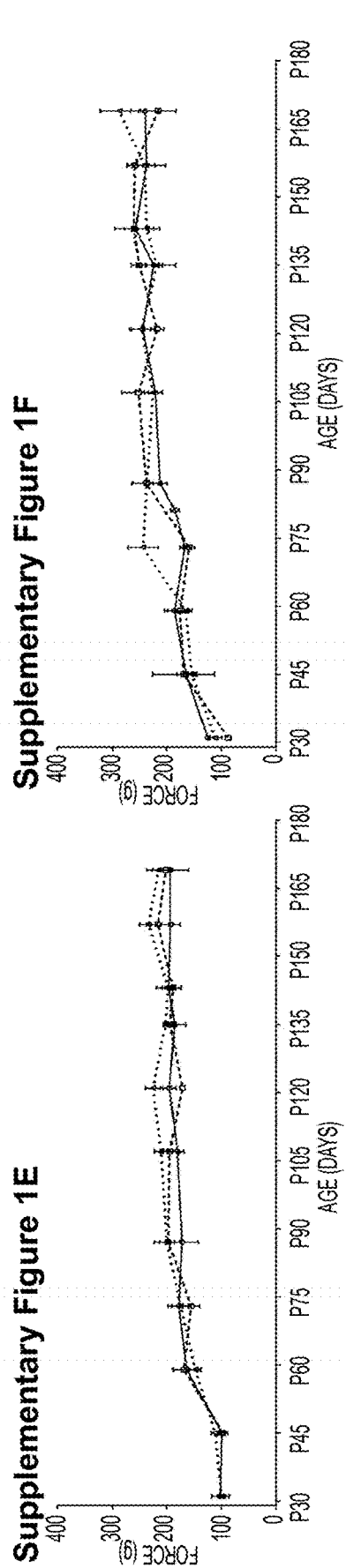

Supplementary Figure 2A
RBC
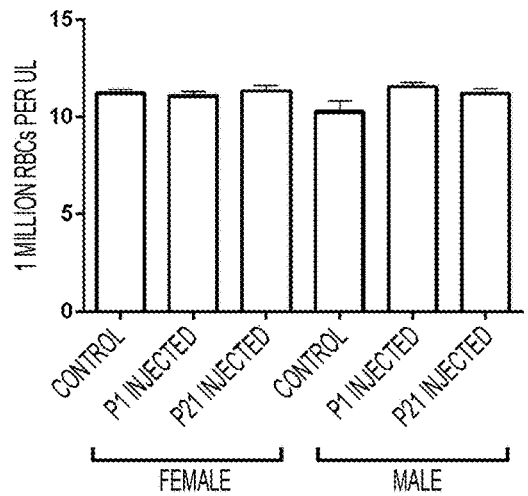
Supplementary Figure 2B
Hemoglobin
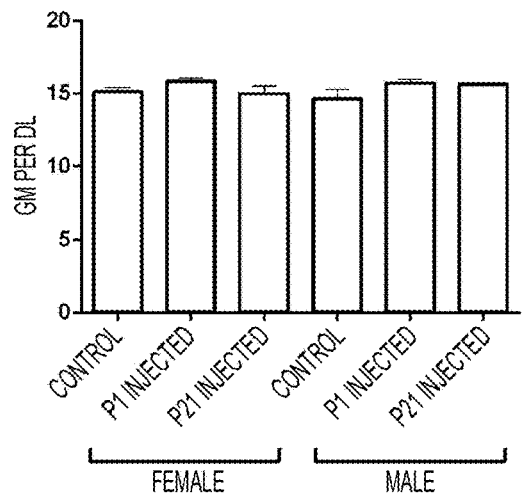
Supplementary Figure 2C
MCV
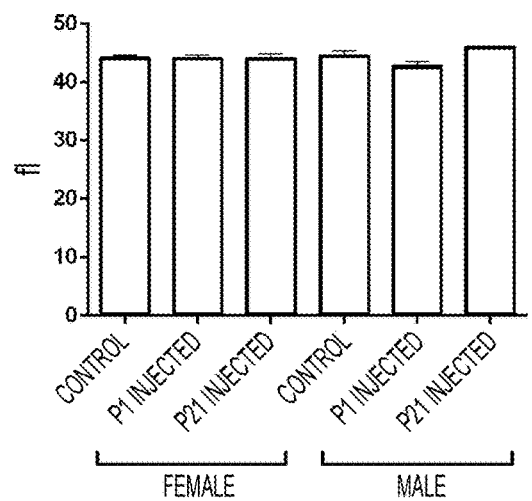
Supplementary Figure 2D
MCH
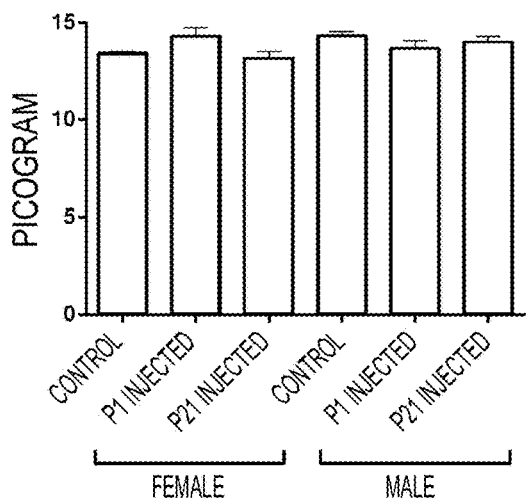
Supplementary Figure 2E
MCHC
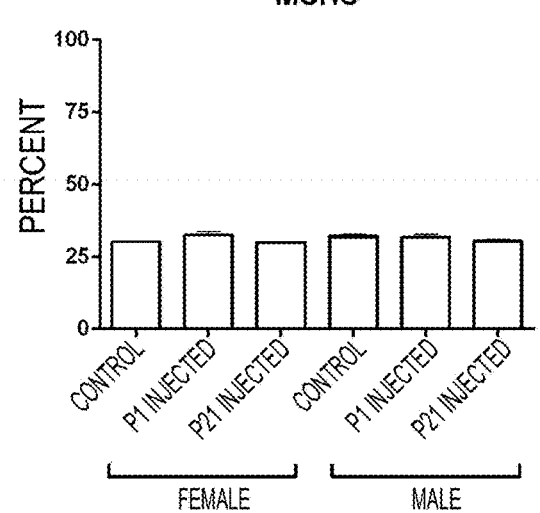
Supplementary Figure 2F
Platelets
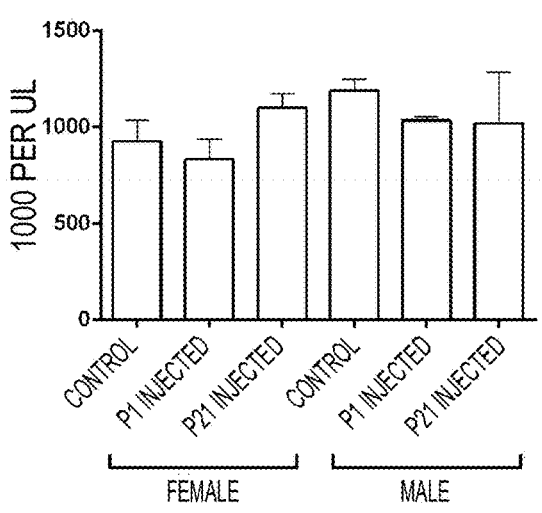

Supplementary Figure 2G
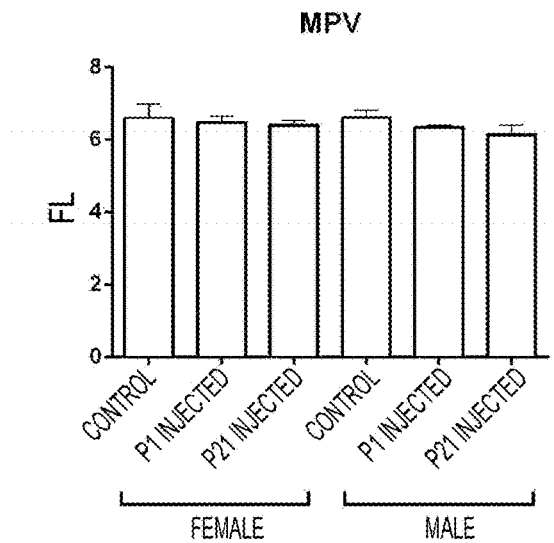
Supplementary Figure 2H
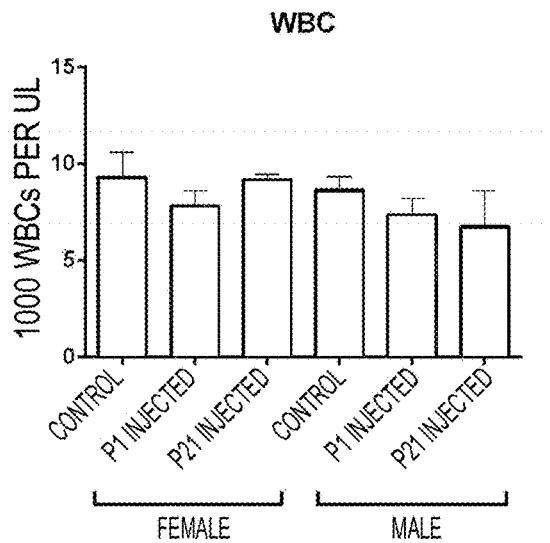
Supplementary Figure 2I
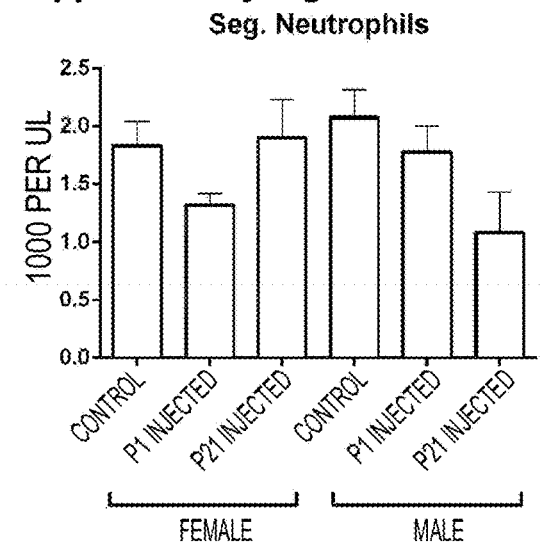
Supplementary Figure 2J
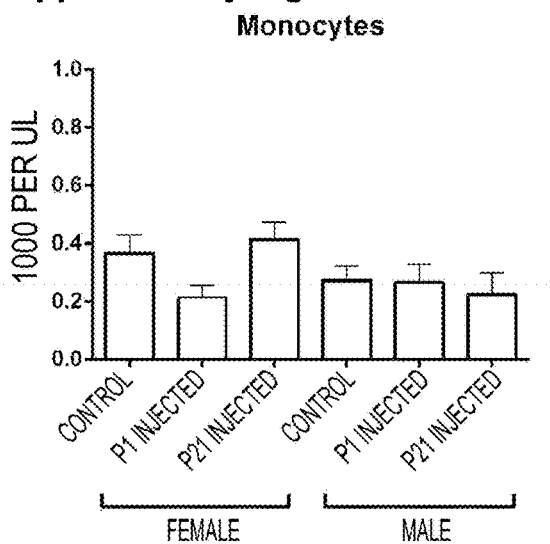
Supplementary Figure 2K
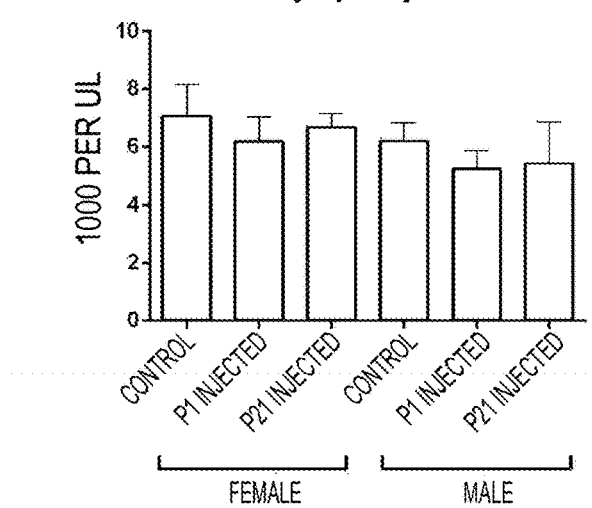
Supplementary Figure 2L
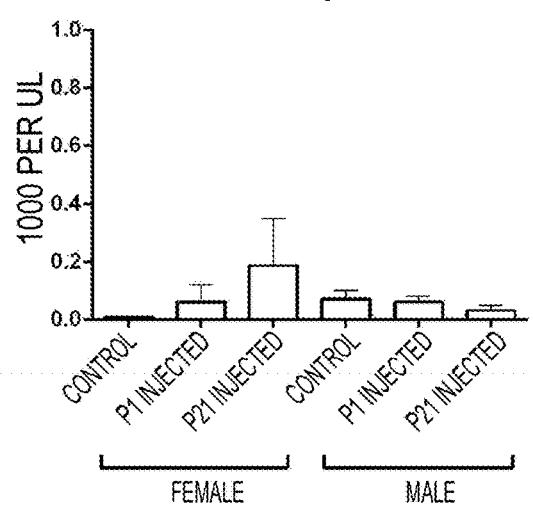

Supplementary Figure 2M
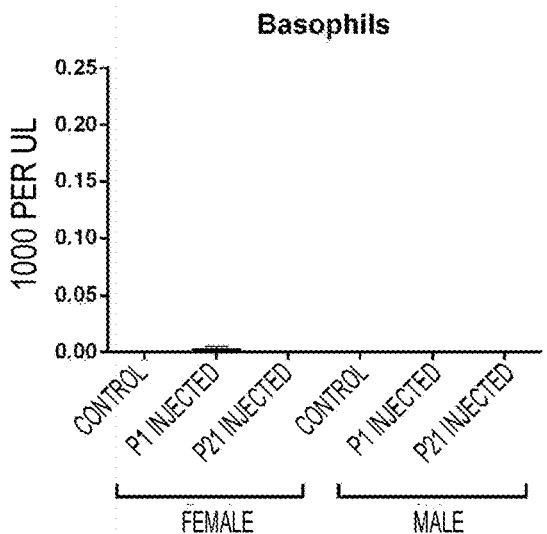
Supplementary Figure 2N
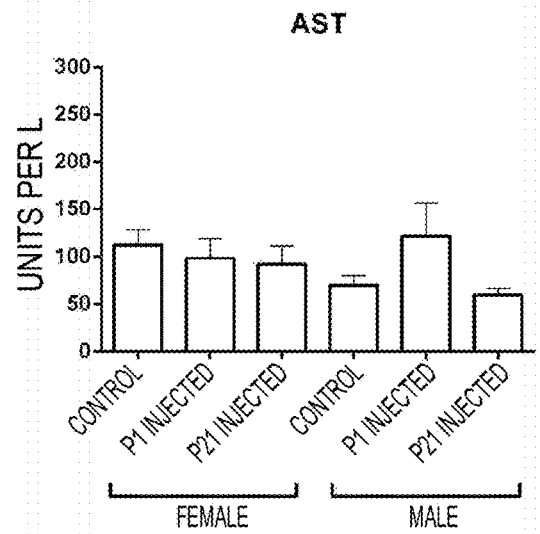
Supplementary Figure 2O
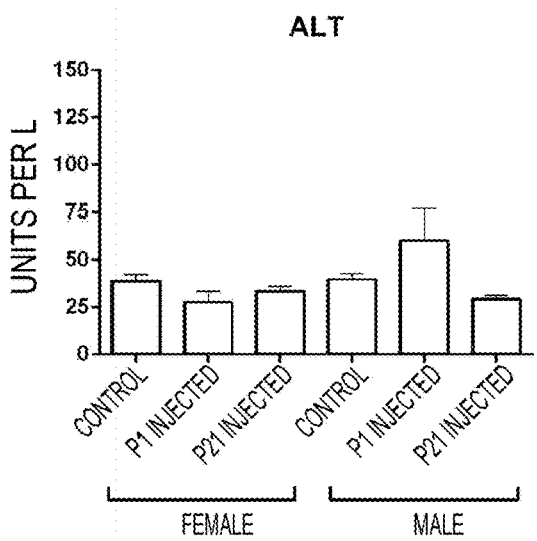
Supplementary Figure 2P
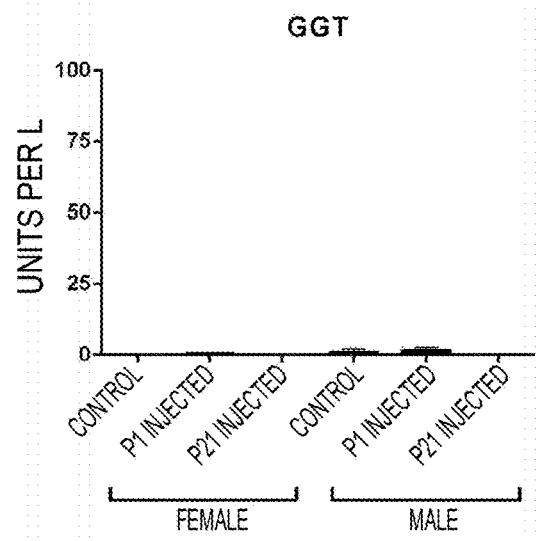
Supplementary Figure 2Q
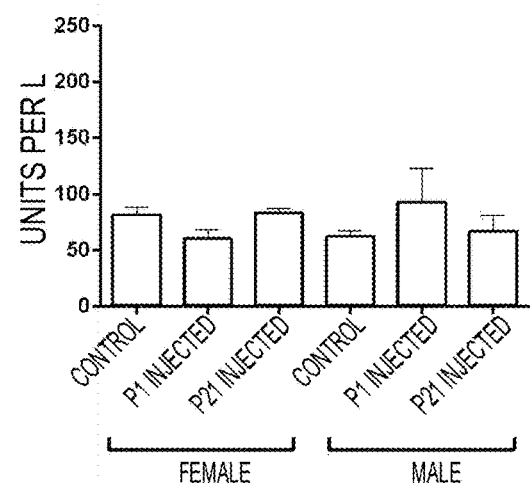
Supplementary Figure 2R
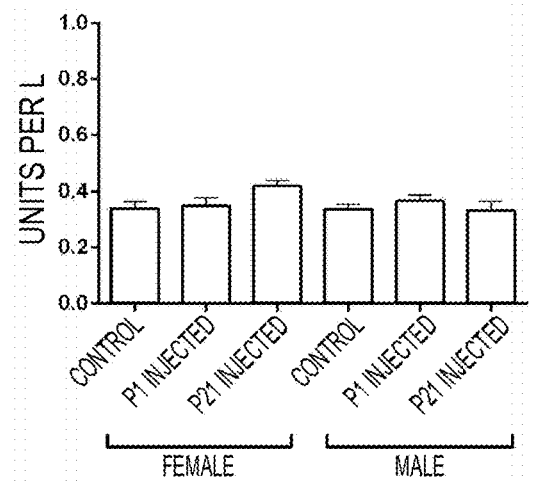

Supplementary Figure 2S
BUN
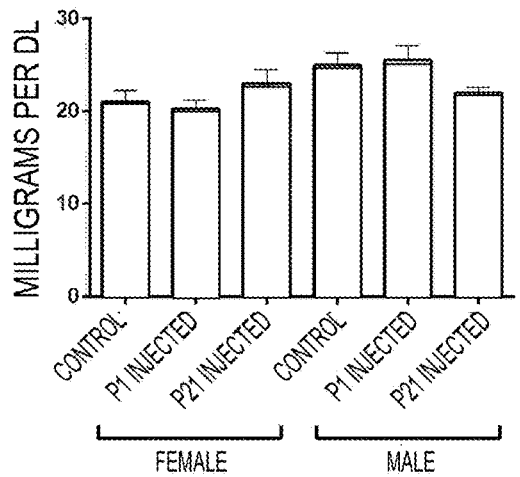
Supplementary Figure 2T
Sodium
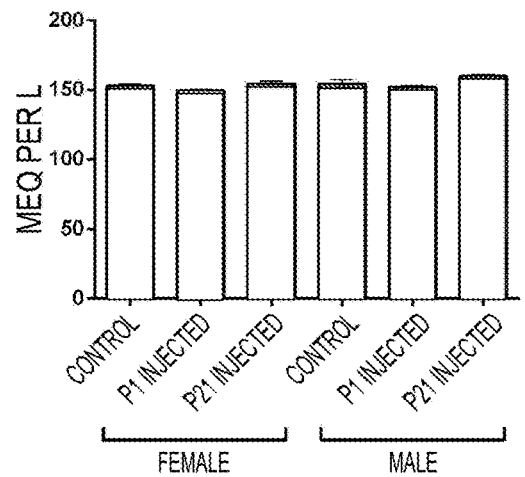
Supplementary Figure 2U
Potassium
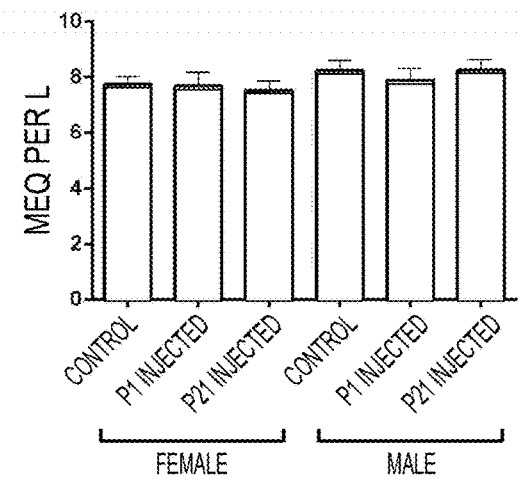
Supplementary Figure 2V
Chloride
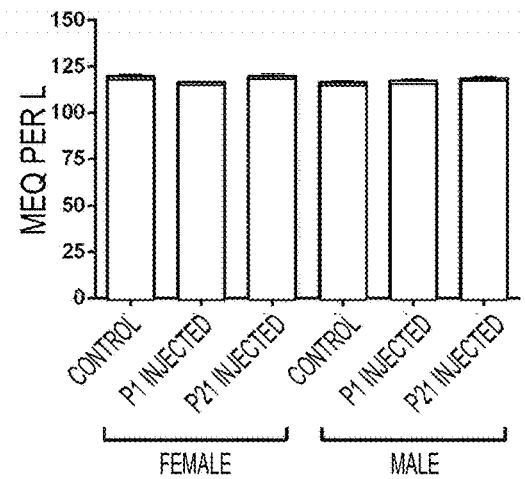
Supplementary Figure 2W
CPK
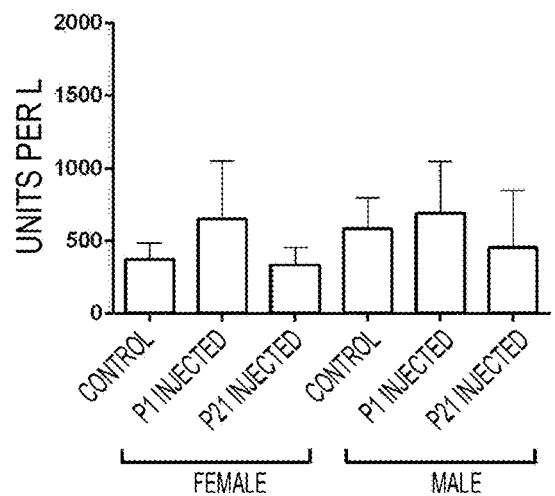

| Supplementary Figure 3A | Supplementary Figure 3B | Supplementary Figure 3C | Supplementary Figure 3D |
|---|---|---|---|
| CONTROL | P1 | P21 | P85 |
GFAP 
| Supplementary Figure 3E | Supplementary Figure 3F | Supplementary Figure 3G | Supplementary Figure 3H |
|---|---|---|---|
| CONTROL | P1 | P21 | P85 |
Iba1 

Supplementary Figure 4A
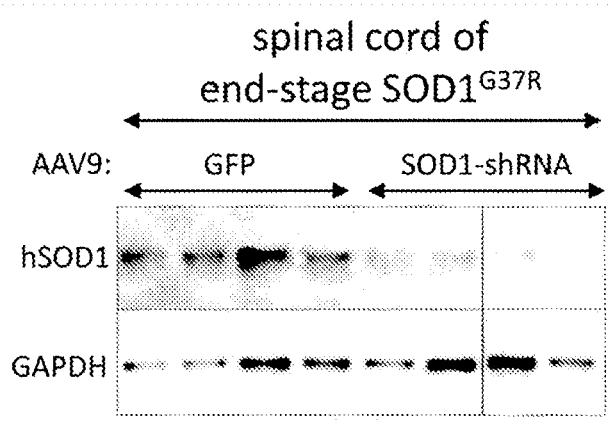
Supplementary Figure 4B
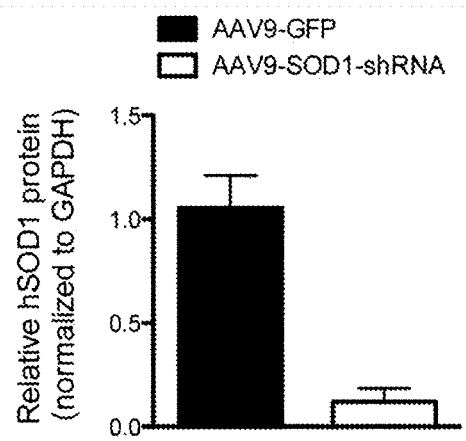

Supplementary Figure 5A
Human 130-CATGGATTCCATGTTCATGA-149
Monkey .....................C.
Supplementary Figure 5B
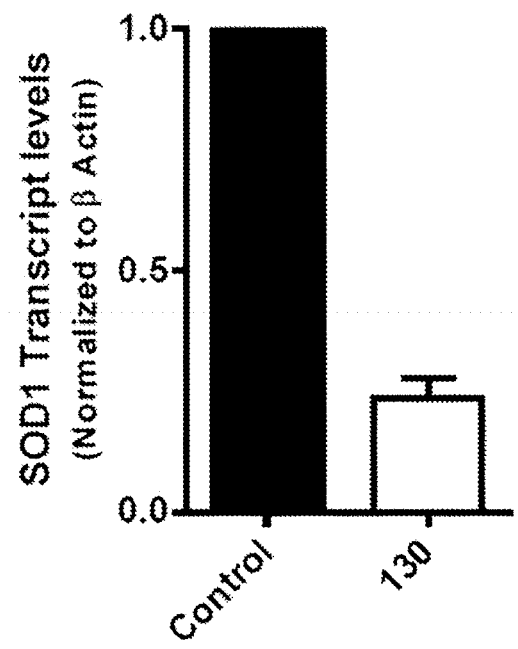

PRODUCTS AND METHODS FOR TREATMENT OF FAMILIAL AMYOTROPHIC LATERAL SCLEROSIS

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 14,350 byte ACII (Text) file named "47886PCT_SeqListing.txt," created on Aug. 26, 2014.

FIELD OF THE INVENTION

The present invention relates to RNA-based methods for inhibiting the expression of the superoxide dismutase 1 (SOD-1) gene. Recombinant adeno-associated viruses of the invention deliver DNAs encoding RNAs that knock down the expression of SOD-1. The methods have application in the treatment of amyotrophic lateral sclerosis (ALS).

The present application is a continuation of U.S. patent application Ser. No. 14/914,861, filed on Feb. 26, 2016, now abandoned, which is a national phase filing of U.S. International Patent Application No. PCT/US14/52753, filed on Aug. 26, 2014, which claims priority benefit of U.S. Provisional Application No, 61/870.585, filed Aug. 27, 2013, all of which are incorporated by reference herein in their entirety.

STATEMENT OF GOVERNMENT INTEREST

This invention was made with government support under U.S. National Institutes of Health R21-NS067238, NS027036, ROI NS064492 and RC2 NS69476-01. The Government has certain rights in the invention.

BACKGROUND

ALS is an adult-onset, rapidly progressive and fatal neurodegenerative disease, characterized by selective degeneration of both upper and lower motor neurons. First characterized by Charcot in 1869, ALS is responsible for one in every 2000 deaths, affecting nearly 5 out of 100,000 individuals. ALS occurs when specific nerve cells in the brain and spinal cord that control voluntary movement degenerate. Within two to five years after clinical onset, the loss of these motor neurons leads to progressive atrophy of skeletal muscles, which results in loss of muscular function resulting in paralysis, speech deficits, and death due to respiratory failure.

Most ALS cases have no clear genetic linkage and are referred to as sporadic, but in 10% of instances disease is familial with dominant inheritance. Twenty percent of familial cases are caused by mutations in the enzyme superoxide dismutase 1 (SOD1), with over 140 distinct mutations identified to date[1,2]. Many efforts to identify how mutations alter the function of SOD1 have produced a consensus view that SOD1 mutants acquire one or more toxicities, whose nature still remains controversial[3], but there is clear evidence that a proportion of mutant SOD1 is misfolded and subsequently aggregates[4,5]. SOD1 aggregates are, in fact, one of the histological hallmarks of SOD1-related ALS cases[4].

In the past 20 years, multiple animal models expressing mutant forms of human SOD1 have been generated. These models recapitulate the hallmarks of ALS, developing age-dependent motor axon degeneration and accompanying muscle denervation, glial inflammation and subsequent motor neuron loss. Selective gene excision experiments have determined that mutant SOD1 expression within motor neurons themselves contributes to disease onset and early disease progression[6], as does mutant synthesis in NG2+ cells[7] that are precursors to oligodendrocytes. However, mutant SOD1 protein expression in microglia and astrocytes significantly drives rapid disease progression[6,8], findings which have lead to the conclusion that ALS pathophysiology is non-cell autonomous[3].

Further, astrocytes have been found to be toxic to motor neurons in multiple in vitro models where mutant forms of human SOD1 were overexpressed[9-11]. A recent study derived astrocytes from post-mortem spinal cords of ALS patients with or without SOD1 mutations. In all cases, astrocytes from sporadic ALS patients were as toxic to motor neurons as astrocytes carrying genetic mutations in SOD1[12]. Even more strikingly, reduction of SOD1 in astrocytes derived from both sporadic and familial ALS patients decreased astrocyte-derived toxicity that is selective for motor, but not GABA, neurons. This remarkable finding, along with reports that misfolded SOD1 inclusions are found in the spinal cords of familial as well as some sporadic ALS patients[13,14,15], has provided strong evidence for a pathogenic role of wild-type SOD1 in sporadic ALS.

Despite the insights that SOD1 mutant-expressing animal models have provided for understanding mechanisms involved in motor neuron degeneration, their utility for the development of therapeutic approaches has been questioned[16], as no drug with a reported survival benefit in mutant SOD1$^{G93A}$ mice has been effective in clinical trials with sporadic ALS patients. In all but one case the drugs taken to human trial had been reported only to extend mutant SOD1 mouse survival when applied presymptomatically, and even then to provide a survival benefit solely by delaying disease onset with no benefit in slowing disease progression. The one exception to this was riluzole, which like the human situation, modestly extended survival of mutant SOD1$^{G93A}$ mice and did so by slowing disease progression[17]. Recognizing that success at human trial will require slowing of disease progression, the SOD1 mutant mice have perfectly predicted the success of riluzole and the failure of efficacy of each other drug attempted in human trial. What has been missing are additional therapies that affect disease progression in these mice.

Thus, riluzole is the only drug currently approved by the FDA as a therapy for ALS, providing a modest survival benefit[21]. For the 20% of familial cases caused by mutation in SOD1, attempts at improving therapy by reducing synthesis of SOD1 have been the focus of multiple therapeutic development approaches. Antisense oligonucleotides and viral delivered RNA interference (RNAi) were tested in rat[22] and mouse models[23-25] that develop fatal paralysis from overexpressing human SOD1$^{G93A}$. Antisense oligonucleotides infused at disease onset produced SOD1 reduction and a modest slowing of disease progression[22]. Direct CSF infusion of antisense oligonucleotides has been tested clinically[26], leading to encouraging results in terms of tolerability and safety, but without significant reduction in SOD1 levels at the low dosages utilized. In each of the prior viral studies[23-25], SOD1 knockdown was achieved before disease onset by direct injection into the nervous system or taking advantage of axonal retrograde transport when a virus was injected intramusculary[23,24]. These studies led to varying degrees of success in extending survival or improving motor performance, depending on the time of treatment as well as level of SOD1 knockdown achieved in the spinal cord. Although these studies provided important proof of principle, the approaches were far from being readily translated into clinical strategies. Indeed, there have been controversial reports surrounding these initial viral mediated SOD1 suppression studies[23,24,27-29].

Adeno-associated virus (AAV) vectors have been used in a number of recent clinical trials for treatment of neurological disorders [Kaplitt et al., *Lancet* 369: 2097-2105 (2007); Marks et al., *Lancet Neurol* 7: 400-408 (2008); Worgall et al., *Hum Gene Ther* (2008)].

AAV is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication (rep), encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10, AAV11 and AAVrh74. Advances in the delivery of AAV6 and AAV8 have made possible the transduction by these serotypes of skeletal and cardiac muscle following simple systemic intravenous or intraperitoneal injections. See Pacak et al., *Circ. Res.*, 99(4): 3-9 (1006) and Wang et al., *Nature Biotech.*, 23(3): 321-8 (2005). The use of AAV to target cell types within the central nervous system has involved surgical intraparenchymal injection. See, Kaplitt et al., supra; Marks et al., supra and Worgall et al., supra. Regarding the use of AAV to target cell types within the nervous system, see International Publication No. WO 2010/071832. International Publication Nos. WO 2009/043936 and WO 2009/013290 state they relate to delivering genes to the central nervous system. International Publication No. WO 2011/133890 states it relates to recombinant adeno-associated viruses useful for targeting transgenes to central nervous system tissue.

There thus remains a need in the art for methods and materials for treatment of ALS.

SUMMARY

The present invention provides products and methods useful for reducing mutant SOD1 protein levels in subjects in need thereof. The invention provides AAV-mediated delivery of RNAs including, but not limited to short hairpin RNAs, to reduce synthesis of ALS-causing human SOD1 mutants in subjects in need thereof. Recombinant AAV (rAAV) contemplated by the invention include, but are not limited to, rAAV9, rAAV2 and rAAVrh74. Delivery routes contemplated by the invention include, but are not limited to, systemic delivery and intrathecal delivery. Use of the methods and products of the invention is indicated, for example, in treating ALS.

DETAILED DESCRIPTION

In one aspect, the invention provides rAAV genomes comprising one or more AAV ITRs flanking a polynucleotide encoding one or more RNAs (including, but not limited to, small hairpin RNAs, antisense RNAs and/or microRNAs) that target mutant SOD1 polynucleotides. The examples describe the use of exemplary rAAV encoding small hairpin RNAs (shRNAs). In the rAAV genomes, the shRNA-encoding polynucleotide is operatively linked to transcriptional control DNA, specifically promoter DNA that is functional in target cells. Commercial providers such as Ambion Inc. (Austin, Tex.), Darmacon Inc. (Lafayette, Colo.), InvivoGen (San Diego, Calif.), and Molecular Research Laboratories, LLC (Herndon, Va.) generate custom inhibitory RNA molecules. In addition, commercially kits are available to produce custom siRNA molecules, such as SILENCER™ siRNA Construction Kit (Ambion Inc., Austin, Tex.) or psiRNA System (InvivoGen, San Diego, Calif.). In some embodiments, the rAAV genome comprises a DNA encoding a SOD1 shRNA such as:

```
                                       (SEQ ID NO: 1)
GCATCATCAATTTCGAGCAGAAGGAA, (SEQ ID NO: 2)
GAAGCATTAAAGGACTGACTGAA, (SEQ ID NO: 3)
CTGACTGAAGGCCTGCATGGATT, (SEQ ID NO: 4)
CATGGATTCCATGTTCATGA
("shRNA 130" or "SOD1 shRNA" herein), (SEQ ID NO: 5)
GCATGGATTCCATGTTCATGA, (SEQ ID NO: 6)
GGTCTGGCCTATAAAGTAGTC, (SEQ ID NO: 7)
GGGCATCATCAATTTCGAGCA,
```

GCATCATCAATTTCGAGCAGA, (SEQ ID NO: 8)

GCCTGCATGGATTCCATGTTC, (SEQ ID NO: 9)

GGAGGTCTGGCCTATAAAGTA, (SEQ ID NO: 10)

GATTCCATGTTCATGAGTTTG, (SEQ ID NO: 11)

GGAGATAATACAGCAGGCTGT, (SEQ ID NO: 12)

GCTTTAAAGTACCTGTAGTGA, (SEQ ID NO: 13)

GCATTAAAGGACTGACTGAAG, (SEQ ID NO: 14)

GCATCATCAATTTCGAGCAGAAGGAA, (SEQ ID NO: 1)

GAAGCATTAAAGGACTGACTGAA, (SEQ ID NO: 2)

CTGACTGAAGGCCTGCATGGATT, (SEQ ID NO: 3)

CATGGATTCCATGTTCATGA, (SEQ ID NO: 4)

GCATGGATTCCATGTTCATGA, (SEQ ID NO: 5)

GGTCTGGCCTATAAAGTAGTC, (SEQ ID NO: 6)

GGGCATCATCAATTTCGAGCA, (SEQ ID NO: 7)

GCATCATCAATTTCGAGCAGA, (SEQ ID NO: 8)

GCCTGCATGGATTCCATGTTC, (SEQ ID NO: 9)

GGAGGTCTGGCCTATAAAGTA, (SEQ ID NO: 10)

GATTCCATGTTCATGAGTTTG, (SEQ ID NO: 11)

GGAGATAATACAGCAGGCTGT, (SEQ ID NO: 12)

GCTTTAAAGTACCTGTAGTGA, (SEQ ID NO: 13)

GCATTAAAGGACTGACTGAAG, (SEQ ID NO: 14)

TCATCAATTTCGAGCAGAA, (SEQ ID NO: 15)

TCGAGCAGAAGGAAAGTAA, (SEQ ID NO: 16)

GCCTGCATGGATTCCATGT, (SEQ ID NO: 17)

TCACTCTCAGGAGACCATT, or (SEQ ID NO: 18)

GCTTTAAAGTACCTGTAGT. (SEQ ID NO: 19)

The rAAV genomes of the invention lack AAV rep and cap DNA. AAV DNA in the rAAV genomes (e.g., ITRs) may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. The nucleotide sequences of the genomes of the AAV serotypes are known in the art. For example, the complete genome of AAV-1 is provided in GenBank Accession No. NC_002077; the complete genome of AAV-2 is provided in GenBank Accession No. NC 001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The AAVrh74 genome is provided in International Publication No. WO 2013/078316.

In another aspect, the invention provides DNA plasmids comprising rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety. In various embodiments, AAV capsid proteins may be modified to enhance delivery of the recombinant vector. Modifications to capsid proteins are generally known in the art. See, for example, US 20050053922 and US 20090202490, the disclosures of which are incorporated by reference herein in their entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. Single-stranded rAAV are specifically contemplated. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

In still another aspect, the invention provides rAAV (i.e., infectious encapsidated rAAV particles) comprising a rAAV genome of the invention. In some embodiments, the rAAV genome is a self-complementary genome. The genomes of the rAAV lack AAV rep and cap DNA, that is, there is no AAV rep or cap DNA between the ITRs of the genomes. Embodiments include, but are not limited to, the exemplary rAAV including a genome encoding the SOD1 shRNA named "AAV-SOD1-shRNA." A sequence including the AAV-SOD1-shRNA genome is set out below as an inverted sequence from a plasmid used in production.

```
FEATURES       Location/Qualifiers
   misc_feature   662..767
                  /gene="mutated ITR"
                  /SECDrawAs="Region"
                  /SECStyleId=1
   CDS            complement(901..965)
                  /gene="SOD shRNA"
                  /SECDrawAs="Gene"
                  /SECStyleId=1
   misc_feature   complement(966..1064)
                  /gene="H1"
                  /SECDrawAs="Region"
                  /SECStyleId=1
   misc_feature   1224..1503
                  /gene="CMV enhancer"
                  /SECDrawAs="Region"
                  /SECStyleId=1
   misc_feature   1510..1779
                  /gene="B-Actin promoter"
                  /product="Chicken"
                  /SECDrawAs="Region"
                  /SECStyleId=1
   misc_feature   1845..1875
                  /gene="SV40_late_19s_int"
                  /SECDrawAs="Region"
                  /SECStyleId=1
   misc_feature   1845..1941
                  /gene="modSV40_late_16s_int"
                  /SECDrawAs="Region"
                  /SECStyleId=1
   CDS            2015..2734
                  /gene="GFP"
                  /SECDrawAs="Gene"
                  /SECStyleId=1
   misc_feature   2783..2929
                  /gene="BGHpA"
                  /SECDrawAs="Region"
                  /SECStyleId=1
   misc_feature   3009..3149
                  /gene="ITR"
                  /SECDrawAs="Region"
                  /SECStyleId=1
   misc_feature   3983..4843
                  /gene="amp r"
                  /SECDrawAs="Region"
                  /SECStyleId=1
   misc_feature   4997..5618
                  /gene="pBR322 ori"
                  /SECDrawAs="Region"
                  /SECStyleId=1
```

(SEQ ID NO: 20)

```
  1 gcccaatacg caaaccgcct ctccccgcgc gttggccgat tcattaatgc agctgattct 61 aacgaggaaa gcacgttata cgtgctcgtc aaagcaacca tagtacgcgc cctgtagcgg 121 cgcattaagc gcggcgggtg tggtggttac gcgcagcgtg accgctacac ttgccagcgc 181 cctagcgccc gctcctttcg ctttcttccc ttcctttctc gccacgttcg ccggctttcc 241 ccgtcaagct ctaaatcggg ggctcccttt agggttccga tttagtgctt tacggcacct 301 cgaccccaaa aaacttgatt agggtgatgg ttcacgtagt gggccatcgc cctgatagac 361 ggtttttcgc cctttgacgt tggagtccac gttctttaat agtggactct tgttccaaac 421 tggaacaaca ctcaaccta tctcggtcta ttcttttgat ttataaggga ttttgccgat 481 ttcggcctat tggttaaaaa atgagctgat ttaacaaaaa tttaacgcga attttaacaa 541 aatattaacg cttacaattt aaatatttgc ttatacaatc ttcctgtttt tggggctttt 601 ctgattatca accggggtac atatgattga catgctagtt ttacgattac cgttcatcgc
```

-continued

```
 661 cctgcgcgct cgctcgctca ctgaggccgc ccgggcaaag cccgggcgtc gggcgacctt
 721 tggtcgcccg gcctcagtga gcgagcgagc gcgcagagag ggagtggaat tcacgcgtgg
 781 atctgaattc aattcacgcg tggtacctac actttatgct tccggctcgt atgttgtgtg
 841 gaattgtgag cggataacaa tttcacacag gaaacagcta tgaccatgat tacgccaagc
 901 tttccaaaaa agcatggatt ccatgttcat gatctcttga atcatgaaca tggaatccat
 961 ggatccgagt ggtctcatac agaacttata agattcccaa atccaaagac atttcacgtt
1021 tatggtgatt tcccagaaca catagcgaca tgcaaatatg aattcactgg ccgtcgtttt
1081 acaacgtcgt gactgggaaa accctggcgt tacccaactt aatcgccttg cagcacatcc
1141 ccctttcgcc agctggcgta atagcgaaga ggcccgcacc gatcgccctt cccaacagtt
1201 gcgcagcctg tggtacctct ggtcgttaca taacttacgg taaatggccc gcctggctga
1261 ccgcccaacg acccccgccc attgacgtca ataatgacgt atgttcccat agtaacgcca
1321 atagggactt tccattgacg tcaatgggtg gagtatttac ggtaaactgc ccacttggca
1381 gtacatcaag tgtatcatat gccaagtacg ccccctattg acgtcaatga cggtaaatgg
1441 cccgcctggc attatgccca gtacatgacc ttatgggact ttcctacttg gcagtacatc
1501 tactcgaggc cacgttctgc ttcactctcc ccatctcccc cccctcccca ccccaatttt
1561 tgtatttatt tattttttaa ttattttgtg cagcgatggg ggcggggggg ggggggggc
1621 gcgcgccagg cggggcgggg cgggcgaggg ggcggggcgg ggcgaggcgg agaggtgcgg
1681 cggcagccaa tcagagcggc gcgctccgaa agtttccttt tatggcgagg cggcggcggc
1741 ggcggcccta taaaaagcga agcgcgcggc gggcgggagc gggatcagcc accgcggtgg
1801 cggcctagag tcgacgagga actgaaaaac cagaaagtta actggtaagt ttagtctttt
1861 tgtcttttat ttcaggtccc ggatccggtg gtggtgcaaa tcaaagaact gctcctcagt
1921 ggatgttgcc tttacttcta ggcctgtacg gaagtgttac ttctgctcta aaagctgcgg
1981 aattgtaccc gcggccgatc caccggtcgc caccatggtg agcaagggcg aggagctgtt
2041 caccggggtg gtgcccatcc tggtcgagct ggacggcgac gtaaacggcc acaagttcag
2101 cgtgtccggc gagggcgagg gcgatgccac ctacggcaag ctgaccctga agttcatctg
2161 caccaccggc aagctgcccg tgccctggcc caccctcgtg accaccctga cctacggcgt
2221 gcagtgcttc agccgctacc ccgaccacat gaagcagcac gacttcttca gtccgccat
2281 gcccgaaggc tacgtccagg agcgcaccat cttcttcaag gacgacggca actacaagac
2341 ccgcgccgag gtgaagttcg agggcgacac cctggtgaac cgcatcgagc tgaagggcat
2401 cgacttcaag gaggacggca acatcctggg gcacaagctg gagtacaact acaacagcca
2461 caacgtctat atcatggccg acaagcagaa gaacggcatc aaggtgaact tcaagatccg
2521 ccacaacatc gaggacggca gcgtgcagct cgccgaccac taccagcaga cacccccat
2581 cggcgacggc cccgtgctgc tgcccgacaa ccactacctg agcacccagt ccgccctgag
2641 caaagacccc aacgagaagc gcgatcacat ggtcctgctg gagttcgtga ccgccgccgg
2701 gatcactctc ggcatggacg agctgtacaa gtaaagcggc catcaagctt atcgataccg
2761 tcgactagag ctcgctgatc agcctcgact gtgccttcta gttgccagcc atctgttgtt
2821 tgcccctccc ccgtgccttc cttgaccctg gaaggtgcca ctcccactgt cctttcctaa
2881 taaaatgagg aaattgcatc gcattgtctg agtaggtgtc attctattct ggggggtggg
2941 gtggggcagg acagcaaggg ggaggattgg gaagacaata gcaggcatgc tggggagaga
3001 tcgatctgag gaaccctag tgatggagtt ggccactccc tctctgcgcg ctcgctcgct
3061 cactgaggcc gggcgaccaa aggtcgcccg acgcccgggc tttgcccggg cggcctcagt
```

```
3121 gagcgagcga gcgcgcagag agggagtggc cccccccccc ccccccccgg cgattctctt
3181 gtttgctcca gactctcagg caatgacctg atagcctttg tagagacctc tcaaaaatag
3241 ctaccctctc cggcatgaat ttatcagcta gaacggttga atatcatatt gatggtgatt
3301 tgactgtctc cggcctttct cacccgtttg aatctttacc tacacattac tcaggcattg
3361 catttaaaat atatgagggt tctaaaaatt tttatccttg cgttgaaata aaggcttctc
3421 ccgcaaaagt attacagggt cataatgttt ttggtacaac cgatttagct ttatgctctg
3481 aggctttatt gcttaatttt gctaattctt tgccttgcct gtatgattta ttggatgttg
3541 gaatcgcctg atgcggtatt ttctccttac gcatctgtgc ggtatttcac accgcatatg
3601 gtgcactctc agtacaatct gctctgatgc cgcatagtta agccagcccc gacacccgcc
3661 aacacccgct gacgcgccct gacgggcttg tctgctcccg gcatccgctt acagacaagc
3721 tgtgaccgtc tccgggagct gcatgtgtca gaggttttca ccgtcatcac cgaaacgcgc
3781 gagacgaaag ggcctcgtga tacgcctatt tttataggtt aatgtcatga taataatggt
3841 ttcttagacg tcaggtggca cttttcgggg aaatgtgcgc ggaaccccta tttgtttatt
3901 tttctaaata cattcaaata tgtatccgct catgagacaa taaccctgat aaatgcttca
3961 ataatattga aaaggaaga gtatgagtat tcaacatttc cgtgtcgccc ttattccctt
4021 ttttgcggca ttttgccttc ctgttttttgc tcacccagaa acgctggtga agtaaaaga
4081 tgctgaagat cagttgggtg cacgagtggg ttacatcgaa ctggatctca acagcggtaa
4141 gatccttgag agtttttcgcc ccgaagaacg ttttccaatg atgagcactt ttaaagttct
4201 gctatgtggc gcggtattat cccgtattga cgccgggcaa gagcaactcg gtcgccgcat
4261 acactattct cagaatgact tggttgagta ctcaccagtc acagaaaagc atcttacgga
4321 tggcatgaca gtaagagaat tatgcagtgc tgccataacc atgagtgata acactgcggc
4381 caacttactt ctgacaacga tcggaggacc gaaggagcta accgcttttt tgcacaacat
4441 gggggatcat gtaactcgcc ttgatcgttg ggaaccggag ctgaatgaag ccataccaaa
4501 cgacgagcgt gacaccacga tgcctgtagc aatggcaaca acgttgcgca aactattaac
4561 tggcgaacta cttactctag cttcccggca acaattaata gactggatgg aggcggataa
4621 agttgcagga ccacttctgc gctcggccct tccggctggc tggtttattg ctgataaatc
4681 tggagccggt gagcgtgggt ctcgcggtat cattgcagca ctggggccag atggtaagcc
4741 ctcccgtatc gtagttatct acacgacggg gagtcaggca actatggatg aacgaaatag
4801 acagatcgct gagataggtg cctcactgat taagcattgg taactgtcag accaagttta
4861 ctcatatata ctttagattg atttaaaact tcatttttaa tttaaaagga tctaggtgaa
4921 gatcctttt gataatctca tgaccaaaat cccttaacgt gagttttcgt tccactgagc
4981 gtcagacccc gtagaaaaga tcaaaggatc ttcttgagat cctttttttc tgcgcgtaat
5041 ctgctgcttg caaacaaaaa aaccaccgct accagcggtg gtttgtttgc cggatcaaga
5101 gctaccaact ctttttccga aggtaactgg cttcagcaga gcgcagatac caaatactgt
5161 ccttctagtg tagccgtagt taggccacca cttcaagaac tctgtagcac cgcctacata
5221 cctcgctctg ctaatcctgt taccagtggc tgctgccagt ggcgataagt cgtgtcttac
5281 cgggttggac tcaagacgat agttaccgga taaggcgcag cggtcgggct gaacggggggg
5341 ttcgtgcaca cagcccagct tggagcgaac gacctacacc gaactgagat acctacagcg
5401 tgagctatga gaaagcgcca cgcttcccga agggagaaag gcggacaggt atccggtaag
5461 cggcagggtc ggaacaggag agcgcacgag ggagcttcca gggggaaacg cctggtatct
```

```
-continued
5521 ttatagtcct gtcgggtttc gccacctctg acttgagcgt cgattttgt gatgctcgtc 5581 aggggggcgg agcctatgga aaaacgccag caacgcggcc tttttacggt tcctggcctt 5641 ttgctggcct tttgctcaca tgttctttcc tgcgttatcc cctgattctg tggataaccg 5701 tattaccgcc tttgagtgag ctgataccgc tcgccgcagc cgaacgaccg agcgcagcga 5761 gtcagtgagc gaggaagcgg aagagc
```

The SOD shRNA nucleotides 901-965 comprise the entire hairpin sequence including the sense and antisense arms, stem loop and termination sequence. The sequence in a forward orientation (with target sequences against SOD1 underlined) is:

(SEQ ID NO: 21)
5'AATTCATATTTGCATGTCGCTATGTGTTCTGGGAAATCACCATAAACG

TGAAATGTCTTTGGATTTGGGAATCTTATAAGTTCTGTATGAGACCACTC

GGATCCATGGATTCCATGTTCATGATTCAAGAGATCATGAACATGGAATC

CATGCTTTTTTGGAAA 3'

The rAAV of the invention may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69: 427-443 (2002); U.S. Pat. No. 6,566,118 and WO 98/09657.

In another aspect, the invention contemplates compositions comprising rAAV of the present invention. Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about about $1\times10^2$, about $1\times10^3$, about $1\times10^4$, about $1\times10^5$, about $1\times10^6$, about $1\times10^7$, about $1\times10^8$, about $1\times10^9$, about $1\times10^{10}$, about $1\times10^{11}$, about $1\times10^{12}$, about $1\times10^{13}$ to about $1\times10^{14}$ or more DNase resistant particles (DRP) per ml. Dosages may also be expressed in units of viral genomes (vg). Dosages may also vary based on the timing of the administration to a human. These dosages of rAAV may range from about $1\times10^4$, about $1\times10^5$, about $1\times10^6$, about $1\times10^7$, about $1\times10^8$, about $1\times10^9$, about $1\times10^{10}$, about $1\times10^{11}$, about $1\times10^{12}$, about $1\times10^{13}$, about $1\times10^{14}$, about $1\times10^{15}$, about $1\times10^{16}$ or more viral genomes per kilogram body weight in an adult. For a neonate, the dosages of rAAV may range from about about $1\times10^4$, about $3\times10^4$, about $1\times10^5$, about $3\times10^5$, about $1\times10^6$, about $3\times10^6$, about $1\times10^7$, about $3\times10^7$, about $1\times10^8$, about $3\times10^8$, about $1\times10^9$, about $3\times10^9$, about $1\times10^{10}$, about $3\times10^{10}$, about $1\times10^{11}$, about $3\times10^{11}$, about $1\times10^{12}$, about $3\times10^{12}$, about $1\times10^{13}$, about $3\times10^{13}$, about $1\times10^{14}$, about $3\times10^{14}$, about $1\times10^{15}$, about $3\times10^{15}$, about $1\times10^{16}$, about $3\times10^{16}$ or more viral genomes per kilogram body weight.

In another aspect, the invention contemplates compositions comprising rAAV of the present invention. Compositions of the invention comprise rAAV in a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

In still another aspect, the invention provides methods of transducing a target cell with a rAAV of the invention, in vivo or in vitro. The in vivo methods comprise the step of administering an effective dose, or effective multiple doses, of a composition comprising a rAAV of the invention to a subject, a subject (including a human being), in need thereof. If the dose is administered prior to onset/development of a disorder/disease, the administration is prophylactic. If the dose is administered after the onset/development of a disorder/disease, the administration is therapeutic. In embodiments of the invention, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for treatment with methods of the invention is ALS. "Treatment" according to the invention thus alleviates (eliminates or reduces) at least one symptom associated with the disorder/disease state being treated (for example, weight loss is eliminated or reduced by at least 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100% or greater), that slows or prevents progression to (onset/development) of a disorder/disease state, that slows or prevents progression of a disorder/disease state, that diminishes the extent of disease, that results in remission (partial or total) of disease, and/or that prolongs survival. In some embodiments, survival is prolonged by at least 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, 100% or greater.

Combination therapies are also contemplated by the invention. Combination as used herein includes both simultaneous treatment or sequential treatments. Combinations of methods of the invention with standard medical treatments (e.g., riluzole) are specifically contemplated, as are combinations with novel therapies.

Administration of an effective dose of the compositions may be by routes standard in the art including, but not limited to, systemic intramuscular, parenteral, intravenous, oral, buccal, nasal, pulmonary, intracranial, intrathecal, intraosseous, intraocular, rectal, or vaginal. Route(s) of administration and serotype(s) of AAV components of the rAAV (in particular, the AAV ITRs and capsid protein) of the invention may be chosen and/or matched by those skilled in the art taking into account the infection and/or disease state being treated and the target cells/tissue(s) that are to express the SOD1 shRNAs. In some embodiments, the route of administration is systemic. In some, embodiments the route of administration is intrathecal. In some, embodiments the route of administration is introcerebroventricular. In some, embodiments the route of administration is cisterna magna. In some, embodiments the route of administration is by lumbar puncture.

Transduction of cells with rAAV of the invention results in sustained expression of SOD1 shRNAs. In another aspect, the present invention thus provides methods of administering/delivering rAAV which express SOD1 shRNA to a subject, preferably a human being. The term "transduction" is used to refer to the administration/delivery of SOD1 shRNAs to a recipient cell either in vivo or in vitro, via a replication-deficient rAAV of the invention resulting in expression of a SOD1 shRNA by the recipient cell.

Thus, the invention provides methods of administering an effective dose (or doses, administered essentially simultaneously or doses given at intervals) of rAAV that encode SOD1 shRNAs to a subject in need thereof.

In one aspect, the invention provides methods of delivering a polynucleotide encoding an shRNA of the invention across the BBB comprising systemically administering a rAAV with a genome including the polynucleotide to a subject. In some embodiments, the rAAV genome is a self complementary genome. In other embodiments, the rAAV genome is a single-stranded genome. In some embodiments, the rAAV is a rAAV9. In some embodiments, the rAAV is a rAAV2. In some embodiments, the rAAV is a rAAVrh74.

In some embodiments, the methods systemically deliver polynucleotides across the BBB to the central and/or peripheral nervous system. Accordingly, a method is provided of delivering a polynucleotide to the central nervous system comprising systemically administering a rAAV with a self-complementary genome including the genome to a subject. In some embodiments, the polynucleotide is delivered to brain. In some embodiments, the polynucleotide is delivered to the spinal cord. Also provided is a method of delivering a polynucleotide to the peripheral nervous system comprising systemically administering a rAAV with a self-complementary genome including the polynucleotide to a subject is provided. In some embodiments, the polynucleotide is delivered to a lower motor neuron. In some embodiments, the rAAV genome is a self complementary genome. In other embodiments, the rAAV genome is a single-stranded genome. In some embodiments, the rAAV is a rAAV9. In some embodiments, the rAAV is a rAAV2. In some embodiments, the rAAV is a rAAVrh74.

In another aspect, the invention provides methods of delivering a polynucleotide to the central nervous system of a subject in need thereof comprising intrathecal delivery of rAAV with a genome including the polynucleotide. In some embodiments, the rAAV genome is a self complementary genome. In other embodiments, the rAAV genome is a single-stranded genome. In some embodiments, the rAAV is a rAAV9. In some embodiments, the rAAV is a rAAV2. In some embodiments, the rAAV is a rAAVrh74. In some embodiments, a non-ionic, low-osmolar contrast agent is also delivered to the subject, for example, iobitridol, iohexol, iomeprol, iopamidol, iopentol, iopromide, ioversol or ioxilan.

Embodiments of the invention employ rAAV to deliver polynucleotides to nerve, glial cells and endothelial cells. In some embodiments, the nerve cell is a lower motor neuron and/or an upper motor neuron. In some embodiments, the glial cell is a microglial cell, an oligodendrocyte and/or an astrocyte. In other aspects the rAAV is used to deliver a polynucleotide to a Schwann cell.

BRIEF DESCRIPTION OF THE DRAWINGS

FIGS. 1A-1U. AAV9 transduction pattern and persistence in SOD1$^{G93A}$ mice. SOD1$^{G93A}$ mice were injected intravenously with AAV9-CB-GFP at P1, P21 and euthanized 21 days post injection (n=3 per time point). Spinal cords were examined for GFP, ChAT (motor neuron marker) and GFAP (astrocyte marker) expression. Temporal vein injection of AAV9-CB-GFP at P1 resulted in efficient transduction of motor neurons and glia in SOD1$^{G93A}$ mice (FIGS. 1A, 1F, 1K, and 1P). Tail vein injection at P21 (FIG. 1B, FIG. 1G, FIG. 1L, FIG. 1Q) predominantly targeted astrocytes with few GFP positive motor neurons. To test the persistence of transduced cells, AAV9-CB-GFP was intravenously injected at P1 and P21 in SOD1$^{G93A}$ animals that were sacrificed at end stage (~P130). Immunofluorescence analysis of lumbar ventral horn (FIG. 1C, FIG. 1D, FIG. 1H, FIG. 1I, FIG. 1M, FIG. 1N, FIG. 1R, FIG. 1S) demonstrated that GFP expression was maintained in astrocytes throughout the disease course. To determine whether SOD1 mediated inflammation and damage would affect AAV9 transduction, we intravenously injected SOD1$^{G93A}$ mice at P85 and harvested their spinal cords at endstage. There was no difference observed in the transduction pattern of SOD1$^{G93A}$ mice treated at P21 or P85. Insets in (FIG. 1R, FIG. 1S, FIG. 1T) show co-localization between GFP and GFAP signal. (FIG. 1U) Quantification of transduced cells in ALS spinal cords (for each group tissues were analyzed from 3 animals). GFP and ChAT columns show numbers of cells counted. Bars=100 μm. AAV, adeno-associated virus; P1, postnatal day 1; P21, postnatal day 21; P85, postnatal day 85; GFP, green fluorescent protein; ChAT, choline acetyltransferase; GFAP, glial fibrillary acidic protein.

FIGS. 2A-2E. shRNA constructs show efficient reduction of human SOD1 protein in vitro and in vivo. (FIG. 2A) Sequence alignments between human and mouse SOD1 for the regions targeted by the 4 different shRNA constructs tested. (FIG. 2B) shRNA sequences were cloned into an H1 expression construct and transiently transfected into 293 cells. Lysates were collected 72 hours post transfection and analyzed by western blot. (FIG. 2C) Quantification of in vitro suppression of human SOD1 from three separate transient transfections showed >50% reduction in SOD1. (FIG. 2D) shRNA 130 was packaged into AAV9 and injected into SOD1$^{G93A}$ mice at either P1 or P21. Spinal cords (n=3 per time point) were harvested three weeks post injection and analyzed by western blot for human SOD1 protein levels. (FIG. 2E) Quantification of in vivo suppression of human SOD1 within the spinal cord of ALS mice. P1 and P21 injected spinal cords showed 60% and 45% reductions in mutant SOD1 protein, respectively, hSOD1, human superoxide dismutase 1; mSOD1, mouse superoxide dismutase 1; GAPDH, glyceraldehyde 3 phosphate dehydrogenase.

FIGS. 3A-3H. Intravenous delivery of AAV9-SOD1-shRNA improves survival and motor performance in SOD1$^{G93A}$ mice. SOD1$^{G93A}$ mice received a single intravenous injection of AAV9-SOD1-shRNA at P1 (n=6, green), P21 (n=9, red) or P85 (n=5, blue). Treated mice were monitored up to end stage and compared with non-injected control SOD1$^{G93A}$ mice (n=15, gray). (FIG. 3A, FIG. 3C) AAV9-SOD1-shRNA injection into P1 SOD1$^{G93A}$ mice significantly delayed median disease onset 39.5 days compared to control animals (uninjected, 103d; P1, 142.5d; p<0.05). Injection in P21 (red) or P85 (blue) ALS animals had no effect on disease onset (P21, 110d; P85, 105d). However, AAV9-SOD1-shRNA administered at P1, P21 or P85 all significantly extended median survival (FIG. 3B, FIG. 3E) (uninjected, 132d; P1, 183.5d P21, 171d; P85, 162d; all comparisons to control p<0.001). The P21 group had a significant extension in median disease duration (FIG. 3D) indicating a slowing of disease (uninjected, 29.5d; P1, 41d; P21, 49d; P85, 40d; Wilcoxon Signed Rank Test p=0.06, 0.01 and 0.12, respectively). (FIG. 3F, FIG. 3G, FIG. 3H) P1 and P21 treated animals maintained their weights, had better hind limb grip strength and rotarod performance when compared to age-matched controls, indicating treated animals retained muscle tone and motor function during their prolonged survival. Lines between bars in (FIG. 3C, FIG. 3D, FIG. 3E) indicate statistically significant differences. * p<0.05. P1, postnatal day 1; P21, postnatal day 21; P85, postnatal day 85.

FIGS. 4A-4T. Intravenous injection of AAV9-SOD1-shRNA reduces mutant protein in spinal cords of SOD1$^{G93A}$ mice. (FIG. 4A, FIG. 4B, FIG. 4C, FIG. 4D) Images of lumbar spinal cord sections from uninjected (FIG. 4A), P1 injected (FIG. 4B), P21 injected (FIG. 4C) and P85 injected (FIG. 4D) mice were captured with identical microscope settings to qualitatively show SOD1 levels at end stage. SOD1 levels inversely correlate with survival. (FIG. 4E, FIG. 4F, FIG. 4G, FIG. 4H, FIG. 4I, FIG. 4J, FIG. 4K, FIG. 4L, FIG. 4M, FIG. 4N, FIG. 4O, FIG. 4P, FIG. 4Q, FIG. 4R, FIG. 4S, FIG. 4T) Co-labeling for GFP, ChAT and SOD1 shows that AAV9 transduced motor neurons had reduced SOD1 expression (arrows) while cells that lacked GFP maintained high levels of mutant protein (arrowheads). As described in FIG. 1U, higher MN transduction and corresponding SOD1 reduction was observed in P1 injected mice (FIG. 4I, FIG. 4J, FIG. 4K, FIG. 4L) as compared to P21 injected (FIG. 4M, FIG. 4N, FIG. 4O, FIG. 4P) and P85 injected (FIG. 4Q, FIG. 4R, FIG. 4S, FIG. 4T) mice. Bar=100 μm. P1, postnatal day 1; P21, postnatal day 21; P85, postnatal day 85; SOD1, superoxide dismutase 1; GFP, green fluorescent protein; ChAT, choline acetyltransferase.

(FIG. 5A) There was no difference in median disease onset between AAV9-SOD1-shRNA and control treated mice. (average age at treatment=215d versus median onset of 194d control and 197d treated; Log Rank Test p=0.46). (FIG. 5B, FIG. 5F) Median survival of AAV9-SOD1-shRNA treated SOD1$^{G37R}$ mice (n=25) was significantly extended versus control mice (n=21). (control, n=21, 392d; SOD1 shRNA, n=25, 478.5d; Log Rank Test p<0.0001) (FIG. 5C, FIG. 5D, FIG. 5E). The early phase of disease was significantly slowed by 73 days in treated mice as compared to control mice (control, 89d; SOD1 shRNA, 162d; p<0.0001 Wilcoxon Signed Rank Test) while the late phase of disease showed a non-significant slowing (control, 63d; SOD1 shRNA, 81d; p=0.14 Wilcoxon Signed Rank Test). Together this amounted to a 66 day increase in median disease duration (control, 173d; SOD1 shRNA, 239d; p<0.0001 Wilcoxon Signed Rank Test). (FIG. 5G) A trend to improved hind limb grip strength appeared in AAV9-SOD1-shRNA treated mice compared to control mice.

FIGS. 6A-6P. Intravenous injection of AAV9 in adult SOD1$^{G37R}$ mice targets astrocytes and motor neurons within the spinal cord. (FIG. 6A, FIG. 6B, FIG. 6C, FIG. 6D, FIG. 6E, FIG. 6F, FIG. 6G, FIG. 6H) Immunofluorescence analysis revealed neuronal as well as glial transduction in both AAV9-CB-GFP (FIG. 6A, FIG. 6B, FIG. 6C, FIG. 6D) and AAV9-SOD1-shRNA treated (FIG. 6E, FIG. 6F, FIG. 6G, FIG. 6H) mice. (FIG. 6I, FIG. 6J, FIG. 6K, FIG. 6L, FIG. 6M, FIG. 6N, FIG. 6O, FIG. 6P) Human SOD1 levels appeared reduced in AAV9-SOD1-shRNA treated mice (FIG. 6O) compared with AAV9-GFP treated mice (FIG. 6K). Bar=100 GFP, green fluorescent protein; ChAT, choline acetyltransferase; GFAP, glial fibrillary acidic protein; SOD1, superoxide dismutase 1.

(FIG. 7A) A myelogram shortly after intrathecal infusion of AAV9-SOD1-shRNA mixed with contrast shows proper delivery into the subarachnoid space of a cynomolgus macaque. Arrows show diffusion of the contrast agent along the entire spinal cord. (FIG. 7B) Lumbar spinal cord sections from treated monkeys (n=3) were harvested two weeks post injection and stained for GFP using DAB staining. Sections had widespread GFP expression throughout the grey and white matter. (FIG. 7C, FIG. 7D, FIG. 7E) Immunofluorescence analysis of the lumbar spinal cord sections showed robust GFP (FIG. 7C) expression within ChAT (FIG. 7D) positive cells indicating motor neuron transduction (FIG. 7E, merge). (FIG. 7F) Western blot analysis of the lumbar spinal cords showed significant reduction in SOD1 levels in AAV9-SOD1-shRNA injected animals as compared to controls. (FIG. 7G) In vivo quantification of SOD1 knockdown in monkey lumbar spinal cord homogenate (n=3) showed an 87% reduction in animals that received AAV9-SOD1-shRNA compared to uninjected controls. (FIG. 7H) Laser capture microdissection was used to collect motor neurons or surrounding neuropil from injected and control lumbar monkey sections. Collected cells were analyzed for SOD1 levels by qRT-PCR. Motor neurons collected from AAV9-SOD1-shRNA animals (n=3) had a 95±3% reduction in SOD1 RNA. Non-neurons had a 66±9% reduction in SOD1 RNA in AAV9-SOD1-shRNA treated animals. Scale Bars: b=100 μm; e=50 μm. SOD1: Superoxide dismutase 1.

FIGS. 8A-8E. Lumbar intrathecal infusion of AAV9-SOD1-shRNA leads to efficient transduction of motor neurons and non-neuronal cells in the cervical, thoracic and lumbar cord resulting in reduction of SOD1. (FIG. 8A, FIG. 8B, FIG. 8C) Immunofluorescence analysis of the three segments of the spinal cord; cervical (FIG. 8A), thoracic (FIG. 8B) and lumbar (FIG. 8C), showed robust GFP (green) expression within Chat (red) positive cells indicating motor neuron transduction. (FIG. 8D) GFP+/Chat+ cell counts show a caudal to rostral gradient of motor neuron transduction ranging from 85% of transduced cells in the lumbar region to more than 50% in the cervical region. (FIG. 8E)

SOD1 mRNA levels in cervical, thoracic and lumbar cord section homogenates analyzed by qRT-PCR show significant reduction in SOD1 transcript, consistently with motor neuron transduction. SOD1 levels were normalized to β-actin and AAV9-SOD1-shRNA injected animals were compared to an AAV9-CB-GFP injected control. Scale bars: (FIG. 8A, FIG. 8B, FIG. 8C)=50 µm; Error bars: (FIG. 8D, FIG. 8E)=SD.

FIGS. 9A-B. Design of a clinical SOD1 shRNA construct. (FIG. 9A) Original AAV SOD1 shRNA construct contains shRNA sequence against human SOD1 under H1 promoter followed by the expression cassette for GFP which includes CMV enhancer, CBA promoter, modified SV40 intron, and GFP transgene sequence followed by bGH PolyA terminator. SOD1 shRNA expression cassette and GFP expression cassette are flanked by AAV2 ITRs which ensures the packaging of the complete flanked sequence in AAV9 capsid. (FIG. 9B) In clinical SOD1 shRNA construct, the GFP expression cassette is replaced by a stuffer element that contains tandem, noncoding sequences from FDA approved DNA vaccines. ITR: inverted terminal repeats; shRNA, small hairpin RNA; SOD1, superoxide dismutase 1; CMV, cytomegalo virus enhancer; CBA, Chicken β-actin promoter; GFP, green fluorescent protein; bGH pA, bovine growth hormone poly A terminator.

(FIG. 11I) Western blot analysis of the cell lysates confirms the efficient knockdown of human SOD1 protein in pJet SOD1 shRNA transfected cells as compared to the non-transfected control cells. Immunoblot analysis also confirms removal of GFP transgene from pJet SOD1 shRNA construct. (FIG. 11J) Quantification of the in vitro downregulation of SOD1 by pJet SOD1 shRNA. pJet SOD1 shRNA reduces the protein levels of human SOD1 by almost 50% in HEK293 cells as compared to control. This reduction is similar to that achieved with AAV SOD1 shRNA construct.

(FIG. 13G) Western blot analysis of cell lysates, harvested 72 hrs post-transfection confirmed efficient downregulation of SOD1 in clinical AAV SOD1 shRNA transfected cells as compared to control. AAV SOD1 shRNA was used as a positive control. (FIG. 13H) Quantification of the in vitro knockdown of SOD1 by clinical AAV SOD1 shRNA.

Figure 3F:
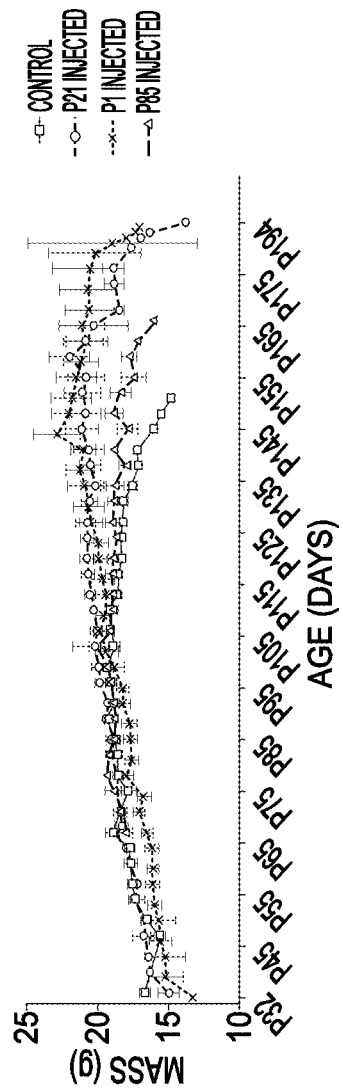

Figures S1A-S1F. AAV9-shRNA-SOD1 administration is well tolerated in WT mice. Female and male WT animals were injected with AAV9-SOD1-shRNA at P1 or P21 and monitored up to 6 months of age. (Figure S1A, Figure S1B) Both male and female treated mice showed steady increase in body mass as compared to control animals. (Figure S1C, Figure S1D) Rotarod performance and (Figure S1E, Figure S1F) hind limb grip strength were not affected by P1 or P21 treatment in both groups as compared to respective controls. n=5 per group. WT, wild type; P1, postnatal day 1; P21, postnatal day 21.

Figures S2A-S2W. Hematology and Serum Chemistry of AAV9-SOD1-shRNA treated WT animals. (Figure S2A, Figure S2B, Figure S2C, Figure S2D, Figure S2E, Figure S2F, Figure S2G, Figure S2H, Figure S2I, Figure S2J, Figure S2K, Figure S2L, Figure S2M) Blood was collected from P1 (green) or P21 (red) treated and control (gray) WT animals at 150 days of age for hematology studies. No significant differences were observed between treated and control animals. (Figure S2N, Figure S2O, Figure S2P, Figure S2Q, Figure S2R, Figure S2S, Figure S2T, Figure S2U, Figure S2V, Figure S2W) Serum samples collected at 180 days of age from the same mice showed no significant differences in serum chemistry profile. Mean±SEM. n=5 per group. P1, postnatal day 1; P21, postnatal day 21.

Figures S3A-S3H. AAV9-SOD1-shRNA treatment in SOD1$^{G93A}$ mice reduces astrogliosis. End stage sections from control and AAV9-SOD1-shRNA treated animals were harvested and stained for GFAP, an astrocyte activation marker. P1 (Figure S3B) and P85 (Figure S3D) injected mice showed reduced levels of astrogliosis as compared to control (Figure S3A) mice while P21 (Figure S3C) injected mice showed the maximum reduction. This was consistent with the percent astrocyte transduction achieved in these mice (FIG. 1U). However, no effect was observed on microglia reactivity (Figure S3E, Figure S3F, Figure S3G, Figure S3H). Bar=100 µm. P1, postnatal day 1; P21, postnatal day 21; P85, postnatal day 85.

Figures S4A-S4B. Intravenous injection of AAV9-SOD1-shRNA efficiently reduces levels of mutant SOD1 protein in spinal cords of SOD1$^{G37R}$ mice. (Figure S4A) Following disease onset, AAV9-CB-GFP or AAV9-SOD1-shRNA was injected in SOD1$^{G37R}$ mice and spinal cords were harvested at end stage and analyzed by western blot for human SOD1 protein levels. (Figure S4B) Quantification of a) shows suppression of human SOD1 within the spinal cord of SOD1$^{G37R}$ mice (n=4 per group), hSOD1, human superoxide dismutase 1; GAPDH, glyceraldehyde 3 phosphate dehydrogenase.

Figures S5A-S5B shRNA 130 efficiently reduces the levels of monkey SOD1 in vitro. (Figure S5A) Sequence alignment of the region targeted by SOD1 shRNA 130 and a single mismatch with the monkey sequence. Monkey sequence corresponds to SOD1 sequence from Rhesus monkey (NM 001032804.1), Cynomolgus monkey (sequenced in-house) and African green monkey. (Figure S5B) The shRNA 130 expression cassette was cloned into lentiviral vector and used to infect Cos-7 cells. Lysates were analyzed 72 hours post infection by qRT PCR for SOD1, shRNA 130 reduced SOD1 transcript levels by 75% in Cos-7 cells.

EXAMPLES

The present invention is illustrated by the following examples. While the present invention has been described in terms of various embodiments and examples, it is understood that variations and improvements will occur to those skilled in the art. Therefore, only such limitations as appear in the claims should be placed on the invention.

Example 1

AAV9 Transduction Pattern and Persistence in SOD1$^{G93A}$ Mice

We first evaluated the efficiency of AAV9 transduction in the SOD1$^{G93A}$ mouse model that develops fatal paralytic disease. High copy SOD1$^{G93A}$ mice were obtained from Jackson Laboratories (Bar Harbor, Me.) and bred within the Kaspar lab. Animals were genotyped before the treatment to obtain SOD1$^{G93A}$ expressing mice and their wild type littermates. Only female mice were included in the SOD1$^{G93A}$ experiments. Animals were injected intravenously at postnatal day 1 or day 21 (to be referred to as P1 and P21, respectively) with self-complementary AAV9 expressing GFP from the CMV enhancer/beta-actin (CB) promoter (AAV9-CB-GFP) (n=3 per group). Three weeks post-injection, animals were sacrificed, and spinal cords examined for GFP expression (FIG. 1A, FIG. 1B, FIG. 1C, FIG. 1D, FIG. 1E, FIG. 1F, FIG. 1G, FIG. 1H, FIG. 1I, FIG. 1J, FIG. 1K, FIG. 1L, FIG. 1M, FIG. 1N, FIG. 1O, FIG. 1P, FIG. 1Q, FIG. 1R, FIG. 1S, FIG. 1T, FIG. 1U).

All procedures with animals described herein were performed in accordance with the NIH Guidelines and approved by the Research Institute at Nationwide Children's Hospital (Columbus, Ohio), University of California (San Diego, Calif.) or Mannheimer Foundation (Homestead, Fla.) Institutional Animal Care and Use Committees.

Transduction efficiency was high in SOD1$^{G93A}$ astrocytes with GFP expressed in 34±2% and 54±3%, respectively, of P1 and P21 injected spinal grey matter astrocytes (defined by immunoreactivity for GFAP). This efficiency was similar to our previous report of 64±1% in P21 injected wild type animals[18]. Motor neurons were a prominent cell type transduced at all levels of the spinal cords of P1 injected SOD1$^{G93A}$ animals (62±1%), compared with significantly lower targeting to motor neurons in P21 injected animals (8±1%).

Although we have previously reported that transduced astrocytes in wild type spinal cords persist with continued GFP accumulation for at least 7 weeks post injection[18], longevity of mutant SOD1 astrocytes (and their continued synthesis of genes encoded by the AAV9 episome) during active ALS-like disease was untested. Therefore, SOD1$^{G93A}$ mice were injected at P1 and P21 with AAV9-CB-GFP and followed to end-stage (~P130, n=3 per group) (FIG. 1C, FIG. 1D, FIG. 1H, FIG. 1I, FIG. 1M, FIG. 1N, FIG. 1R, FIG. 1S). Immunofluorescent examination of the end-stage SOD1$^{G93A}$ spinal cords from animals injected at P1 and P21 showed a comparable number of GFP-expressing astrocytes as were found 21 days after AAV9 injection (P1: 42±2%, P21: 61±2%). These data are consistent with survival of transduced astrocytes for the duration of disease (~110 days post injection at P21) in SOD1$^{G93A}$ mice and that AAV9-encoded gene expression is maintained.

Further, recognizing that SOD1 mutant mediated damage, including astrocytic and microglial activation and early changes in the blood brain barrier develop during disease in mice in SOD1 mutant mice[20], we tested if this damage affected AAV9 transduction. SOD1$^{G93A}$ mice were injected at P85 with AAV9-CB-GFP and sacrificed at endstage (n=3) (FIG. 1E, FIG. 1J, FIG. 1O, FIG. 1T). Analysis of the spinal cords revealed that the transduction pattern seen in P85 animals was similar to P21 treated animals with astrocytes as the predominant cell type transduced at all levels (51±6% GFP+/GFAP+ cells in lumbar grey matter).

Example 2

Development of an shRNA Sequence Specific for Human SOD1

To specifically target the human SOD1 mRNA, four shRNA constructs targeting human SOD1 were generated and obtained from the Life Technologies design tool. The constructs that had a minimum of four base mismatches compared to the mouse mRNA sequence (FIG. 2A). The base numbers for the human sequences shown correspond to record number CCDS33536.1 in the NCBI CCDS database. These constructs were cloned in pSilencer 3.1 (Genscript) under the human H1 promoter and tested in vitro. shRNA 130 along with H1 promoter was further cloned into an AAV vector along with a reporter GFP under Chicken Beta-Actin promoter to identify the transduced cells. Human 293 cells were transfected with each cassette. The HEK-293 cells were maintained in IMDM medium containing 10% FBS, 1% L-glutamine and 1% penicillin/streptomycin. Upon reaching ~60% confluence, cells were transfected with pSilencer 3.1 containing the shRNAs being tested. Protein lysates were prepared 72 hours post transfection and analyzed for SOD1 levels by western blot. All four sequences reduced SOD1 protein levels by >50% (FIG. 2B, FIG. 2C).

shRNA130 was selected for further experiments because it produced the most consistent knockdown across three separate transfection experiments. It was cloned into a self-complementary AAV9 vector that also contained a GFP gene whose expression would identify transduced cells (referred to as AAV9-SOD1-shRNA). Self-complementary AAV9-SOD1-shRNA was produced by transient transfection procedures using a double-stranded AAV2-ITR-based CB-GFP vector, with a plasmid encoding Rep2Cap9 sequence as previously described along with an adenoviral helper plasmid pHelper (Stratagene, Santa Clara, Calif.) in 293 cells[18].

To confirm that the shRNA could suppress accumulation of human SOD1, SOD1$^{G93A}$ mice (n=3) were injected intravenously with AAV9-SOD1-shRNA at either P1 or P21. For neonatal mouse injections, postnatal day 1-2 SOD1$^{G93A}$ pups were utilized. Total volume of 50 µl containing 5×10$^{11}$ DNAse resistant viral particles of AAV9-SOD1-shRNA (Virapur LLC, San Diego, Calif.) was injected via temporal vein as previously described[18]. A correct injection was verified by noting blanching of the vein. After the injection, pups were returned to their cage. Animals were euthanized three weeks post injection and the spinal cords were harvested and analyzed by immunoblotting for both human (mutant) and murine (wild-type) SOD1 protein. P1 and P21 injected spinal cords showed 60% and 45% reductions in mutant SOD1 protein, respectively (FIG. 2D, FIG. 2E). Murine SOD1 levels remained unchanged in response to human SOD1 knockdown.

Example 3

AAV9-SOD1-shRNA is Safe and Well Tolerated in Wild Type Mice

To determine whether high dose AAV9-SOD1-shRNA would be safe, normal mice of both sexes were intravenously injected at P1 or P21 (P1=5 males, 5 females at $5\times10^{11}$ vg; P21=5 males, 5 females at $2\times10^{12}$ vector genomes (vg)) and then monitored up to 6 months of age. Both P1 and P21 injected mice showed a steady increase in body mass similar to untreated mice (Figures S1A-S1F). Weekly behavioral tests observed no significant differences between injected and control groups in motor skills (measured by rotarod) as well as in hind limb grip strength. At 150 and 180 days of age, blood samples were collected. Complete and differential blood counts of both treated and untreated groups showed similar blood chemistry parameters (Figures S2A-S2W). Serum samples from both groups showed no significant differences in the levels of alkaline phosphatase, creatinine, blood urea nitrogen, potassium, sodium and chloride. Finally, all the animals were sacrificed at the age of 180 days. Histopathological analyses by a pathologist blinded to treatment group revealed no significant alterations in the AAV9-SOD1-shRNA treated animals compared to uninjected controls (data not shown). We conclude that both administration of AAV9 and sustained shRNA expression were apparently safe and well tolerated.

Example 4

Extended Survival of SOD1$^{G93A}$ Mice from AAV9 Mediated Reduction in Mutant SOD1 Even when Initiated Mid-Disease To test the efficacy of AAV9-mediated SOD1 reduction, we treated cohorts of SOD1$^{G93A}$ mice with a single intravenous injection of AAV9-SOD1-shRNA before (P1, $5\times10^{11}$ vg, n=6 and P21, $2\times10^{12}$ vg, n=9) or after (P85, $3\times10^{12}$ vg, n=5) onset, recognizing that many astrocytes, but few motor neurons, would be transduced at the two later time points. For adult tail vein injections, animals were placed in a restraint that positioned the mouse tail in a lighted, heated groove. The tail was swabbed with alcohol then injected intravenously with AAV9-SOD1-shRNA.

Figure 3G:
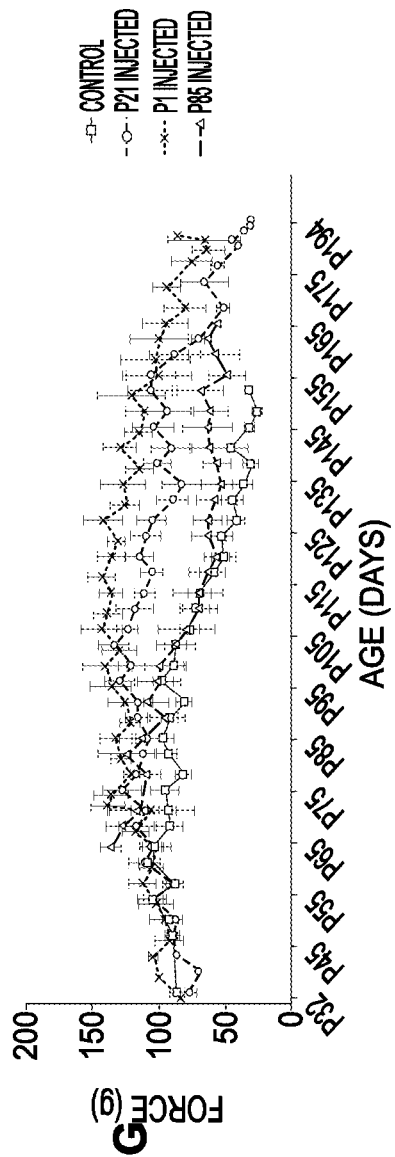
Figure 3H:
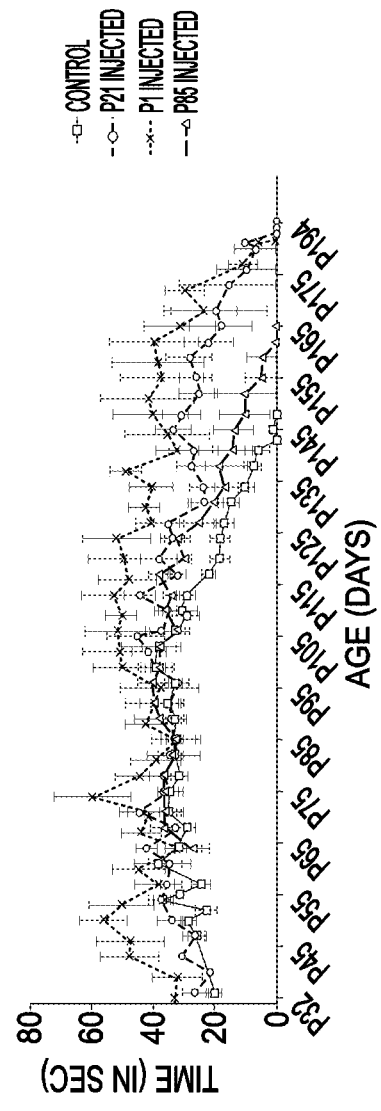

Onset of disease (measured by weight loss from denervation-induced muscle atrophy) was significantly delayed by a median of 39.5 days (FIG. 3A, FIG. 3C; uninjected, 103d; P1, 142.5d; $p<0.05$, Wilcoxon Signed Rank Test) in the P1 injected cohort, but was not affected by either of the later injections (P21, 110d; P85, 105d). P1 and P21 treated animals maintained their weights, had better rotarod performance and hind limb grip strength when compared to age-matched controls, indicating treated animals maintained muscle tone and motor function during their prolonged survival (FIG. 3F, FIG. 3G, FIG. 3H). Survival was significantly extended by AAV9 injection at all three ages, yielding survival times 30-51.5 days beyond that of uninjected SOD1$^{G93A}$ mice (uninjected, 132d; P1, 183.5d; P21, 171d; P85, 162d; Log-Rank Test p=<0.0001, 0.0003 and 0.001, respectively) (FIG. 3B, FIG. 3E). Defining disease duration as the time from onset to end-stage revealed that the P21 treatment group had significantly increased duration, indicative of slowed disease progression, compared to uninjected controls (uninjected, 29.5d; P21, 49d; Wilcoxon Signed Rank Test p=0.01), with trends toward slowed progression in animals injected at the other two ages (P1, 41d; P85, 40d; p=0.06 and 0.12, respectively) (FIG. 3D). The lower percentage of targeted non-neuronal cells at P1 versus those targeted at P21 (FIG. 1U) suggests that a minimum number of non-neuronal cells must be targeted to slow disease progression in the fast progressive SOD1$^{G93A}$ model (FIG. 1U).

Example 5

Reduction of Mutant SOD1 in AAV9 Infected Cells in Treated SOD1$^{G93A}$ Mice Indirect immunofluorescence with an antibody that recognizes human, but not mouse SOD1, was used to determine accumulated mutant SOD1 levels in end-stage spinal cords of treated and control mice. Human SOD1 levels in end-stage spinal cord sections inversely correlated with increased survival (FIG. 4A, FIG. 4B, FIG. 4C, FIG. 4D). At end-stage, P1 (FIG. 4B), P21 (FIG. 4C) and P85 (FIG. 4D) AAV9-SOD1-shRNA injected animals had lower levels of mutant SOD1 when compared with uninjected SOD1$^{G93A}$ animals (FIG. 4A). SOD1 expression within transduced motor neurons (identified by GFP and ChAT expressing cells) was reduced compared to surrounding neurons that had not been transduced to express viral encoded GFP (FIG. 4H, FIG. 4L, FIG. 4P, FIG. 4T; arrows versus arrowheads). Moreover, immunofluorescence imaging of end-stage spinal cords revealed corresponding reduction in astrogliosis, but no difference in microgliosis in AAV9-SOD1-shRNA treated animals versus controls (Figures S3A-S3H).

Example 6

Figure 5A:
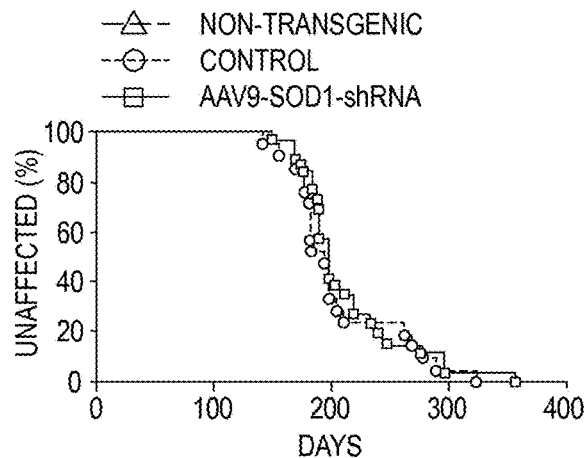
FIGS. 5A-5G. AAV9-SOD1-shRNA improves survival and motor performance in SOD1$^{G37R}$ mice treated after disease onset.
Figure 5B:
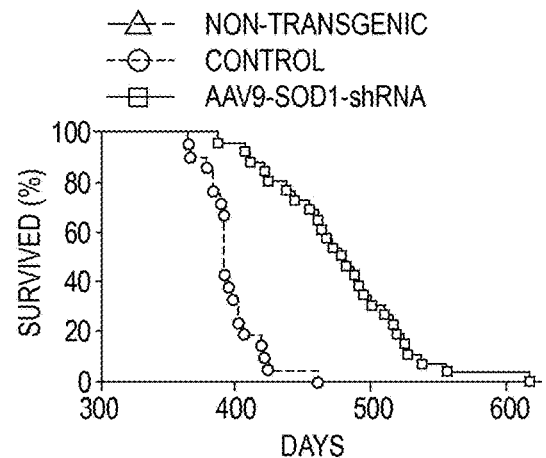

Therapeutic Slowing of Disease Progression with Peripheral Injection of AAV9 after Onset To determine if AAV9-mediated mutant SOD1 reduction would slow disease progression, a cohort of SOD1$^{G37R}$ mice[6] were injected intravenously with AAV9-SOD1-shRNA after disease onset (average age at treatment=215d versus median onset of 197d in treated animals; Log Rank Test p=0.46; FIG. 5A). loxSOD1$^{G37R}$ ALS mice, carrying a human mutant SOD1$^{G37R}$ transgene flanked by lox p sites under its endogenous promoter, were maintained in as previously described[37]. A combination of AAV9-CB-GFP (n=9) and uninjected (n=12) littermates were used as controls.

Figure 5C:
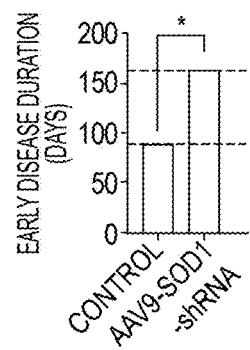
Figure 5D:
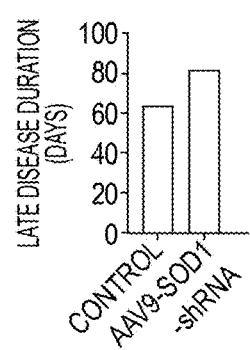
Figure 5E:
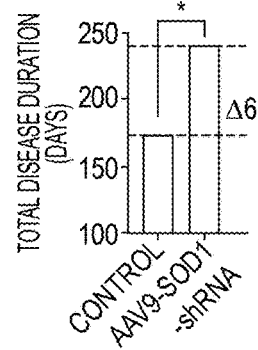
Figure 5F:
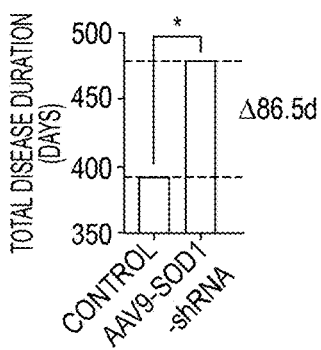
Figure 5G:
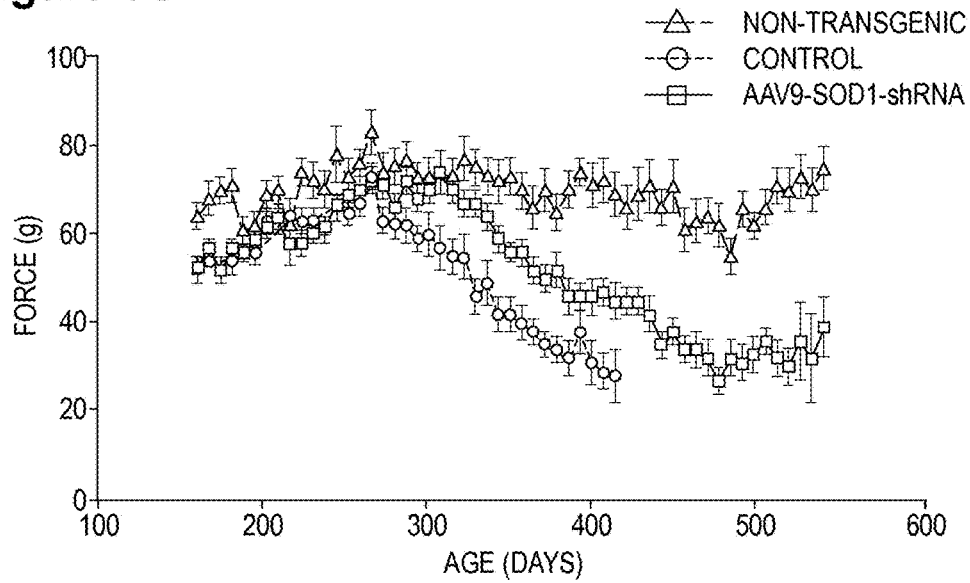

Post hoc analysis showed no differences between GFP and uninjected animals, therefore the groups were compiled as "control" in FIGS. 5A-5G. Animals were evaluated weekly for body weight and hind limb grip strength and monitored until end-stage. AAV9-SOD1-shRNA treatment after disease onset significantly extended median survival by 86.5 days over control animals (control, n=21, 392d; SOD1 shRNA, n=25, 478.5d; Log Rank Test p<0.0001). Early disease duration, defined by the time from peak weight to 10% weight loss, was significantly slowed (control, 89d; SOD1 shRNA treated mice, 162 days; Wilcoxon Signed Rank Test p<0.01; FIG. 5C). A continuing trend toward slowing of later disease (10% weight loss to end stage) was also seen (control, 63d; SOD1 shRNA treated mice, 81d; Wilcoxon Signed Rank Test p=0.1389; FIG. 5D). Overall disease duration following AAV9-SOD1-shRNA therapy rose to 239d after disease onset versus 173d in control mice (Wilcoxon Signed Rank Test p<0.0001; FIG. 5E). Consistent with the slowed progression, AAV9 therapy maintained grip strength relative to control SOD1 mutant animals (FIG. 5G).

The 86.5 day extension in survival surpassed the 62 day extension seen in transgenic studies that used astrocyte-specific Cre expression to inactivate the mutant SOD1$^{G37R}$ transgene[8], presumably reflecting efficient AAV9 transduction of astrocytes after peripheral delivery and the possible transduction of other cell types (especially microglia[6]) whose synthesis of mutant SOD1 accelerates disease progression.

Histological examination of end-stage SOD1$^{G37R}$ treated animals revealed similar levels of intraspinal cell transduction in animals treated with AAV9-SOD1-shRNA or AAV9-GFP (FIGS. 6A-6P). GFP expression was predominantly observed within motor neurons and astrocytes of both groups, and SOD1 expression was detectably decreased only in animals that received AAV9-SOD1-shRNA (FIG. 6K, FIG. 6O). Immunoblotting of whole spinal cord extracts from end stage SOD1$^{G37R}$ mice revealed an 80% reduction in hSOD1 protein levels in AAV9-SOD1-shRNA treated animals compared to controls (Figures S4A-S4B).

Example 7

AAV9 Mediated Suppression of SOD1 in Non-Human Primates

To test whether SOD1 levels could be efficiently lowered using AAV9 in the non-human primate spinal cord, AAV9 was injected intrathecally via lumbar puncture. This method was chosen over systemic delivery to decrease the amount of virus required and to minimize any effects from reduction of SOD1 in peripheral tissues. One year old cynomolgus macaques (*Macaca fascicularis*) with average body weight of 2 kg were used for this study at the Mannheimer Foundation. Regular monitoring of overall health and body weight was performed prior and after the injections to assess the welfare of the animals.

Sequencing of cDNA copied from mRNA isolated from African Green Monkey (COS cells) and the Cynomolgus macaque verified that the 130 shRNA had a single base mismatch to either sequence (Figures S5A-S5B). The 130 shRNA expression cassette was inserted into a lentiviral vector which was then used to transduce COS cells. Cos-7 cells were maintained in DMEM with 10% FBS and 1% penicillin/streptomycin. Cells were infected with a lentiviral vector expressing SOD1 shRNA 130 under the H1 promoter and RFP under CMV promoter. RNA was extracted from infected and non-infected cells 72 hours post infection using an RNAeasy Kit (Qiagen). cDNA was prepared using RT$^2$ First strand synthesis kit (SABiosciences). SOD1 transcript levels were analyzed by qRT-PCR which revealed that the monkey SOD1 mRNA was reduced by ~75% in 130 shRNA transduced cells compared to mock transduced control cells (Figures S5A-S5B).

Figure 7A:
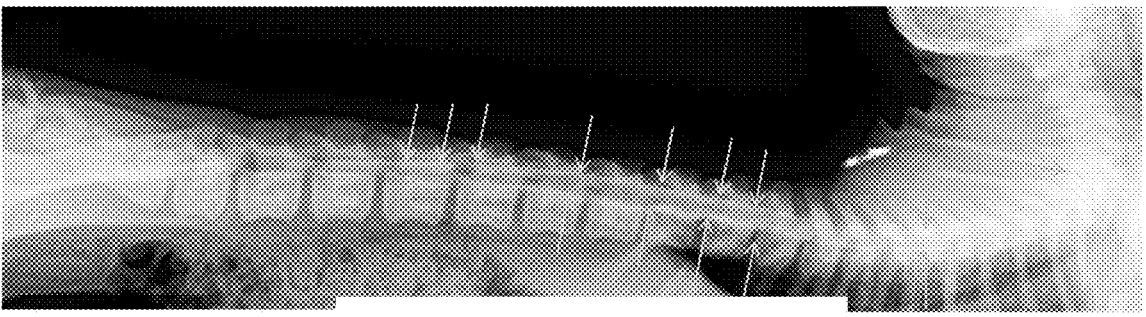
FIGS. 7A-7H. Intrathecal infusion of AAV9-SOD1-shRNA in non-human primates leads to efficient reduction in SOD1 levels.
Figure 7B:
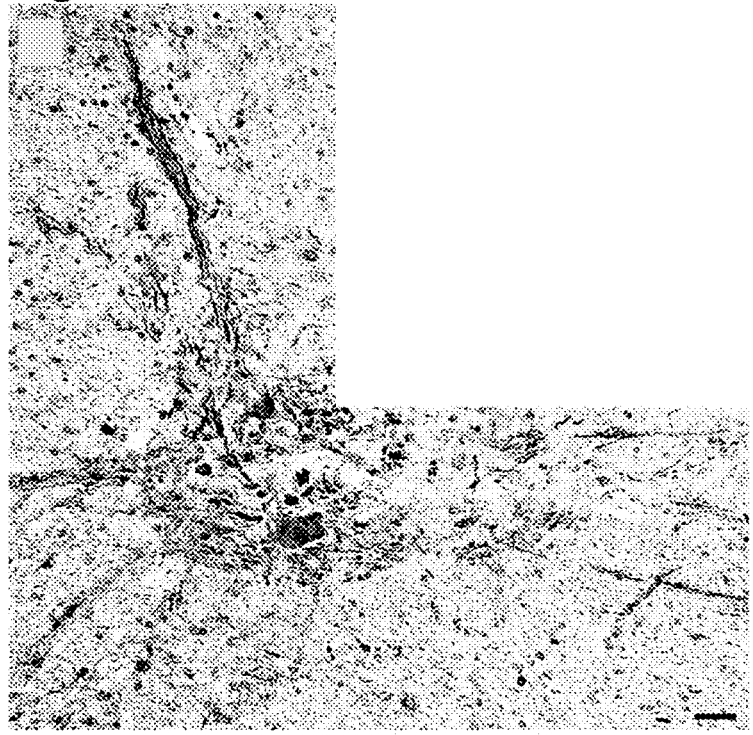
Figure 7C:
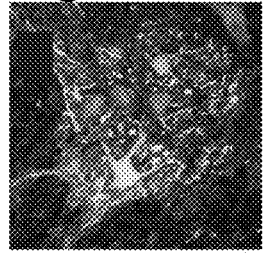
Figure 7D:
Figure 7E:
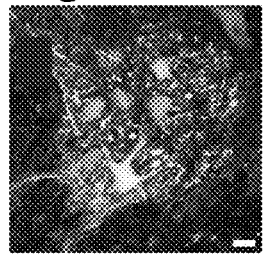

The AAV9-SOD1-shRNA virus ($1\times10^{13}$ vg/kg) was infused along with contrast agent via lumbar puncture into the subarachnoid space of three male cynomolgus macaques and one control subject was injected with AAV9-CB-GFP ($1\times10^{13}$ vg/kg) (FIG. 7A). Each intrathecal injection was performed by lumbar puncture into the subarachnoid space of the lumbar thecal sac. AAV9 was resuspended with omnipaque (iohexol), an iodinated compound routinely used in the clinical setting. Iohexol is used to validate successful subarachnoid space cannulation and was administered at a dose of 100 mg/Kg. The subject was placed in the lateral decubitus position and the posterior midline injection site at ~L4/L5 level identified (below the conus of the spinal cord). Under sterile conditions, a spinal needle with stylet was inserted and subarachnoid cannulation was confirmed with the flow of clear CSF from the needle. In order to decrease the pressure in the subarachnoid space, 0.8 ml of CSF was drained, immediately followed by injection with a mixture containing 0.7 mL iohexol (300 mg/ml formulation) mixed with 2.1 mL of virus (2.8 ml total).

Figure 7F:
Figure 7G:
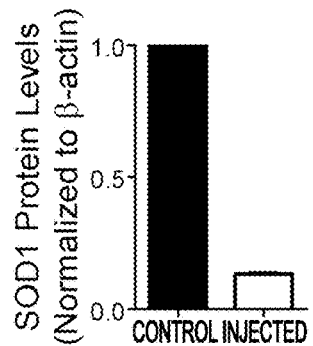
Figure 7H:
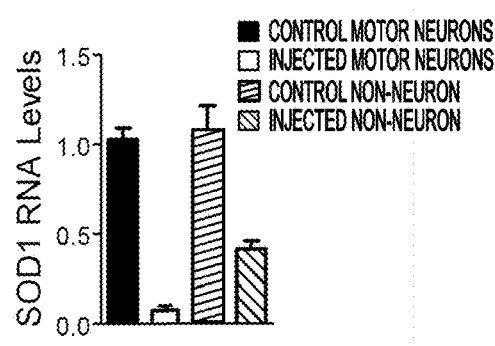

No side effects from the treatments were identified. Two weeks post injection, the spinal cords were harvested for analysis of GFP expression and SOD1 RNA levels. GFP expression was seen broadly in neuronal and astrocytic cells throughout the grey and white matter of the lumbar spinal cord, the area closest to the site of injection (FIG. 7B, FIG. 7C, FIG. 7D, FIG. 7E). Immunoblotting of extracts of lumbar spinal cord revealed 87% reduction in monkey SOD1 protein levels (FIG. 7F, FIG. 7G). Laser capture microdissection was then used to isolate total RNA from motor neurons as well as from glia in the nearby neuropil. Analysis by quantitative RT-PCR using primers specific for monkey SOD1 (and normalized to actin) confirmed a 95±3% knockdown in the motor neuron pool and a 66±9% knockdown in the neuropil pool when compared to samples from a control animal (FIG. 7H).

Next we examined the level of cell transduction throughout the spinal cord including cervical, thoracic and lumbar segments. GFP was found to be expressed broadly within all sections analyzed (FIGS. 8A-8C). Motor neuron counts revealed a caudal to rostral gradient in cell transduction, with the cervical region showing more than 50% of GFP/Chat+ motor neurons, increasing to 65% in the thoracic region and reaching a remarkable 80% in the lumbar region (FIG. 8D). In order to determine the overall level of SOD1 knockdown achieved with this transduction pattern, qRT-PCR for SOD1 was performed on whole section homogenates from cervical, thoracic and lumbar cord segments. The results confirmed robust SOD1 reduction at all three spinal cord levels, ranging from a 60% decrease in the cervical segment, a 70% decrease in the thoracic region and an 88% decrease in the lumbar region (FIG. 8E), consistent with the proportion of cells transduced in each region.

DISCUSSION

The examples above show that intravenous administration of AAV9-SOD1-shRNA is safe and well tolerated in wild type mice, with the absence of adverse effects after long-term assessment. This approach have achieved one of the longest extensions in survival ever reported in the rapidly progressive SOD1$^{G93A}$ mouse model of ALS (increasing survival by 39% when treatment is initiated at birth). Even more encouraging, markedly slowed disease progression is seen even when AAV9 therapy to reduce mutant SOD1 synthesis is applied after disease onset in SOD1$^{G37R}$ mice, thereby significantly extending survival. Thus, the vascular delivery paradigm in mice represents a proof of concept that mutant SOD1 knockdown after disease onset can be beneficial in both rapid and more slowly progressive models of ALS at clinically relevant points in disease. Together, these data show that robust targeting and suppression of SOD1 levels via AAV9-mediated delivery of shRNA is effective in slowing disease progression in mouse models of ALS, critically even when treatment is initiated after onset.

Multiple recent studies have brought forward the hypothesis that wild-type SOD1 may contribute through misfolding to the pathogenic mechanism(s) that underlie sporadic ALS through a pathway similar to that triggered by mutant SOD1[14,30-32] Included in this body of evidence is our own demonstration that astrocytes produced from sporadic ALS patients are toxic to co-cultured motor neurons and that toxicity is alleviated by siRNA-mediated reduction in wild type SOD1[30]. This evidence creates the potential that a proportion of sporadic ALS patients could also benefit from an AAV9-mediated SOD1 reduction approach that we have demonstrated to be effective in slowing disease progression in mice that develop fatal, ALS-like disease from expressing ALS-causing mutations in SOD1.

Finally, for translation of an AAV9-mediated suppression of SOD1 synthesis to the human setting, we have determined that infusion directly into the CSF at the lumbar level in a non-human primate produce substantial SOD1 reduction by targeting both motor neurons and non-neuronal cells. This outcome provides strong support for extending these efforts to an adult human by direct injection into CSF, as previously proposed[33,34], so as to 1) limit the cost of viral production, 2) reduce the possibility that chronic suppression of SOD1 in the periphery may have deleterious consequences, and 3) reduce viral exposure to the peripheral immune system[33]. These data strongly indicate AAV9-SOD1-shRNA as a treatment for ALS.

Techniques/Methods Used in Examples 1-7

Perfusion and Tissue Processing. Control and treated SOD1$^{G93A}$ mice were sacrificed at either 21 days post injection or at endstage for immunohistochemical analysis. Animals were anesthetized with xylazene/ketamine cocktail, transcardially perfused with 0.9% saline, followed by 4% paraformaldehyde. Spinal cords were harvested, cut into blocks of tissue 5-6 mm in length, and then cut into 40 μm thick transverse sections on a vibratome (Leica, Bannockburn, Ill.). Serial sections were kept in a 96-well plate that contained 4% paraformaldehyde and were stored at 4° C. End stage loxSOD1$^{G37R}$ mice were anesthetized using isoflurane and perfused with 4% paraformaldehyde. Spinal cord segments, including cervical, thoracic and lumbar segments were dissected. Following cryoprotection with 20% sucrose/4% paraformaldehyde overnight, spinal cords were frozen in isopentane at −65° C., and serial 30 μm coronal sections were collected free floating using sliding microtome.

For safety studies, P1, P21 treated and control wild type mice were sacrificed at 180 days of age. Animals were anesthetized using xylazene/ketamine cocktail and perfused with 0.9% saline. Different tissues were removed and stored in 10% buffered formalin. These tissues were further processed, blocked and mounted for hematoxilin & eosin staining by the Nationwide Children's Hospital Morphology Core.

Cynomolgus monkeys injected with virus were euthanized 2 weeks post injection. Animals were anesthetized with sodium pentobarbital at the dose of 80-100 mg/kg intravenously and perfused with saline solution. Brain and spinal cord dissection were performed immediately and tissues were processed either for nucleic acid isolation (snap frozen) or post-fixed in 4% paraformaldehyde and subsequently cryoprotected with 30% sucrose and frozen in isopentane at −65° C. 12 μm coronal sections were collected from lumbar cord using a cryostat for free floating immunostaining.

Immunohistochemistry.

Mouse spinal cords were stained as floating sections. Tissues were washed three-times for 10 minutes each in TBS, then blocked in a solution containing 10% donkey serum, 1% Triton X-100 and 1% penicillin/streptomycin for two hours at room temperature. All the antibodies were diluted with the blocking solution. Primary antibodies used were as follows: rabbit anti-GFP (1:400, Invitrogen, Carlsbad, Calif.), rabbit anti-SOD1 (1:200, Cell signaling, Danvers, Mass.), goat anti-ChAT (1:50 Millipore, Billerica, Mass.), mouse anti-GFAP (1:200, Millipore, Billerica, Mass.), chicken anti GFAP (1:400, Abcam, Cambridge, Mass.), and rabbit anti-Iba1 (1:400, Wako, Richmond Va.). Tissues were incubated in primary antibody at 4° C. for 48-72 hours then washed three times with TBS. After washing, tissues were incubated for 2 hours at room temperature in the appropriate FITC-, Cy3-, or Cy5-conjugated secondary antibodies (1:200 Jackson Immunoresearch, Westgrove, Pa.) and DAPI (1:1000, Invitrogen, Carlsbad, Calif.). Tissues were then washed three times with TBS, mounted onto slides then coverslipped with PVA-DABCO. All images were captured on a Zeiss-laser-scanning confocal microscope.

For DAB staining, monkey spinal cord sections were washed three times in TBS, blocked for 2 h at RT in 10% donkey serum and 1% Triton X-100. Sections were then incubated overnight at 4° C. with rabbit anti-GFP primary antibody (1:1000 Invitrogen, Carlsbad, Calif.) diluted in blocking buffer. The following day, tissues were washed with TBS 3 times, incubated with biotinylated secondary antibody anti-rabbit (1:200 Jackson Immunoresearch, Westgrove, Pa.) in blocking buffer for 30 min at RT, washed 3 times in TBS and incubated for 30 min at RT with ABC (Vector, Burlingame, Calif.). Sections were then washed for 3 times in TBS and incubated for 2 min with DAB solution at RT and washed with distilled water. These were then mounted onto slides and covered with coverslips in mounting medium. All images were captured with the Zeiss Axioscope.

Motor Neuron and Astrocyte Quantification.

For MN quantification, serial 40 μm thick lumbar spinal cord sections, each separated by 480 μm, were labeled as described for GFP and ChAT expression. Stained sections were serially mounted on slides from rostral to caudal, then coverslipped. Sections were evaluated using confocal microscopy (Zeiss) with a 40× objective and simultaneous FITC and Cy3 filters. The total number of ChAT positive cells found in the ventral horns with defined soma was tallied by careful examination through the entire z-extent of the section. GFP labeled cells were quantified in the same manner, while checking for co-localization with ChAT. For astrocyte quantification, as with MNs, serial sections were stained for GFP, GFAP and then mounted. Using confocal microscopy with a 63× objective and simultaneous FITC and Cy5 filters, random fields in the ventral horns of lumbar spinal cord sections from tail vein injected animals were selected. The total numbers of GFP and GFAP positive cells were counted from a minimum of at least 24-fields per animal while focusing through the entire z extent of the section. Spinal cord sections of 3 animals per group were examined for MN and astrocyte quantification.

Immunoblot Analysis.

Spinal cords were harvested from P1, P21 injected and control SOD1$^{G93A}$ mice 21 days post injection and from treated and control monkeys 2 weeks post injection of AAV9-SOD1-shRNA. Spinal cords were homogenized and protein lysates were prepared using T-Per (Pierce) with protease inhibitor cocktail. Samples were resolved on SDS-PAGE according to manufacturer's instructions. Primary antibodies used were rabbit anti-SOD1 (1:750, Cell signaling, Danvers, Mass.) mouse anti-SOD1 (1:750, Millipore, Billerica, Mass.), rabbit anti-SOD1 (1:1000, Abcam, Cambridge, Mass.), rabbit anti-Actin (1:1000, Abcam, Cambridge, Mass.) and mouse anti-GAPDH (1:1000, Millipore, Billerica, Mass.). Secondary antibodies used were anti-rabbit HRP (1:10000-1:50000) and anti-mouse HRP (1:10000). Densitometric analysis was performed using Image J software.

Laser Capture Microdissection.

12 μm lumbar spinal cord frozen sections were collected onto PEN membrane slides (Zeiss, Munich, Germany) and stained with 1% Cresyl violet (Sigma, St. Louis, Mo.) in methanol. Sections were air dried and stored at −80° C. After thawing, motor neurons were collected within 30 min from staining using the laser capture microdissector PALM Robo3 Zeiss) using the following settings: Cut energy: 48, LPC energy: 20, Cut focus: 80/81, LPC focus: 1, Position speed: 100, Cut speed: 50. About 500 MNs were collected per animal. Non-neuronal cells from the ventral horn were collected from the same sections after collecting the motor neurons.

qRT-PCR.

RNA from laser captured cells or whole spinal cord sections from the cervical, thoracic and lumbar segments was isolated using the RNaqueous Micro Kit (Ambion, Grand Island, N.Y.) according to manufacturer's instructions. RNA was then reverse-transcribed into cDNA using the $RT^2$ HT First Strand Kit (SABiosciences, Valencia, Calif.). 12.5 ng RNA were used in each Q-PCR reaction using SyBR Green (Invitrogen, Carlsbad, Calif.) to establish the relative quantity of endogenous monkey SOD1 transcript in animals who had received the AAV9-SOD1-shRNA compared to animals who had received only AAV9-GFP. Each sample was run in triplicate and relative concentration calculated using the ddCt values normalized to endogenous actin transcript.

Behavior and Survival Analysis.

Treated and control $SOD1^{G93A}$ mice were monitored for changes in body mass twice a week. $loxSOD1^{G37R}$ mice were weighed on a weekly basis. Motor coordination was recorded using a rotarod instrument (Columbus Instruments, Columbus, Ohio). Each weekly session consisted of three trials on the accelerating rotarod beginning at 5 rpm/min. The time each mouse remained on the rod was registered. Both $SOD1^{G93A}$ and $loxSOD1^{G37R}$ mice were subjected to weekly assessment of hindlimb grip strength using a grip strength meter (Columbus Instruments, Columbus, Ohio). Each weekly session consisted of 3 ($SOD1^{G93A}$ mice) or 5 ($loxSOD1^{G37R}$ mice) tests per animal. Survival analysis was performed using Kaplan-Meier survival analysis. End stage was defined as an artificial death point when animals could no longer "right" themselves within 30 sec after being placed on its back. Onset and disease progression were determined from retrospective analysis of the data. Disease onset is defined as the age at which the animal reached its peak weight. Disease duration is defined as the time period between disease onset and end stage. Early disease duration is the period between peak weight and loss of 10% of body weight while late disease duration is defined as the period between 10% loss of body weight until disease end stage. Due to shorter life span of $SOD1^{G93A}$ animals, we did not assess the distinction between the early and late progression.

For toxicity analysis following injection at P1 or P21, treated and control WT mice were subjected to behavioral analysis starting at ~30 days of age and monitored up to 6 months. Body mass was recorded weekly while rotarod performance and hindlimb grip strength were recorded biweekly.

Hematology and Serum Studies.

Blood samples were collected in (K2) EDTA microtainer tubes (BD) from treated and control WT mice at 150 days of age by mandibular vein puncture. The same animals were bled at 180 days of age and blood was collected in serum separator microtainer tubes. The blood was allowed to clot for an hour and was then centrifuged at 10,000 rpm for 5 minutes. The clear upper phase (serum) was collected and frozen at −80° C. Hematological and serum analysis were conducted by Ani Lytics Inc, Gaithersburg, Md.

Statistical Analysis.

All statistical tests were performed using the GraphPad Prism (San Diego, Calif.) software package. Kaplan Meier survival analyses were analyzed by the Log Rank Test. Comparisons of median disease durations and survival times were analyzed by the Wilcoxon Signed Rank Test.

Example 8

Development of a Clinical SOD1 shRNA Construct

The AAV SOD1 shRNA vector described in Example 2 carries shRNA against human SOD1 sequence under the H1 promoter (FIG. 9A). The same vector also contains a GFP expression cassette which expresses GFP under a CBA promoter. The other regulatory elements present in this cassette include CMV enhancer, SV40 intron and bGH PolyA terminator sequence. We show herein that AAV9 SOD1 shRNA administration results in efficient SOD1 downregulation along with robust expression of GFP in vitro as well as in vivo. No significant alterations were observed after the long term assessment of wild-type mice administered with AAV9 SOD1 shRNA. These results suggested that there are no evident off-target effects due to the long-term expression of SOD1 shRNA as well as overexpression of GFP. Although we did not find GFP toxicity in our mice, several reports have shown the adverse effects of GFP overexpression in vitro and in vivo. Therefore, to eliminate the possibility of GFP toxicity altogether, the SOD1 shRNA construct of Example 2 was modified by replacing the GFP expression cassette with a non-coding stuffer sequence while maintaining the size of the total DNA construct flanked by the ITRs (FIG. 9B). This is important as the distance between the two ITR sequences greatly affects the packaging capacity of the flanked construct into AAV9 capsids [321-324].

To date, none of the FDA approved stuffer sequences are readily available. There are, however, several plasmid backbones that are approved by FDA for the human administration. Small DNA fragments were picked from these plasmids which do not correspond to any essential DNA sequences necessary for selection and replication of the plasmid or the elements of the transcriptional units. The plasmid backbones are listed in Table 1. The DNA elements from different plasmids were arranged in tandem to generate a complete, 1607 bp stuffer sequence (SEQ ID NO: 22). Finally, a DNA construct containing the SOD1 shRNA expression cassette, followed by the stuffer sequence was synthesized from Genscript.

TABLE 1

| Plasmid Backbone | Condition | Intervention | Phase | ClinicalTrials.gov Identifier |
|---|---|---|---|---|
| pVax1 | Early Stage Non-Small Cell Lung Cancer | Recombinant DNA-pVAX/L523S | 1 | NCT00062907 |
| pCDNA3 | Chronic Hepatitis B | DNA vaccine pCMVS2.S | 1, 2 | NCT00536627 |
| pUCMV3 | Stage III Ovarian Epithelial Cancer Stage III Ovarian Germ Cell Tumor Stage IV Ovarian Epithelial Cancer Stage IV Ovarian Germ Cell Tumor | pUMVC3-hIGFBP-2 multi-epitope plasmid DNA vaccine | 1 | NCT01322802 |
| pBK-CMV | Prostate Cancer Bladder Cancer Non-Small Cell Lung Cancer Esophageal Cancer Sarcoma | NY-ESO-1 plasmid DNA Cancer Vaccine | 1 | NCT00199849 |
| pGA2 | HIV Infections | pGA2/JS2 Plasmid DNA Vaccine | 1 | NCT00043511 |

Figure 10:
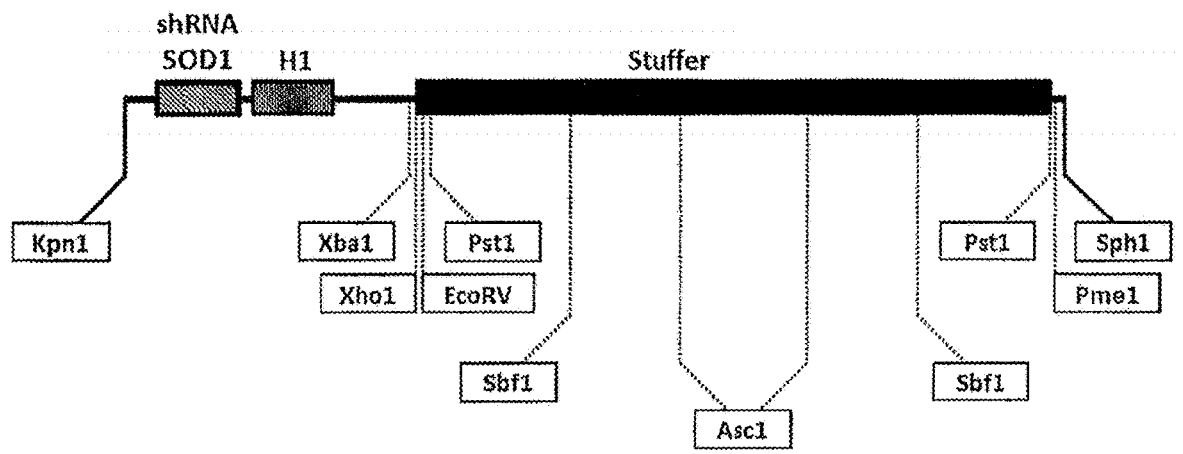
FIG. 10. Schematic of clinical SOD1 shRNA construct. Different restriction sites are placed in the clinical SOD1 shRNA construct that allow the cloning of multiple shRNA expression cassettes while maintaining the total distance between the two ITRs.
Figure 11:
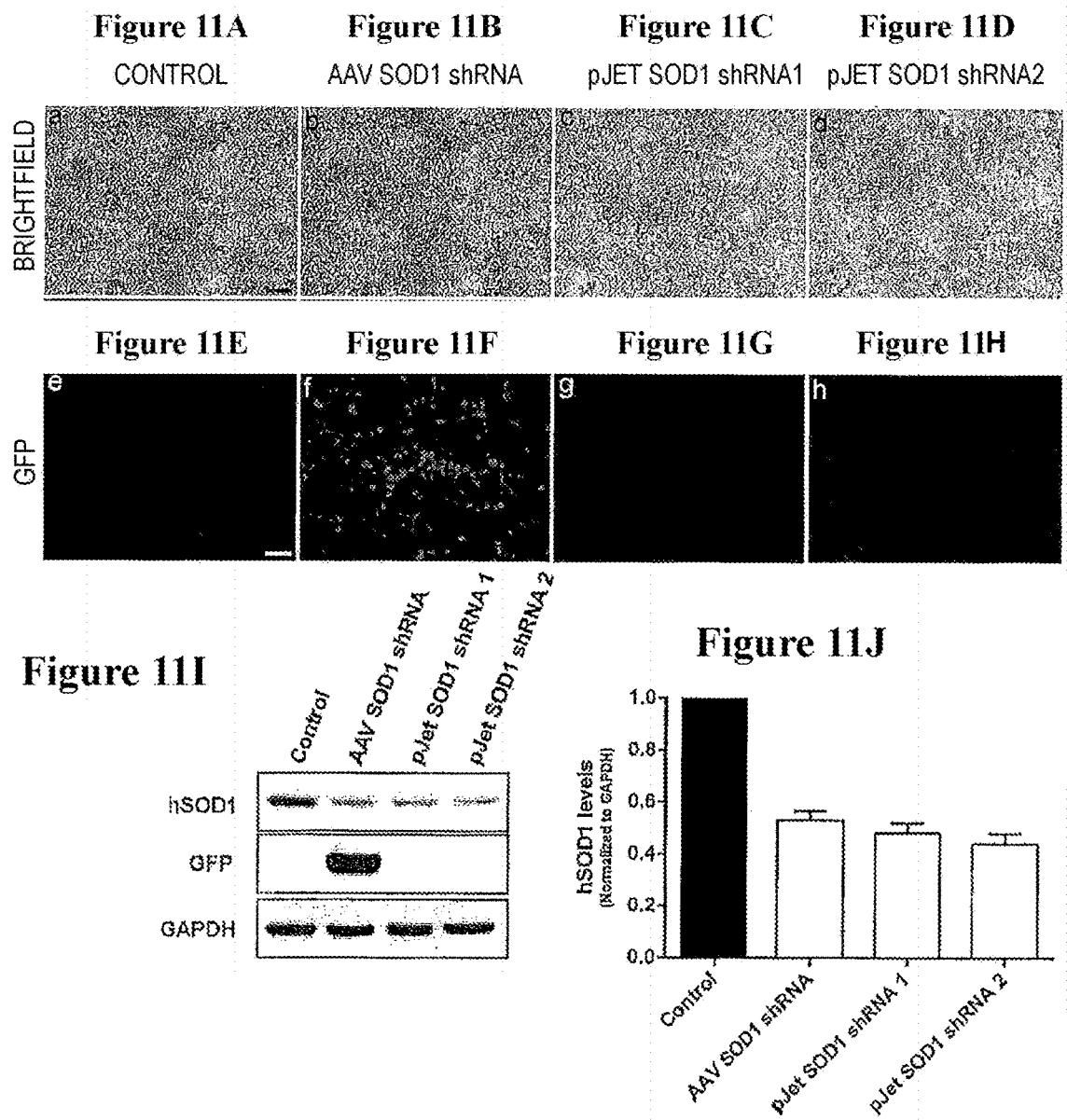
FIGS. 11A-11J. In vitro transfection of clinical SOD1 shRNA construct efficiently reduces human SOD1 protein in HEK293 cells. Representative microscopic fields showing bright-field images of non-transfected control (FIG. 11A), AAV SOD1 shRNA transfected (FIG. 11B) and shuttle vector pJet SOD1 shRNA transfected (FIG. 11C, FIG. 11D) HEK 293 cells, 72 hrs post transfection. Corresponding fluorescence images reveal the lack of GFP fluorescence from pJet SOD1 shRNA transfected HEK 293 cells (FIG. 11G, FIG. 11H) as compared to AAV SOD1 shRNA transfected cells (FIG. 11F).

Clinical SOD1 shRNA construct has shRNA against human SOD1 under H1 promoter which is followed by the non-coding stuffer sequence. This construct is designed in such a way that multiple shRNA expression cassettes can be added to the final vector by simultaneous removal of the stuffer sequence. Restriction endonuclease sites have been added to the stuffer sequence so that a part of the stuffer can be removed when another shRNA expression cassette is added (FIG. 10). This simultaneous removal and addition of DNA sequences would help maintaining the optimal size of the whole construct between the ITRs (~2.0 kb) to achieve efficient packaging.

Clinical SOD1 shRNA construct from Genscript was cloned into pJet1.2 shuttle vector via EcoRV. This parental clone was screened using various restriction endonucleases designed within the construct to confirm the correct clone. Kpn1/Sph1 double digestion of pJet SOD1 shRNA confirmed the presence of the complete construct (2023 bp) while Xba1 digestion confirmed the presence of SOD1 shRNA expression cassette (414 bp) and the stuffer element, along with pJet backbone (~3000 bp). EcoRV/Pme1 double digestion also revealed the presence of stuffer element.

Example 9

Clinical SOD1 shRNA Efficiently Reduces Human SOD1 Protein Levels In Vitro

To determine the efficacy of the de novo synthesized SOD1 shRNA construct to downregulate SOD1 levels, HEK293 cells were transfected with pJet SOD1 shRNA plasmid using Calcium Phosphate method. AAV SOD1 shRNA plasmid was used as a positive control. Immunofluorescence analysis of HEK293 cells, 72 hrs post transfection revealed the lack of native GFP fluorescence from pJet SOD1 shRNA transfected cells as compared to AAV9 SOD1 shRNA transfected cells. Immunoblot analysis of cell lysates from these cells further confirmed the successful replacement of GFP from pJet SOD1 shRNA plasmid. Importantly, pJet SOD1 shRNA resulted in efficient downregulation of SOD1 protein levels (>50%), similar to AAV SOD1 shRNA plasmid. See FIGS. 11A-11J.

Example 10

Generation of clinical AAV SOD1 shRNA

Figure 12:
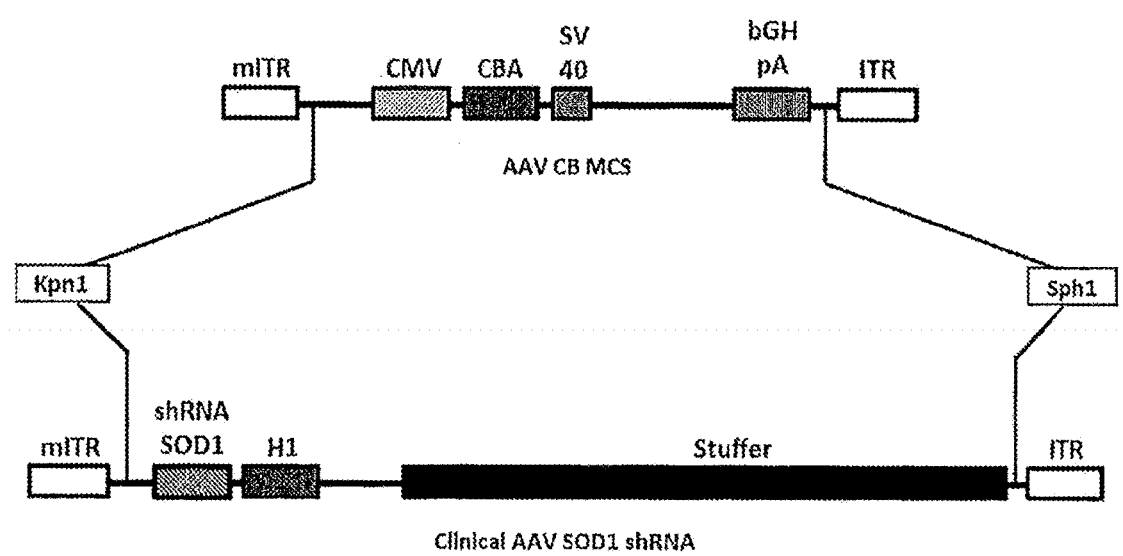
FIG. 12. Schematic of cloning strategy for clinical AAV SOD1 shRNA vector. Clinical SOD1 shRNA construct was cloned into AAV CB MCS vector using Kpn1/SPh1 sites. Kpn1/SPh1 double digest of AAV CB MCS plasmid results in the release of the complete transgene expression cassette from this vector which is further replaced with clinical SOD1 shRNA construct carrying SOD1 shRNA expression cassette and stuffer sequence.

Clinical SOD1 shRNA construct was further cloned into an AAV.CB.MCS vector using Kpn1/Sph1 sites to generate clinical AAV SOD1 shRNA plasmid (FIG. 12). AAV.CB.MCS was generated from AAV.CB.GFP plasmid obtained from merion Scientific by replacing GFP with a multiple cloning site (MCS). Cloning of clinical SOD1 shRNA construct at Kpn1/Sph1 sites puts it between the two AAV2 ITRs which facilitates the packaging of the construct in AAV9 viral capsids. See FIG. 12.

Clinical AAV SOD1 shRNA plasmid was screened with restriction endonucleases to confirm the presence of SOD1 shRNA expression cassette (Xba1 digest), stuffer sequence (EcoRV/Pme1 double digest) and also intact ITR sequences (Sma1 digest).

Example 11

Clinical AAV SOD1 shRNA Efficiently Reduces Human SOD1 Protein Levels In Vitro

Figure 13A:
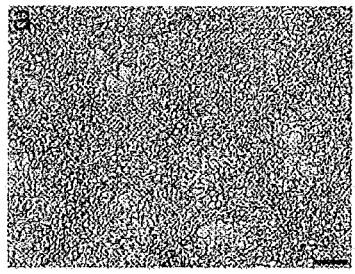
FIGS. 13A-13H. Clinical AAV SOD1 shRNA efficiently reduces human SOD1 levels in vitro. HEK293 cells were transfected with clinical AAV SOD1 shRNA plasmid by Calcium phosphate method. Representative microscopic fields showing brightfield images of non-transfected control, AAV SOD1 shRNA and Clinical AAV SOD1 shRNA transfected cells respectively, 72 hrs post-transfection (FIG. 13A, FIG. 13B, FIG. 13C). Successful removal of GFP from clinical AAV SOD1 shRNA was confirmed by lack of GFP expression in Clinical AAV SOD1 shRNA transfected cells (FIG. 13F, FIG. 13G.
Figure 13B:
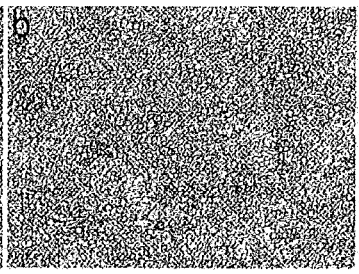
Figure 13C:
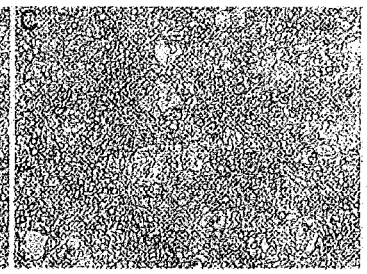
Figure 13D:
Figure 13E:
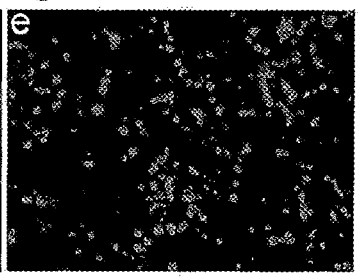
Figure 13F:
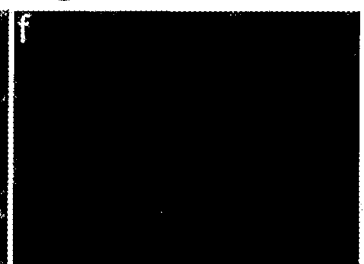
Figure 13G:
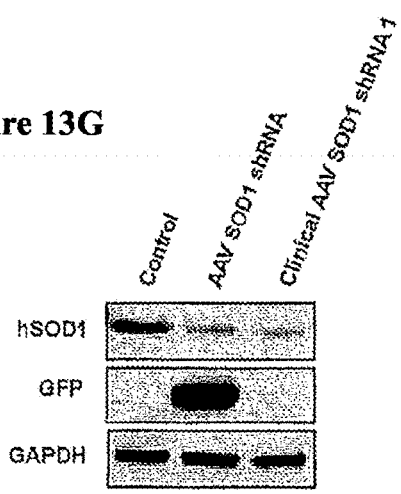
Figure 13H:
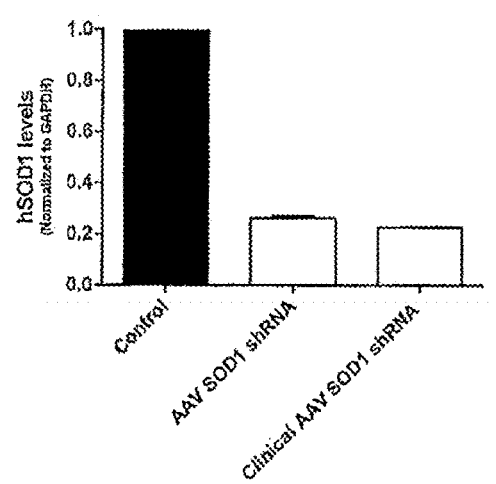

Clinical AAV SOD1 shRNA plasmid was transfected in HEK293 cells to determine its knockdown efficiency. Similar to the pJet SOD1 shRNA plasmid, clinical AAV SOD1 shRNA transfected cells were devoid of any GFP expression as evident by immunofluorescence (FIG. 13A, FIG. 13B, FIG. 13C, FIG. 13D, FIG. 13E, FIG. 13F) and immunoblot assay (FIG. 13G). More importantly, clinical AAV SOD1 shRNA efficiently reduced human SOD1 protein levels in HEK293 cells by more than 50% (FIG. 13G, FIG. 13H). Altogether, these results confirmed the successful generation of clinical AAV SOD1 shRNA vector with functional SOD1 shRNA expression cassette and complete removal of the transgene expression cassette.

DOCUMENTS REFERENCED

1. Da Cruz, S. & Cleveland, D. W. Understanding the role of TDP-43 and FUS/TLS in ALS and beyond. *Curr Opin Neurobiol* 21, 904-919 (2011).

2. Rosen, D. R. et al. Mutations in Cu/Zn superoxide dismutase gene are associated with familial amyotrophic lateral sclerosis. *Nature* 362, 59-62 (1993).
3. Ilieva, H., Polymenidou, M. & Cleveland, D. W. Non-cell autonomous toxicity in neurodegenerative disorders: ALS and beyond. *The Journal of cell biology* 187, 761-772 (2009).
4. Chattopadhyay, M. & Valentine, J. S. Aggregation of copper-zinc superoxide dismutase in familial and sporadic ALS. *Antioxidants & redox signaling* 11, 1603-1614 (2009).
5. Prudencio, M., Hart, P. J., Borchelt, D. R. & Andersen, P. M. Variation in aggregation propensities among ALS-associated variants of SOD1: correlation to human disease. *Human molecular genetics* 18, 3217-3226 (2009).
6. Boillee, S. et al. Onset and progression in inherited ALS determined by motor neurons and microglia. *Science* 312, 1389-1392 (2006).
7. Kang, S. H. et al. Degeneration and impaired regeneration of gray matter oligodendrocytes in amyotrophic lateral sclerosis. *Nature neuroscience* 16, 571-579 (2013).
8. Yamanaka, K. et al. Astrocytes as determinants of disease progression in inherited amyotrophic lateral sclerosis. *Nature neuroscience* 11, 251-253 (2008).
9. Di Giorgio, F. P., Boulting, G. L., Bobrowicz, S. & Eggan, K. C. Human embryonic stem cell-derived motor neurons are sensitive to the toxic effect of glial cells carrying an ALS-causing mutation. *Cell Stem Cell* 3, 637-648 (2008).
10. Di Giorgio, F. P., Carrasco, M. A., Siao, M. C., Maniatis, T. & Eggan, K. Non-cell autonomous effect of glia on motor neurons in an embryonic stem cell-based ALS model. *Nature neuroscience* 10, 608-614 (2007).
11. Marchetto, M. C. et al. Non-cell-autonomous effect of human SOD1 G37R astrocytes on motor neurons derived from human embryonic stem cells. *Cell Stem Cell* 3, 649-657 (2008).
12. Haidet-Phillips, A. M. et al. Astrocytes from familial and sporadic ALS patients are toxic to motor neurons. *Nat Biotechnol* 29, 824-828 (2011).
13. Bosco, D. A. et al. Wild-type and mutant SOD1 share an aberrant conformation and a common pathogenic pathway in ALS. *Nature neuroscience* 13, 1396-1403 (2010).
14. Pokrishevsky, E. et al. Aberrant localization of FUS and TDP43 is associated with misfolding of SOD1 in amyotrophic lateral sclerosis. *PloS one* 7, e35050 (2012).
15. Forsberg, K. et al. Novel antibodies reveal inclusions containing non-native SOD1 in sporadic ALS patients. *PLoS One* 5, e11552 (2010).
16. Aggarwal, S. & Cudkowicz, M. ALS drug development: reflections from the past and a way forward. *Neurotherapeutics: the journal of the American Society for Experimental Neuro Therapeutics* 5, 516-527 (2008).
17. Gurney, M. E. et al. Benefit of vitamin E, riluzole, and gabapentin in a transgenic model of familial amyotrophic lateral sclerosis. *Ann Neurol* 39, 147-157 (1996).
18. Foust, K. D. et al. Intravascular AAV9 preferentially targets neonatal neurons and adult astrocytes. *Nature biotechnology* 27, 59-65 (2009).
19. Duque, S. et al. Intravenous administration of self-complementary AAV9 enables transgene delivery to adult motor neurons. *Mol Ther* 17, 1187-1196 (2009).
20. Zhong, Z. et al. ALS-causing SOD1 mutants generate vascular changes prior to motor neuron degeneration. *Nature neuroscience* 11, 420-422 (2008).
21. Miller, R. G., Mitchell, J. D. & Moore, D. H. Riluzole for amyotrophic lateral sclerosis (ALS)/motor neuron disease (MND). *Cochrane Database Syst Rev* 3, CD001447 (2012).
22. Smith, R. A. et al. Antisense oligonucleotide therapy for neurodegenerative disease. *The Journal of clinical investigation* 116, 2290-2296 (2006).
23. Raoul, C. et al. Lentiviral-mediated silencing of SOD1 through RNA interference retards disease onset and progression in a mouse model of ALS. *Nat Med* 11, 423-428 (2005).
24. Ralph, G. S. et al. Silencing mutant SOD1 using RNAi protects against neurodegeneration and extends survival in an ALS model. *Nat Med* 11, 429-433 (2005).
25. Miller, T. M. et al. Virus-delivered small RNA silencing sustains strength in amyotrophic lateral sclerosis. *Annals of neurology* 57, 773-776 (2005).
26. Miller, T. M. et al. An antisense oligonucleotide against SOD1 delivered intrathecally for patients with SOD1 familial amyotrophic lateral sclerosis: a phase 1, randomised, first-in-man study. *Lancet neurology* 12, 435-442 (2013).
27. Towne, C., Raoul, C., Schneider, B. L. & Aebischer, P. Systemic AAV6 delivery mediating RNA interference against SOD1: neuromuscular transduction does not alter disease progression in fALS mice. *Mol Ther* 16, 1018-1025 (2008).
28. Towne, C., Setola, V., Schneider, B. L. & Aebischer, P. Neuroprotection by gene therapy targeting mutant SOD1 in individual pools of motor neurons does not translate into therapeutic benefit in fALS mice. *Mol Ther* 19, 274-283 (2011).
29. Mandel, R. J., Lowenstein, P. R. & Byrne, B. J. AAV6-mediated gene silencing fALS short. *Mol Ther* 19, 231-233 (2011).
30. Synofzik, M. et al. Mutant superoxide dismutase-1 indistinguishable from wild-type causes ALS. *Human molecular genetics* 21, 3568-3574 (2012).
31. Guareschi, S. et al. An over-oxidized form of superoxide dismutase found in sporadic amyotrophic lateral sclerosis with bulbar onset shares a toxic mechanism with mutant SOD1. *Proc Natl Acad Sci USA* 109, 5074-5079 (2012).
32. Haidet-Phillips, A. M. et al. Astrocytes from familial and sporadic ALS patients are toxic to motor neurons. *Nat Biotechnol* 29, 824-828 (2011).
33. Bevan, A. K. et al. Systemic gene delivery in large species for targeting spinal cord, brain, and peripheral tissues for pediatric disorders. *Mol Ther* 19, 1971-1980 (2011).
34. Gray, S. J. et al. Preclinical differences of intravascular AAV9 delivery to neurons and glia: a comparative study of adult mice and nonhuman primates. *Mol Ther* 19, 1058-1069 (2011).
35. Lioy, D. T. et al. A role for glia in the progression of Rett's syndrome. *Nature* 475, 497-500 (2011).
36. Miranda, C. J. et al. Aging brain microenvironment decreases hippocampal neurogenesis through Wnt-mediated survivin signaling. *Aging Cell* 11, 542-552 (2012).
37. Yamanaka, K. et al. Mutant SOD1 in cell types other than motor neurons and oligodendrocytes accelerates onset of disease in ALS mice. *Proc Natl Acad Sci USA* 105, 7594-7599 (2008).

All documents referred to in this application, including priority documents, are hereby incorporated by reference in their entirety with particular attention to the content for which they are referred.

We claim:

1. A recombinant adeno-associated virus comprising a superoxide dismutase 1 (SOD) shRNA-encoding DNA comprising a sequence selected from the group consisting of:

GCATCATCAATTTCGAGCAGAAGGAA, (SEQ ID NO: 1)

GAAGCATTAAAGGACTGACTGAA, (SEQ ID NO: 2)

CTGACTGAAGGCCTGCATGGATT, (SEQ ID NO: 3)

CATGGATTCCATGTTCATGA, (SEQ ID NO: 4)

GCATGGATTCCATGTTCATGA, (SEQ ID NO: 5)

GGTCTGGCCTATAAAGTAGTC, (SEQ ID NO: 6)

GGGCATCATCAATTTCGAGCA, (SEQ ID NO: 7)

GCATCATCAATTTCGAGCAGA, (SEQ ID NO: 8)

GCCTGCATGGATTCCATGTTC, (SEQ ID NO: 9)

GGAGGTCTGGCCTATAAAGTA, (SEQ ID NO: 10)

GATTCCATGTTCATGAGTTTG, (SEQ ID NO: 11)

GGAGATAATACAGCAGGCTGT, (SEQ ID NO: 12)

GCTTTAAAGTACCTGTAGTGA, (SEQ ID NO: 13)

GCATTAAAGGACTGACTGAAG, (SEQ ID NO: 14)

TCGAGCAGAAGGAAAGTAA, (SEQ ID NO: 16)

GCCTGCATGGATTCCATGT, (SEQ ID NO: 17)

TCACTCTCAGGAGACCATT, (SEQ ID NO: 18)

and

GCTTTAAAGTACCTGTAGT; (SEQ ID NO: 19)

wherein the recombinant adeno-associated virus genome lacks rep and cap genes.

2. A composition comprising the recombinant adeno-associated virus of claim 1 and a pharmaceutically acceptable carrier.

3. A method of inhibiting expression of mutant SOD1 in a cell comprising contacting the cell with the recombinant adeno-associated virus of claim 1, wherein the expression of SOD1 shRNA inhibits expression of the mutant SOD1 in the cell.

4. The recombinant adeno-associated virus of claim 1, further comprising an H1 promoter operably linked to the SOD1 shRNA-encoding DNA.

5. The recombinant adeno-associated virus of claim 1, wherein the recombinant adeno-associated virus is an rAAV2, rAAV9 or rAAVrh74 virus.

6. The recombinant adeno-associated virus of claim 1, further comprising a stutter sequence.

7. The recombinant adeno-associated virus of claim 1, wherein the SOD1 shRNA-encoding DNA comprises SEQ ID NO: 4.

8. The recombinant adeno-associated virus of claim 1, wherein the SOD1 shRNA-encoding DNA comprises, from 5' to 3'; a) nucleotides 104-123 of SEQ ID NO: 21; b) a stem loop; and c) nucleotides 133-152 of SEQ ID NO: 21.

9. A method of treating amyotrophic lateral sclerosis (ALS) comprising administering to a subject having a mutation in the SOD1 gene an effective dose of a composition comprising a recombinant adeno-associated virus comprising a SOD1 shRNA-encoding DNA comprising a sequence selected from the group consisting of:

```
                            (SEQ ID NO: 1)
GCATCATCAATTTCGAGCAGAAGGAA, (SEQ ID NO: 2)
GAAGCATTAAAGGACTGACTGAA, (SEQ ID NO: 3)
CTGACTGAAGGCCTGCATGGATT, (SEQ ID NO: 4)
CATGGATTCCATGTTCATGA, (SEQ ID NO: 5)
GCATGGATTCCATGTTCATGA, (SEQ ID NO: 6)
GGTCTGGCCTATAAAGTAGTC, (SEQ ID NO: 7)
GGGCATCATCAATTTCGAGCA, (SEQ ID NO: 8)
GCATCATCAATTTCGAGCAGA, (SEQ ID NO: 9)
GCCTGCATGGATTCCATGTTC, (SEQ ID NO: 10)
GGAGGTCTGGCCTATAAAGTA, (SEQ ID NO: 11)
GATTCCATGTTCATGAGTTTG, (SEQ ID NO: 12)
GGAGATAATACAGCAGGCTGT, (SEQ ID NO: 13)
GCTTTAAAGTACCTGTAGTGA, (SEQ ID NO: 14)
GCATTAAAGGACTGACTGAAG, (SEQ ID NO: 16)
TCGAGCAGAAGGAAAGTAA, (SEQ ID NO: 17)
GCCTGCATGGATTCCATGT, (SEQ ID NO: 18)
TCACTCTCAGGAGACCATT,
and
                            (SEQ ID NO: 19)
GCTTTAAAGTACCTGTAGT;
``` wherein the recombinant adeno-associated virus genome lacks rep and cap genes.

10. The method of claim 9, wherein the recombinant adeno-associated virus is administered by parenteral, intravenous, intrathecal, introcerebroventricular, or cisterna magna administration.

11. The method of claim 10, wherein the intrathecal administration is by lumbar puncture.

12. The method of claim 9, further comprising delivering a contrast agent to the subject.

13. The method of claim 12, wherein the contrast agent is iobitridol, iohexol, iomeprol, iopamidol, iopentol, iopromide, ioversol or ioxilan.

14. The method of claim 9, wherein the SOD1 shRNA-encoding DNA comprises SEQ ID NO: 4.

15. The method of claim 9, wherein the SOD1 shRNA-encoding DNA comprises, from 5' to 3'; a) nucleotides 104-123 of SEQ ID NO: 21; b) a stem loop; and c) nucleotides 133-152 of SEQ ID NO: 21.

* * * * *

UNITED STATES PATENT AND TRADEMARK OFFICE
CERTIFICATE OF CORRECTION

| | |
|---|---|
| PATENT NO. | : 10,793,861 B2 |
| APPLICATION NO. | : 16/041381 |
| DATED | : October 6, 2020 |
| INVENTOR(S) | : Brian K. Kaspar et al. |

It is certified that error appears in the above-identified patent and that said Letters Patent is hereby corrected as shown below:

In the Specification

Column 1, Line 34, replace "U.S. National Institutes of Health R21-NS067238, NS027036, ROI NS064492 and RC2 NS69476-01." with --NS067238, NS027036, NS069476, NS064492, GM068524 and NS073269 awarded by the National Institutes of Health.--

Signed and Sealed this
Sixteenth Day of August, 2022

Katherine Kelly Vidal
*Director of the United States Patent and Trademark Office*

SEQUENCE LISTING

<160> NUMBER OF SEQ ID NOS: 22

<210> SEQ ID NO 1
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 1
gcatcatcaa tttcgagcag aaggaa                                26

<210> SEQ ID NO 2
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 2
gaagcattaa aggactgact gaa                                   23

<210> SEQ ID NO 3
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 3
ctgactgaag gcctgcatgg att                                   23

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
catggattcc atgttcatga                                       20

<210> SEQ ID NO 5
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 5
gcatggattc catgttcatg a                                     21

<210> SEQ ID NO 6
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 6
ggtctggcct ataaagtagt c                                     21

<210> SEQ ID NO 7
<211> LENGTH: 21
<212> TYPE: DNA
<213> ORGANISM: Artificial Sequence

```
<220> FEATURE:
<223> OTHER INFORMATION: Synthetic Polynucleotide

<400> SEQUENCE: 7
gggcatcatc aatttcgagc a                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 8
gcatcatcaa tttcgagcag a                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 9
gcctgcatgg attccatgtt c                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 10
ggaggtctgg cctataaagt a                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 11
gattccatgt tcatgagttt g                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 12
ggagataata cagcaggctg t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 13
gctttaaagt acctgtagtg a                                              21
```

<210> SEQ ID NO 14
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 14
gcattaaagg actgactgaa g                                            21

<210> SEQ ID NO 15
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 15
tcatcaattt cgagcagaa                                               19

<210> SEQ ID NO 16
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 16
tcgagcagaa ggaaagtaa                                               19

<210> SEQ ID NO 17
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 17
gcctgcatgg attccatgt                                               19

<210> SEQ ID NO 18
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 18
tcactctcag gagaccatt                                               19

<210> SEQ ID NO 19
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 19
gctttaaagt acctgtagt                                               19

<210> SEQ ID NO 20
<211> LENGTH: 5786
<212> TYPE: DNA
<213> ORGANISM: Artificial Sequence
<220> FEATURE:
<223> OTHER INFORMATION: Synthetic Polynucleotide

<400> SEQUENCE: 20

```
gcccaatacg caaaccgcct ctccccgcgc gttggccgat tcattaatgc agctgattct      60
aacgaggaaa gcacgttata cgtgctcgtc aaagcaacca tagtacgcgc cctgtagcgg     120
cgcattaagc gcggcgggtg tggtggttac gcgcagcgtg accgctacac ttgccagcgc     180
cctagcgccc gctcctttcg ctttcttccc ttcctttctc gccacgttcg ccggctttcc     240
ccgtcaagct ctaaatcggg ggctcccttt agggttccga tttagtgctt tacggcacct     300
cgaccccaaa aaacttgatt agggtgatgg ttcacgtagt gggccatcgc cctgatagac     360
ggtttttcgc cctttgacgt tggagtccac gttctttaat agtggactct tgttccaaac     420
tggaacaaca ctcaacccta tctcggtcta ttcttttgat ttataaggga ttttgccgat     480
ttcggcctat tggttaaaaa atgagctgat ttaacaaaaa tttaacgcga attttaacaa     540
aatattaacg cttacaattt aaatatttgc ttatacaatc ttcctgtttt tggggctttt     600
ctgattatca accggggtac atatgattga catgctagtt ttacgattac cgttcatcgc     660
cctgcgcgct cgctcgctca ctgaggccgc ccgggcaaag cccgggcgtc gggcgacctt     720
tggtcgcccg gcctcagtga gcgagcgagc gcgcagagag ggagtggaat tcacgcgtgg     780
atctgaattc aattcacgcg tggtacctac actttatgct tccggctcgt atgttgtgtg     840
gaattgtgag cggataacaa tttcacacag gaaacagcta tgaccatgat tacgccaagc     900
tttccaaaaa agcatggatt ccatgttcat gatctcttga atcatgaaca tggaatccat     960
ggatccgagt ggtctcatac agaacttata agattcccaa atccaaagac atttcacgtt    1020
tatggtgatt tcccagaaca catagcgaca tgcaaatatg aattcactgg ccgtcgtttt    1080
acaacgtcgt gactgggaaa accctggcgt tacccaactt aatcgccttg cagcacatcc    1140
ccctttcgcc agctggcgta atagcgaaga ggcccgcacc gatcgccctt cccaacagtt    1200
gcgcagcctg tggtacctct ggtcgttaca taacttacgg taaatggccc gcctggctga    1260
ccgcccaacg acccccgccc attgacgtca ataatgacgt atgttcccat agtaacgcca    1320
atagggactt tccattgacg tcaatgggtg gagtatttac ggtaaactgc ccacttggca    1380
gtacatcaag tgtatcatat gccaagtacg ccccctattg acgtcaatga cggtaaatgg    1440
cccgcctggc attatgccca gtacatgacc ttatgggact ttcctacttg gcagtacatc    1500
tactcgaggc cacgttctgc ttcactctcc ccatctcccc cccctcccca ccccaatttt    1560
tgtatttatt tattttttaa ttattttgtg cagcgatggg ggcggggggg ggggggggc     1620
gcgcgccagg cggggcgggg cggggcgagg ggcggggcgg ggcgaggcgg agaggtgcgg    1680
cggcagccaa tcagagcggc gcgctccgaa agtttccttt tatggcgagg cggcggcggc    1740
ggcggcccta taaaaagcga agcgcgcggc gggcgggagc gggatcagcc accgcggtgg    1800
cggcctagag tcgacgagga actgaaaaac cagaaagtta actggtaagt ttagtctttt    1860
tgtcttttat ttcaggtccc ggatccggtg gtggtgcaaa tcaaagaact gctcctcagt    1920
ggatgttgcc tttacttcta ggcctgtacg gaagtgttac ttctgctcta aaagctgcgg    1980
aattgtaccc gcggccgatc caccggtcgc caccatggtg agcaagggcg aggagctgtt    2040
caccggggtg gtgcccatcc tggtcgagct ggacggcgac gtaaacggcc acaagttcag    2100
cgtgtccggc gagggcgagg gcgatgccac ctacggcaag ctgaccctga agttcatctg    2160
caccaccggc aagctgcccg tgccctggcc caccctcgtg accaccctga cctacggcgt    2220
gcagtgcttc agccgctacc ccgaccacat gaagcagcac gacttcttca agtccgccat    2280
```

```
gcccgaaggc tacgtccagg agcgcaccat cttcttcaag gacgacggca actacaagac      2340
ccgcgccgag gtgaagttcg agggcgacac cctggtgaac cgcatcgagc tgaagggcat      2400
cgacttcaag gaggacggca acatcctggg gcacaagctg gagtacaact acaacagcca      2460
caacgtctat atcatggccg acaagcagaa gaacggcatc aaggtgaact tcaagatccg      2520
ccacaacatc gaggacggca gcgtgcagct cgccgaccac taccagcaga cacccccat      2580 cggcgacggc cccgtgctgc tgcccgacaa ccactacctg agcacccagt ccgccctgag      2640
caaagacccc aacgagaagc gcgatcacat ggtcctgctg gagttcgtga ccgccgccgg      2700
gatcactctc ggcatggacg agctgtacaa gtaaagcggc catcaagctt atcgataccg      2760
tcgactagag ctcgctgatc agcctcgact gtgccttcta gttgccagcc atctgttgtt      2820
tgcccctccc ccgtgccttc cttgaccctg gaaggtgcca ctcccactgt cctttcctaa      2880
taaaatgagg aaattgcatc gcattgtctg agtaggtgtc attctattct ggggggtggg      2940
gtggggcagg acagcaaggg ggaggattgg gaagacaata gcaggcatgc tggggagaga      3000
tcgatctgag gaaccctag tgatggagtt ggccactccc tctctgcgcg ctcgctcgct      3060
cactgaggcc gggcgaccaa aggtcgcccg acgcccgggc tttgcccggg cggcctcagt      3120
gagcgagcga gcgcgcagag agggagtggc cccccccccc cccccccggg cgattctctt      3180
gtttgctcca gactctcagg caatgacctg atagcctttg tagagacctc tcaaaaatag      3240
ctaccctctc cggcatgaat ttatcagcta gaacggttga atatcatatt gatggtgatt      3300
tgactgtctc cggcctttct cacccgtttg aatctttacc tacacattac tcaggcattg      3360
catttaaaat atatgagggt tctaaaaatt tttatccttg cgttgaaata aaggcttctc      3420
ccgcaaaagt attacagggt cataatgttt ttggtacaac cgatttagct ttatgctctg      3480
aggctttatt gcttaattt gctaattctt tgccttgcct gtatgattta ttggatgttg      3540
gaatcgcctg atgcggtatt ttctccttac gcatctgtgc ggtatttcac accgcatatg      3600
gtgcactctc agtacaatct gctctgatgc cgcatagtta agccagcccc gacacccgcc      3660
aacacccgct gacgcgccct gacgggcttg tctgctcccg gcatccgctt acagacaagc      3720
tgtgaccgtc tccgggagct gcatgtgtca gaggttttca ccgtcatcac cgaaacgcgc      3780
gagacgaaag ggcctcgtga tacgcctatt tttataggtt aatgtcatga taataatggt      3840
ttcttagacg tcaggtggca cttttcgggg aaatgtgcgc ggaacccta tttgtttatt      3900 tttctaaata cattcaaata tgtatccgct catgagacaa taaccctgat aaatgcttca      3960
ataatattga aaaggaaga gtatgagtat tcaacatttc cgtgtcgccc ttattccctt      4020
ttttgcggca ttttgccttc ctgttttgc tcacccagaa acgctggtga agtaaaaga      4080 tgctgaagat cagttgggtg cacgagtggg ttacatcgaa ctggatctca acagcggtaa      4140
gatccttgag agttttcgcc ccgaagaacg ttttccaatg atgagcactt ttaaagttct      4200
gctatgtggc gcggtattat cccgtattga cgccgggcaa gagcaactcg gtcgccgcat      4260
acactattct cagaatgact tggttgagta ctcaccagtc acagaaaagc atcttacgga      4320
tggcatgaca gtaagagaat tatgcagtgc tgccataacc atgagtgata acactgcggc      4380
caacttactt ctgacaacga tcggaggacc gaaggagcta accgcttttt tgcacaacat      4440
gggggatcat gtaactcgcc ttgatcgttg ggaaccggag ctgaatgaag ccataccaaa      4500
cgacgagcgt gacaccacga tgcctgtagc aatggcaaca acgttgcgca aactattaac      4560
tggcgaacta cttactctag cttcccggca acaattaata gactggatgg aggcggataa      4620
agttgcagga ccacttctgc gctcggccct tccggctggc tggtttattg ctgataaatc      4680
```

```
tggagccggt gagcgtgggt ctcgcggtat cattgcagca ctggggccag atggtaagcc    4740
ctcccgtatc gtagttatct acacgacggg gagtcaggca actatggatg aacgaaatag    4800
acagatcgct gagataggtg cctcactgat taagcattgg taactgtcag accaagttta    4860
ctcatatata ctttagattg atttaaaact tcatttttaa tttaaaagga tctaggtgaa    4920
gatccttttt gataatctca tgaccaaaat cccttaacgt gagttttcgt tccactgagc    4980
gtcagacccc gtagaaaaga tcaaaggatc ttcttgagat ccttttttc tgcgcgtaat     5040 ctgctgcttg caaacaaaaa aaccaccgct accagcggtg gtttgtttgc cggatcaaga    5100
gctaccaact cttttccga aggtaactgg cttcagcaga gcgcagatac caaatactgt     5160
ccttctagtg tagccgtagt taggccacca cttcaagaac tctgtagcac cgcctacata    5220
cctcgctctg ctaatcctgt taccagtggc tgctgccagt ggcgataagt cgtgtcttac    5280
cgggttggac tcaagacgat agttaccgga taaggcgcag cggtcgggct gaacggggggg   5340 ttcgtgcaca gcccagct tggagcgaac gacctacacc gaactgagat acctacagcg      5400
tgagctatga gaaagcgcca cgcttcccga agggagaaag gcggacaggt atccggtaag    5460
cggcagggtc ggaacaggag agcgcacgag ggagcttcca gggggaaacg cctggtatct    5520
ttatagtcct gtcgggtttc gccacctctg acttgagcgt cgatttttgt gatgctcgtc    5580 agggggggcgg agcctatgga aaaacgccag caacgcggcc ttttacggt tcctggcctt     5640 ttgctggcct tttgctcaca tgttctttcc tgcgttatcc cctgattctg tggataaccg    5700
tattaccgcc tttgagtgag ctgataccgc tcgccgcagc cgaacgaccg agcgcagcga    5760
gtcagtgagc gaggaagcgg aagagc                                         5786

<210> SEQ ID NO 21
<211> LENGTH: 164
<212> TYPE: DNA
<213> ORGANISM: Artificial Sequence
<220> FEATURE:
<223> OTHER INFORMATION: Synthetic Polynucleotide

<400> SEQUENCE: 21
aattcatatt tgcatgtcgc tatgtgttct gggaaatcac cataaacgtg aaatgtcttt     60
ggatttggga atcttataag ttctgtatga gaccactcgg atccatggat tccatgttca   120
tgattcaaga gatcatgaac atggaatcca tgcttttttg gaaa                    164

<210> SEQ ID NO 22
<211> LENGTH: 1607
<212> TYPE: DNA
<213> ORGANISM: Artificial Sequence
<220> FEATURE:
<223> OTHER INFORMATION: Synthetic Polynucleotide

<400> SEQUENCE: 22
tctagaggct cgagaagata tcaactgcag cttctactgg gcggttttat ggacagcaag     60
cgaaccggaa ttgccagctg gggcgccctc tggtaaggtt gggaagccct gcaaagtaaa   120
ctggatggct ttctcgccgc caaggatctg atggcgcagg ggatcaagct ctgatcaaga   180
gacaggatga ggatcgtttc gcgttcttga ctcttcgcga tgtacgggcc agatatacgc   240
gttgacattg attattgact agttattaat agtaatcaat tacgggtca ttagttcata    300 gcccatatat ggagttccgc ctgcaggac gtcgacggat cggagatct cccgatcccc     360 tatctgctcc ctgcttgtgt gttggaggtc gctgagtagt gcgcgagcaa aatttaagct   420
```

```
acaacaaggc aaggcttgac cgacaattgc atgaagaatc tgcttagggt taggcgtttt    480
gcgctgcttc gcggcgcgcc ttttaaggca gttattggtg cccttaaacg cctggtgcta    540
cgcctgaata agtgataata agcggatgaa tggcagaaat tcgccggatc tttgtgaagg    600
aaccttactt ctgtggtgtg acataattgg acaaactacc tacagagatt taaagctcta    660
atgtaagcag acagttttat tgttcatgat gatatatttt tatcttgtgc aatgtaacat    720
cagagatttt gagacacaac gtggctttcc cccccccccc ctagggtggg cgaagaactc    780
cagcatgaga tccccgcgct ggaggatcat ccagccggcg tcccggaaaa cgattccgaa    840
gcccaacctt tcatagaagg cggcggtgga atcgaaatct cgtgatggca ggttgggcgt    900
cgcttggtcg gtcatttcga accccagagt cccgctcagg gcgcgccggg ggggggggcg    960
ctgaggtctg cctcgtgaag aaggtgttgc tgactcatac caggcctgaa tcgccccatc   1020
atccagccag aaagtgaggg agccacggtt gatgagagct ttgttgtagg tggaccagtc   1080
ctgcaggagc ataaagtgta aagcctgggg tgcctaatga gtgagctaac tcacattaat   1140
tgcgttgcgc tcactgcccg ctttccagtc gggaaacctg tcgtgccccgc ccagtctagc   1200 tatcgccatg taagcccact gcaagctacc tgctttctct ttgcgcttgc gttttcccttt   1260 gtccagatag cccagtagct gacattcatc cggggtcagc accgtttctg cggactggct   1320
ttctacgtgt ctggttcgag gcgggatcag ccaccgcggt ggcggcctag agtcgacgag   1380
gaactgaaaa accagaaagt taactggcct gtacggaagt gttacttctg ctctaaaagc   1440
tgcggaattg tacccgcggc cgatccaccg gtcgccacca gcggccatca agcacgttat   1500
cgataccgtc gactagagct cgctgatcag tgggggtgg ggtggggcag gacagcaagg   1560
gggaggattg ggaagacaat agcagctgca gaagtttaaa cgcatgc                 1607
```